US012060328B2

(12) United States Patent
Knight et al.

(10) Patent No.: US 12,060,328 B2
(45) Date of Patent: Aug. 13, 2024

(54) CO-CRYSTALS OR SALTS OF PSILOCYBIN AND METHODS OF TREATMENT THEREWITH

(71) Applicant: RESET PHARMACEUTICALS, INC., Great Neck, NY (US)

(72) Inventors: John Knight, Hereford (GB); Talbir Austin, Loughborough (GB)

(73) Assignee: RESET PHARMACEUTICALS, INC., Great Neck, NY (US)

( * ) Notice: Subject to any disclaimer, the term of this patent is extended or adjusted under 35 U.S.C. 154(b) by 0 days.

(21) Appl. No.: 18/116,885

(22) Filed: Mar. 3, 2023

(65) Prior Publication Data

US 2023/0279032 A1    Sep. 7, 2023

Related U.S. Application Data

(60) Provisional application No. 63/322,697, filed on Mar. 23, 2022, provisional application No. 63/322,703, filed on Mar. 23, 2022, provisional application No. 63/322,701, filed on Mar. 23, 2022, provisional application No. 63/316,612, filed on Mar. 4, 2022, (Continued)

(51) Int. Cl.
*C07D 209/16*   (2006.01)
*C07F 9/572*   (2006.01)

(52) U.S. Cl.
CPC .......... *C07D 209/16* (2013.01); *C07F 9/5728* (2013.01); *C07B 2200/13* (2013.01)

(58) Field of Classification Search
CPC .. C07D 209/16; C07F 9/5728; C07B 2200/13
See application file for complete search history.

(56) References Cited

U.S. PATENT DOCUMENTS

| 3,072,530 A | 1/1963 | Hofmann et al. |
| 8,512,748 B2 | 8/2013 | Pearnchob et al. |

(Continued)

FOREIGN PATENT DOCUMENTS

| CA | 3088384 A1 | 10/2020 |
| CN | 108619214 A | 10/2018 |

(Continued)

OTHER PUBLICATIONS

S.E. David, P. Timmins & B.R. Conway (2012) Impact of the counterion on the solubility and physicochemical properties of salts of carboxylic acid drugs, Drug Development and Industrial Pharmacy, 38:1, 93-103, DOI: 10.3109/03639045.2011.592530 (Year: 2012).*

(Continued)

*Primary Examiner* — Noble E Jarrell
*Assistant Examiner* — Richard Grant Peckham
(74) *Attorney, Agent, or Firm* — MH2 TECHNOLOGY LAW GROUP, LLP

(57) ABSTRACT

The invention relates to a co-crystal or salt comprising psilocybin and a co-former. The co-crystal or salt is useful in methods of treating or preventing a disease or condition selected from depression, anxiety, death anxiety, demoralization, adjustment disorders, hopelessness, suicidal ideation, desire for hastened death, cocaine-related disorders, opioid-related disorders and stimulant-related disorders in a patient. A kit comprising the co-crystal or salt is also described.

13 Claims, 15 Drawing Sheets

Related U.S. Application Data provisional application No. 63/316,627, filed on Mar. 4, 2022, provisional application No. 63/316,621, filed on Mar. 4, 2022.

(56) References Cited

U.S. PATENT DOCUMENTS

| | | |
|---|---|---|
| 8,795,720 B2 | 8/2014 | Madit |
| 8,883,233 B2 | 11/2014 | Gillessen et al. |
| 8,907,153 B2 | 12/2014 | Zhang et al. |
| 9,044,402 B2 | 6/2015 | Tygesen |
| 9,050,343 B2 | 6/2015 | Peters et al. |
| 9,226,925 B1 | 1/2016 | King et al. |
| 9,421,266 B2 | 8/2016 | King et al. |
| 9,517,254 B2 | 12/2016 | Sitchon et al. |
| 9,522,120 B2 | 12/2016 | Tengler et al. |
| 9,549,901 B2 | 1/2017 | Xiao et al. |
| 9,554,989 B2 | 1/2017 | Kaplan et al. |
| 10,085,995 B2 | 10/2018 | Lozinsky et al. |
| 10,092,609 B2 | 10/2018 | Wieser et al. |
| 10,183,001 B1 | 1/2019 | King et al. |
| 10,188,083 B2 | 1/2019 | Leo |
| 10,478,429 B2 | 11/2019 | Hughey et al. |
| 10,519,175 B2 | 12/2019 | Londesbrough et al. |
| 10,596,378 B2 | 3/2020 | Rustick |
| 10,881,607 B2 | 1/2021 | Schmitz et al. |
| 10,947,257 B2 | 3/2021 | Londesbrough et al. |
| 10,954,259 B1 | 3/2021 | Londesbrough et al. |
| 11,000,534 B1 * | 5/2021 | Sippy .................. A61K 31/675 |
| 11,149,044 B2 | 10/2021 | Londesbrough et al. |
| 11,180,517 B2 | 11/2021 | Londesbrough et al. |
| 11,312,684 B1 | 4/2022 | Nichols et al. |
| 11,344,564 B1 | 5/2022 | Sippy |
| 11,447,510 B2 | 9/2022 | Londesbrough et al. |
| 11,505,564 B2 | 11/2022 | Londesbrough et al. |
| 11,629,159 B2 | 4/2023 | Londesbrough et al. |
| 11,667,607 B1 | 6/2023 | Silverstone |
| 11,707,447 B1 | 7/2023 | Hagel et al. |
| 2004/0116410 A1 | 6/2004 | Cho et al. |
| 2008/0293695 A1 | 11/2008 | Bristol et al. |
| 2011/0111029 A1 | 5/2011 | Schmitz et al. |
| 2012/0028960 A1 | 2/2012 | King et al. |
| 2012/0108510 A1 | 5/2012 | Young et al. |
| 2014/0178480 A1 | 6/2014 | King et al. |
| 2014/0275113 A1 | 9/2014 | Wu et al. |
| 2015/0366798 A1 | 12/2015 | Lozinsky et al. |
| 2016/0303361 A1 | 10/2016 | Sameti et al. |
| 2017/0056347 A1 | 3/2017 | Glick et al. |
| 2017/0313666 A1 | 11/2017 | Wu et al. |
| 2018/0021326 A1 | 1/2018 | Stamets |
| 2018/0055791 A1 | 3/2018 | Nichols et al. |
| 2018/0343806 A1 | 12/2018 | Leo |
| 2018/0360739 A1 | 12/2018 | Lorenz et al. |
| 2019/0119310 A1 | 4/2019 | Londesbrough et al. |
| 2019/0142851 A1 | 5/2019 | Chadeayne |
| 2019/0167750 A1 | 6/2019 | Damaj |
| 2019/0246591 A1 | 8/2019 | Leo |
| 2019/0254988 A1 | 8/2019 | Archibald |
| 2020/0060997 A1 | 2/2020 | Goren et al. |
| 2020/0147038 A1 | 5/2020 | Russ et al. |
| 2020/0179349 A1 | 6/2020 | Yun et al. |
| 2020/0222656 A1 | 7/2020 | Rustick |
| 2020/0370073 A1 | 11/2020 | Leo |
| 2020/0390746 A1 | 12/2020 | Rands et al. |
| 2020/0397752 A1 | 12/2020 | Perez Castillo et al. |
| 2021/0015738 A1 | 1/2021 | Larosa et al. |
| 2021/0015833 A1 | 1/2021 | Larosa et al. |
| 2021/0236523 A1 | 8/2021 | Schindler et al. |
| 2021/0275618 A1 | 9/2021 | Davidson et al. |
| 2021/0292278 A1 | 9/2021 | Chadeayne |
| 2021/0392933 A1 | 12/2021 | Lilly |
| 2022/0007604 A1 | 1/2022 | Tudela |
| 2022/0040106 A1 | 2/2022 | Malcolm et al. |
| 2022/0054402 A1 | 2/2022 | Kaufman |
| 2022/0125091 A1 | 4/2022 | Cave et al. |
| 2022/0151993 A1 | 5/2022 | Ross et al. |
| 2022/0249591 A1 | 8/2022 | Mousset et al. |
| 2022/0296720 A1 | 9/2022 | Reed et al. |
| 2022/0323378 A1 | 10/2022 | Joseph |
| 2022/0331344 A1 | 10/2022 | Greenbaum et al. |
| 2022/0362320 A1 | 11/2022 | Ahvazi et al. |
| 2022/0370413 A1 | 11/2022 | Barrow et al. |
| 2022/0409584 A1 | 12/2022 | Bilai et al. |
| 2023/0083927 A1 | 3/2023 | Gray |
| 2023/0097076 A1 | 3/2023 | Raibar |
| 2023/0112459 A1 | 4/2023 | Anand et al. |
| 2023/0119714 A1 | 4/2023 | Londesbrough et al. |
| 2023/0138974 A1 | 5/2023 | Jeganatth |
| 2023/0202978 A1 | 6/2023 | Knight et al. |

FOREIGN PATENT DOCUMENTS

| | | |
|---|---|---|
| CN | 109350724 A | 2/2019 |
| CN | 112300050 A | 2/2021 |
| CZ | 307719 B6 | 3/2019 |
| DE | 1156077 B | 10/1963 |
| DE | 202020105085 Y1 | 11/2020 |
| EP | 1605973 A1 | 12/2005 |
| EP | 1389466 B1 | 2/2007 |
| EP | 2136844 B1 | 10/2018 |
| EP | 2768537 B1 | 2/2019 |
| EP | 2611466 B1 | 6/2019 |
| EP | 3603656 A1 | 2/2020 |
| EP | 2654864 B1 | 10/2020 |
| EP | 3277271 B1 | 7/2021 |
| EP | 3862019 A1 | 8/2021 |
| EP | 3957726 A1 | 2/2022 |
| GB | 911946 A | 12/1962 |
| GB | 912714 A | 12/1962 |
| GB | 912715 A | 12/1962 |
| GB | 2571696 B | 5/2020 |
| GB | 2572023 C | 2/2022 |
| GB | 2576059 B | 6/2022 |
| GB | 2588506 B | 7/2022 |
| GB | 2588505 A | 8/2022 |
| WO | 2000044350 A1 | 8/2000 |
| WO | 2002024865 A2 | 3/2002 |
| WO | 2002085370 A1 | 10/2002 |
| WO | 2003024481 A2 | 3/2003 |
| WO | 2003026797 A2 | 4/2003 |
| WO | 2004084939 A2 | 10/2004 |
| WO | 2005039531 A1 | 5/2005 |
| WO | 2005039546 A2 | 5/2005 |
| WO | 2006007848 A2 | 1/2006 |
| WO | 2006034343 A2 | 3/2006 |
| WO | 2007054818 A2 | 5/2007 |
| WO | 2008011051 A1 | 1/2008 |
| WO | 2008128126 A1 | 10/2008 |
| WO | 2008156707 A1 | 12/2008 |
| WO | 2009021055 A1 | 2/2009 |
| WO | 2009051837 A2 | 4/2009 |
| WO | 2009089494 A2 | 7/2009 |
| WO | 2009100384 A2 | 8/2009 |
| WO | 2009149252 A1 | 12/2009 |
| WO | 2009153019 A1 | 12/2009 |
| WO | 2010089132 A1 | 8/2010 |
| WO | 2010124089 A2 | 10/2010 |
| WO | 2010138192 A2 | 12/2010 |
| WO | 2011049954 A2 | 4/2011 |
| WO | 2011106076 A1 | 9/2011 |
| WO | 2011116189 A1 | 9/2011 |
| WO | 2011143242 A2 | 11/2011 |
| WO | 2011150240 A1 | 12/2011 |
| WO | 2012064667 A2 | 5/2012 |
| WO | 2012074588 A2 | 6/2012 |
| WO | 2012085919 A2 | 6/2012 |
| WO | 2013068949 A1 | 5/2013 |
| WO | 2013113325 A1 | 8/2013 |
| WO | 2013185032 A1 | 12/2013 |
| WO | 2014165679 A1 | 10/2014 |
| WO | 2015081166 A1 | 6/2015 |
| WO | 2014140925 A3 | 7/2015 |
| WO | 2015168022 A1 | 11/2015 |
| WO | 2016001921 A2 | 1/2016 |
| WO | 2017013031 A1 | 1/2017 |

(56) References Cited

FOREIGN PATENT DOCUMENTS

| | | |
|---|---|---|
| WO | 2017141104 A2 | 8/2017 |
| WO | 2018022664 A1 | 2/2018 |
| WO | 2018025089 A2 | 2/2018 |
| WO | 2018135943 A1 | 7/2018 |
| WO | 2018141063 A1 | 8/2018 |
| WO | 2018148605 A1 | 8/2018 |
| WO | 2018170596 A1 | 9/2018 |
| WO | 2018183115 A1 | 10/2018 |
| WO | 2018195455 A1 | 10/2018 |
| WO | 2018200959 A1 | 11/2018 |
| WO | 2018209341 A1 | 11/2018 |
| WO | 2019025763 A1 | 2/2019 |
| WO | 2019064031 A1 | 4/2019 |
| WO | 2019071213 A1 | 4/2019 |
| WO | 2019073379 A1 | 4/2019 |
| WO | 2019079742 A1 | 4/2019 |
| WO | 2019081764 A1 | 5/2019 |
| WO | 2019092569 A1 | 5/2019 |
| WO | 2019109124 A1 | 6/2019 |
| WO | 2019122525 A1 | 6/2019 |
| WO | 2019140403 A1 | 7/2019 |
| WO | 2019144140 A1 | 7/2019 |
| WO | 2019161050 A1 | 8/2019 |
| WO | 2019161231 A1 | 8/2019 |
| WO | 2019173797 A1 | 9/2019 |
| WO | 2019175290 A1 | 9/2019 |
| WO | 2019178360 A1 | 9/2019 |
| WO | 2019180309 A1 | 9/2019 |
| WO | 2019195813 A1 | 10/2019 |
| WO | 2019200482 A1 | 10/2019 |
| WO | 2019207319 A1 | 10/2019 |
| WO | 2019246532 A2 | 12/2019 |
| WO | 2020023084 A1 | 1/2020 |
| WO | 2020041329 A1 | 2/2020 |
| WO | 2020097320 A1 | 5/2020 |
| WO | 2020142259 A1 | 7/2020 |
| WO | 2020157569 A1 | 8/2020 |
| WO | 2020169850 A1 | 8/2020 |
| WO | 2020169851 A1 | 8/2020 |
| WO | 2020176599 A1 | 9/2020 |
| WO | 2020181194 A1 | 9/2020 |
| WO | 2020185581 A2 | 9/2020 |
| WO | 2020185711 A1 | 9/2020 |
| WO | 2020185712 A1 | 9/2020 |
| WO | 2020212948 A | 10/2020 |
| WO | 2020212948 A1 | 10/2020 |
| WO | 2020212951 A1 | 10/2020 |
| WO | 2020212952 A1 | 10/2020 |
| WO | 2020241958 A1 | 12/2020 |
| WO | 2020245133 A1 | 12/2020 |
| WO | 2020263941 A1 | 12/2020 |
| WO | 2021003467 A1 | 1/2021 |
| WO | 2021016423 A1 | 1/2021 |
| WO | 2021005310 A1 | 2/2021 |
| WO | 2021016710 A1 | 2/2021 |
| WO | 2021019023 A1 | 2/2021 |
| WO | 2021030571 A1 | 2/2021 |
| WO | 2021041407 A1 | 3/2021 |
| WO | 2021052989 A1 | 3/2021 |
| WO | 2021067626 A2 | 4/2021 |
| WO | 2021067961 A1 | 4/2021 |
| WO | 2021072530 A1 | 4/2021 |
| WO | 2021074448 A1 | 4/2021 |
| WO | 2021076849 A1 | 4/2021 |
| WO | 2021081138 A1 | 4/2021 |
| WO | 2021086513 A1 | 5/2021 |
| WO | 2021089872 A1 | 5/2021 |
| WO | 2021092515 A1 | 5/2021 |
| WO | 2021097452 A2 | 5/2021 |
| WO | 2021101926 A1 | 5/2021 |
| WO | 2021108911 A1 | 6/2021 |
| WO | 2021113986 A1 | 6/2021 |
| WO | 2021116503 A2 | 6/2021 |
| WO | 2021138564 A1 | 7/2021 |
| WO | 2021139874 A1 | 7/2021 |
| WO | 2021155467 A1 | 8/2021 |
| WO | 2021155468 A1 | 8/2021 |
| WO | 2021158888 A1 | 8/2021 |
| WO | 2021159213 A1 | 8/2021 |
| WO | 2021168082 A1 | 8/2021 |
| WO | 2021173273 A1 | 9/2021 |
| WO | 2021173989 A1 | 9/2021 |
| WO | 2021178579 A1 | 9/2021 |
| WO | 2021179091 A1 | 9/2021 |
| WO | 2021183490 A2 | 9/2021 |
| WO | 2021188782 A1 | 9/2021 |
| WO | 2021188812 A1 | 9/2021 |
| WO | 2021188870 A1 | 9/2021 |
| WO | 2021194796 A1 | 9/2021 |
| WO | 2021202730 A1 | 10/2021 |
| WO | 2021207137 A1 | 10/2021 |
| WO | 2021207824 A1 | 10/2021 |
| WO | 2021209815 A1 | 10/2021 |
| WO | 2021211358 A1 | 10/2021 |
| WO | 2021216489 A1 | 10/2021 |
| WO | 2021-226416 A1 | 11/2021 |
| WO | 2021222885 A1 | 11/2021 |
| WO | 2021225796 A1 | 11/2021 |
| WO | 2021226041 A1 | 11/2021 |
| WO | 2021226542 A1 | 11/2021 |
| WO | 2021236759 A2 | 11/2021 |
| WO | 2021243460 A1 | 12/2021 |
| WO | 2021243461 A1 | 12/2021 |
| WO | 2021248087 A2 | 12/2021 |
| WO | 2021250434 A1 | 12/2021 |
| WO | 2021252538 A2 | 12/2021 |
| WO | 2021253116 A1 | 12/2021 |
| WO | 2021257586 A1 | 12/2021 |
| WO | 2021262871 A1 | 12/2021 |
| WO | 2022000091 A1 | 1/2022 |
| WO | 2022010937 A1 | 1/2022 |
| WO | 2022011350 A1 | 1/2022 |
| WO | 2022016289 A1 | 1/2022 |
| WO | 2022018709 A1 | 1/2022 |
| WO | 2022023812 A1 | 2/2022 |
| WO | 2022031551 A1 | 2/2022 |
| WO | 2022031552 A1 | 2/2022 |
| WO | 2022031566 A1 | 2/2022 |
| WO | 2022031907 A1 | 2/2022 |
| WO | 2022032147 A1 | 2/2022 |
| WO | 2022038170 A1 | 2/2022 |
| WO | 2022038299 A1 | 2/2022 |
| WO | 2022040802 A1 | 3/2022 |
| WO | 2022043227 A1 | 3/2022 |
| WO | 2022047579 A1 | 3/2022 |
| WO | 2022047580 A1 | 3/2022 |
| WO | 2022047583 A1 | 3/2022 |
| WO | 2022049574 A | 3/2022 |
| WO | 2022051578 A1 | 3/2022 |
| WO | 2022051670 A1 | 3/2022 |
| WO | 2022053892 A2 | 3/2022 |
| WO | 2022061196 A1 | 3/2022 |
| WO | 2022061242 A1 | 3/2022 |
| WO | 2022069690 A2 | 4/2022 |
| WO | 2022072808 A1 | 4/2022 |
| WO | 2022079574 A1 | 4/2022 |
| WO | 2022081549 A1 | 4/2022 |
| WO | 2022084480 A1 | 4/2022 |
| WO | 2022094054 A1 | 5/2022 |
| WO | 2022094719 A1 | 5/2022 |
| WO | 2022104475 A1 | 5/2022 |
| WO | 2022106947 A1 | 5/2022 |
| WO | 2022115796 A1 | 6/2022 |
| WO | 2022115798 A2 | 6/2022 |
| WO | 2022115944 A1 | 6/2022 |
| WO | 2022115960 | 6/2022 |
| WO | 2022120181 A1 | 6/2022 |
| WO | 2022120289 A1 | 6/2022 |
| WO | 2022120475 A1 | 6/2022 |
| WO | 2022123232 A1 | 6/2022 |
| WO | 2022125616 A1 | 6/2022 |
| WO | 2022125949 A1 | 6/2022 |
| WO | 2022132691 A1 | 6/2022 |
| WO | 2022137107 A1 | 6/2022 |

(56) References Cited

FOREIGN PATENT DOCUMENTS

| | | |
|---|---|---|
| WO | 2022140841 A1 | 7/2022 |
| WO | 2022150530 A1 | 7/2022 |
| WO | 2022150563 A1 | 7/2022 |
| WO | 2022150675 A1 | 7/2022 |
| WO | 2022150840 A1 | 7/2022 |
| WO | 2022150854 A1 | 7/2022 |
| WO | 2022155284 A1 | 7/2022 |
| WO | 2022155352 A1 | 7/2022 |
| WO | 2022155591 A1 | 7/2022 |
| WO | 2022155751 A1 | 7/2022 |
| WO | 2022165387 A1 | 8/2022 |
| WO | 2022170438 A1 | 8/2022 |
| WO | 2022170442 A2 | 8/2022 |
| WO | 2022173584 A1 | 8/2022 |
| WO | 2022173888 A1 | 8/2022 |
| WO | 2022175821 A1 | 8/2022 |
| WO | 2022177716 A1 | 8/2022 |
| WO | 2022182527 A1 | 9/2022 |
| WO | 2022183292 A1 | 9/2022 |
| WO | 2022187973 A1 | 9/2022 |
| WO | 2022189855 A1 | 9/2022 |
| WO | 2022192097 A1 | 9/2022 |
| WO | 2022192215 A1 | 9/2022 |
| WO | 2022195011 A1 | 9/2022 |
| WO | 2022195489 A2 | 9/2022 |
| WO | 2022204802 A2 | 10/2022 |
| WO | 2022207746 A1 | 10/2022 |
| WO | 2022212585 A1 | 10/2022 |
| WO | 2022212789 A1 | 10/2022 |
| WO | 2022212854 A1 | 10/2022 |
| WO | 2022221554 A2 | 10/2022 |
| WO | 2022221942 A1 | 10/2022 |
| WO | 2022226493 A1 | 10/2022 |
| WO | 2022232933 A1 | 11/2022 |
| WO | 2022235500 A1 | 11/2022 |
| WO | 2022235514 A1 | 11/2022 |
| WO | 2022235529 A1 | 11/2022 |
| WO | 2022235531 A1 | 11/2022 |
| WO | 2022235912 A1 | 11/2022 |
| WO | 2022236130 A1 | 11/2022 |
| WO | 2022236407 A1 | 11/2022 |
| WO | 2022240853 A1 | 11/2022 |
| WO | 2022243285 A1 | 11/2022 |
| WO | 2022246572 A1 | 12/2022 |
| WO | 2022248635 A2 | 12/2022 |
| WO | 2022251169 A1 | 12/2022 |
| WO | 2022251699 A1 | 12/2022 |
| WO | 2022256720 A2 | 12/2022 |
| WO | 2022259046 A1 | 12/2022 |
| WO | 2022261058 A1 | 12/2022 |
| WO | 2022261263 A1 | 12/2022 |
| WO | 2022261761 A1 | 12/2022 |
| WO | 2022265878 A1 | 12/2022 |
| WO | 2022269264 A1 | 12/2022 |
| WO | 2022269265 A1 | 12/2022 |
| WO | 2022269266 A1 | 12/2022 |
| WO | 2022269267 A1 | 12/2022 |
| WO | 2022271841 A1 | 12/2022 |
| WO | 2022272176 A1 | 12/2022 |
| WO | 2023278131 A1 | 1/2023 |
| WO | 2023278403 A2 | 1/2023 |
| WO | 2023283386 A2 | 1/2023 |
| WO | 2023287283 A1 | 1/2023 |
| WO | 2023010203 A1 | 2/2023 |
| WO | 2023012524 A2 | 2/2023 |
| WO | 2023012691 A1 | 2/2023 |
| WO | 2023023347 A1 | 2/2023 |
| WO | 2023023857 A1 | 3/2023 |
| WO | 2023028086 A1 | 3/2023 |
| WO | 2023043794 A1 | 3/2023 |
| WO | 2023043826 A1 | 3/2023 |
| WO | 2023044135 A1 | 3/2023 |
| WO | 2023044169 A2 | 3/2023 |
| WO | 2023044556 A1 | 3/2023 |
| WO | 2023044577 A1 | 3/2023 |
| WO | 2023053090 A1 | 4/2023 |
| WO | 2023055860 A1 | 4/2023 |
| WO | 2023055992 A1 | 4/2023 |
| WO | 2023056561 A1 | 4/2023 |
| WO | 2023060302 A1 | 4/2023 |
| WO | 2023064840 A1 | 4/2023 |
| WO | 2023065012 A1 | 4/2023 |
| WO | 2023067509 A1 | 4/2023 |
| WO | 2023077234 A1 | 5/2023 |
| WO | 2023077245 A1 | 5/2023 |
| WO | 2023081109 A1 | 5/2023 |
| WO | 2023081829 A2 | 5/2023 |
| WO | 2023081833 A1 | 5/2023 |
| WO | 2023081837 A2 | 5/2023 |
| WO | 2023081842 A2 | 5/2023 |
| WO | 2023081892 A1 | 5/2023 |
| WO | 2023086252 A1 | 5/2023 |
| WO | 2023086962 A1 | 5/2023 |
| WO | 2023091717 A1 | 5/2023 |
| WO | 2023091721 A1 | 5/2023 |
| WO | 2023108164 A2 | 6/2023 |
| WO | 2023108167 A1 | 6/2023 |
| WO | 2023108260 A1 | 6/2023 |
| WO | 2023108277 A1 | 6/2023 |
| WO | 2023114097 A1 | 6/2023 |
| WO | 2023114529 A2 | 6/2023 |
| WO | 2023115060 A1 | 6/2023 |
| WO | 2023122320 A1 | 6/2023 |
| WO | 2023130075 A2 | 7/2023 |
| WO | 2023130191 A1 | 7/2023 |
| WO | 2023135595 A1 | 7/2023 |
| WO | 2023137094 A1 | 7/2023 |
| WO | 2023137325 A1 | 7/2023 |
| WO | 2023146579 A1 | 8/2023 |

OTHER PUBLICATIONS

Liu et al. Parkinsonism Caused by Viral Encephalitis Affecting the Bilateral Substantia Nigra., Clinical Neurology, 2019, 29:571-573 (Year: 2019).*
Jicha et al. (Hippocampal Sclerosis . . . , American Academy of Neurology, 2019, p. 208-233 (Year: 2019).*
Teylan et al., Clinical diagnoses, Laboratory investigation, 2019, 99:1049-1055 (Year: 2019).*
Bauer. The Pharmacology of Psilocybin and Psilocin, Psychedelic Science Review, 2019, p. 1-6 (Year: 2019).*
Yan et al. Crystal Structures, Stability, and Solubility Evaluation, Cryst. Growth Des., 2020, p. 1079-1087 (Year: 2020).*
Cambridge MedChem Consulting. Bioisosteric Replacements, CMC, 2021, p. 1-9 (Year: 2021).*
Harvard Health Publishing. What Causes Depression?, Harvard Medical School, 2022, p. 1-10 (Year: 2022).*
Abramov et al., "Rational Coformer or Solvent Selection for Pharmaceutical Cocrystallization or Desolvation", Journal of Pharmaceutical Sciences, vol. 101, Oct. 2012, pp. 3687-3697.
Allen, "The Cambridge Structural Database: A Quarter of a Million Crystal Structures and Rising", Acta. Crystallogr. Section B, vol. 58, 2002, pp. 380-388.
Alvarez et al., "Polymorph Screening: Comparing a Semi-Automated Approach with a High Throughput Method", Crystal Growth and Design, vol. 9, 2009, pp. 4181-4188.
Anderson et al., "Occurrence and Use of Hallucinogenic Mushrooms Containing Psilocybin Alkaloids", Nordic Council of Ministers, Copenhagen, 2009, 124 pages.
Baker et al., "Molecular Structures of Hallucinogenic Substances: Lysergic Acid Diethylamide, Psilocybin, and 2,4,5-Trimethoxyamphetamine", Molecular Pharmacology, 1973, vol. 9, pp. 23-32.
Beck et al., "An Inventory for Measuring Depression", Archives of General Psychiatry, vol. 4, Jun. 1961, 11 Pages.
Becke, "Density-Functional Exchange-Energy Approximation With Correct Asymptotic Behavior", The American Physical Society, vol. 38, No. 6, Sep. 15, 1988, pp. 3098-3100.
Breeksema et al., "Treatment With Psilocybin: Applications for Patients With Psychiatric Disorders", Nederlands Tijdschrift voor

(56) References Cited

OTHER PUBLICATIONS

Geneeskunde; vol. 165; No. 4; Jan. 25, 2021, 2 pages (Reaxys database extract, database accession No. XRN=37140626).
Cashman et al., "A Specific Microcrystalline Test for Indolamine Derivatives", Michrochemical Journal, vol. 20, 1975, pp. 511-518.
Datta et al., "Crystal Structures of Drugs: Advances in Determination, Prediction and Engineering", Nature, vol. 3, Jan. 2004, pp. 42-57.
Greenan et al., "Preparation and Characterization of Novel Crystalline Solvates and Polymorphs of Psilocybin and Identification of Solid Forms Suitable for Clinical Development", 2020, 29 pages (https://www.researchgate.net/publication/339238710_Preparation_and_Characterization_of_Novel_Crystalline_Solvates_and_Polymorphs_of_Psilocybin_and_Identification_of_Solid_Forms_Suitable_for_Clinical_Development).
Hofmann, et al., "Psilocybin, a Psychotropic Agent From the Mexican Intoxicating Mushroom *Psilocybe mexicana* Home", Exerientia, vol. 14, 1958, pp. 107-109 (with machine English translation).
Hofmann, "Psychotomimetic Drugs Chemical and Pharmacological Aspects", Acta Physiol. Pharmacol. Neerlandica, vol. 8, 1959, pp. 240-258.
Jones et al., "Pharmaceutical Cocrystals: An Emerging Approach to Physical Property Enhancement", MRS Bulletin, vol. 31, Nov. 2006, pp. 875-879.
Kang et al., "Theoretical Studies on the Conformations of Psilocin and Mescaline", Molecular Pharmacology, vol. 9, 9 pp. 640-648.
Kargbo et al., "Direct Phosphorylation of Psilocin Enables Optimized cGMP Kilogram-Scale Manufacture of Psilocybin", ACS Omega, 2020, vol. 5, pp. 16959-16966.
Kissane et al., "The Demoralization Scale: A Report of Its Development and Preliminary Validation", Journal of Palliative Care, vol. 20, No. 4, pp. 269-276.
Kuhnert-Brandstatter et al., "Polymorphic modifications and solvates of psilocin and psilocybin", Arch Pharm., vol. 309, No. 76, 1976 (with machine English translation) pp. 625-631.
Liaw et al., "Classification and Regression by RandomForest", M. R. News, vol. 2, No. 3, Dec. 2022, pp. 18-22.
Loschen et al., "Solubility Prediction, Solvate and Cocrystal Screening as Tools for Rational Crystal Engineering: Solubility Prediction, Solvate and Cocrystal Screening", Journal of Pharmacy and Pharmacology, vol. 67, Jun. 2015, pp. 803-811.
Loschen et al., "New Developments In Prediction of Solid-state Solubility and Cocrystallization Using Cosmo-rs Theory", Computational Pharmaceutical Solid State Chemistry, 2016, pp. 211-234.
McNamara et al., "Use of a Glutaric Acid Cocrystal to Improve Oral Bioavailability of a Low Solubility API", Pharmaceutical Research, vol. 23, No. 8, Aug. 2006, 11 pages.
Meltzer et al., "Stimulation of Rat Prolactin Secretion by Indolealkylamine Hallucinogens", Psychopharmacology, vol. 56, 1978, pp. 255-259.
Migliaccio et al., "Comparison of Solution Conformational Preferences for the Hallucinogens Bufotenin and Psilocin Using 360-MHz Proton NMR Spectroscopy", J. Med. Chem., vol. 24, 1981, pp. 206-209.
Nichols et al., "Improvements to the Synthesis of Psilocybin and a Facile Method for Preparing the O-Acetyl Prodrug of Psilocin", Synthesis, No. 6, 1999, pp. 935-938.
Ono et al., "Studies on Hallucinogens. V Synthesis of Psilocybin", Bulletin of National Institute of Hygienic Sciences, vol. 92, 1974, pp. 41-43 (with machine English Translation).
Perdew, "Density-Functional Approximation for The Correlation Energy of The Inhomogeneous Electron Gas", Physical Review B, vol. 33, No. 12, Jun. 15, 1986, pp. 8822-8824.
Perdew, "Erratum: Density-Functional Approximation for The Correlation Energy of The Inhomogeneous Electron Gas", Physical Review B, vol. 34, No. 10, Nov. 15, 1986, p. 7406.
Petcher et al., "Crystal Structures of the Teonanácatl Hallucinogens. Part II. Psilocin, C12 H15N20", J. Chem. Soc., Perkin Trans., 1974, pp. 946-948.
Rager et al., "Cocrystal Formation from Solvent Mixtures", Crystal Growth & Design, vol. 10, No. 7, 2010, pp. 3237-3241.
Repke et al., "Psilocin Analogs 11. Synthesis of 3-[2-(Dialkylamino)ethyl]-, 3-[2-(N-Methyl-N-alkylamino)ethyl]-, and 3-[2-(Cycloalkylamino)ethyl]indol-4-ols", Journal of Hetrocyclic Chemistry, vol. 18, No. 185, Jan. 1981, pp. 175-179.
RodríGuez-Spong et al., "General Principles of Pharmaceutical Solid Polymorphism: A Supramolecular Perspective", Advanced Drug Delivery Reviews, vol. 56, 2004, pp. 241-274.
Rosenfeld et al., "Assessing Hopelessness in Terminally Ill Cancer Patients: Development of the Hopelessness Assessment in Illness Questionnaire", Psychol Assess, vol. 23, No. 2, Jun. 2011, pp. 325-336.
Schäfer et al., "Fully optimized contracted Gaussian basis sets of triple zeta valence quality for atoms Li to Kr", J. Chem. Phys., vol. 100, No. 8, Apr. 15, 1994, pp. 5829-5835.
Schultheiss et al., "Pharmaceutical Cocrystals and Their Physicochemical Properties", Crystal Growth & Design, vol. 9, No. 6, 2009, pp. 2950-2967.
Stahl et al., "Monographs on Acids and Bases", Handbook of Pharmaceutical Salts Properties, Selection, and Use, 2002, pp. 329-335.
Stahl et al., "Appendix", Handbook of Pharmaceutical Salts Properties, Selection, and Use, 2002, pp. 265-327.
Stahl et al., "Handbook of Pharmaceutical Salts Properties, Selection, and Use", 2008, pp. 103-170.
Steinbeck et al., "Recent Developments of the Chemistry Development Kit (CDK)—An Open-Source Java Library for Chemo- and Bioinformatics", J. Chem. Inf. Comput. Sci. Curr Pharm Des., vol. 12, No. 17, 2006, pp. 2110-2120.
Stockwatch Business Reporter, "Shell Summary for Jan. 7, 2021", Stockwatch Daily, Jan. 8, 2021, 3 pages.
Szegezdi et al., "Prediction of Dissociation Constant Using Microconstants", American Chemical Society National Meeting, Mar. 28-Apr. 1, 2001, updaed Apr. 15, 2004, 2 pages.
Templer, "The Construction and Validation of a Death Anxiety Scale" The Journal of General Psychology, 1970, vol. 82, No. 2, pp. 165-177.
Troxler et al., "Modification products of psilocybin and psilocin", Communication on Synthetic Indole Compounds, vol. XLII, File VI, No. 226, 1959, pp. 2073-2103 (with machine English translation).
Weber et al., "Crystal Structures of the Teonanácatl Hallucinogens. Part 1. Psilocybin C12H17N2O4P", J. C. S. Perkin II, Jan. 1, 1974, pp. 942-946.
Zigmond et al., "The Hospital Anxiety and Depression Scale", Acta. Psychiatr. Scand., vol. 67, 1983, pp. 361-370.
Eberhard, Michael, International Search Report and Written Opinion dated May 25, 2023 for corresponding International Application No. PCT/US2023/014417, 11 pages.
Beck, "Psychometric Properties of the Beck Depression Inventory: Twenty-Five Ye Ars of Evaluation ", Clinical Psychology Review, 1988, vol. 8, pp. 77-100.
Sherwood et al., "An Improved, Practical, and Scalable Five-Step Synthesis of Psilocybin", Synthesis, 2020, vol. 52, pp. 688-694.
Adwas et al., "Anxiety: Insights into Signs, Symptoms, Etiology, Pathophysiology, and Treatment", Oct. 2019, East African Scholars Journal of Medical Sciences, vol. 2, pp. 580-591.
Bains et al., "Major Depressive Disorder", 2023, StatPearls, pp. 1-7.
Pohanka, "D-Lactic Acid as a Metabolite: Toxicology, Diagnosis, and Detection", 2020, Biomed Research International, vol. 2020, pp. 1-9.

\* cited by examiner

CO-CRYSTALS OR SALTS OF PSILOCYBIN AND METHODS OF TREATMENT THEREWITH

CROSS-REFERENCE TO RELATED APPLICATIONS

This application claims the benefit of, and relies on the filing date of, U.S. Provisional Patent Application No. 63/316,612, filed 4 Mar. 2022, U.S. Provisional Patent Application No. 63/316,621, filed 4 Mar. 2022, U.S. Provisional Patent Application No. 63/316,627, filed 4 Mar. 2022, U.S. Provisional Patent Application No. 63/322,697, filed 23 Mar. 2022, U.S. Provisional Patent Application No. 63/322,701, filed 23 Mar. 2022, and U.S. Provisional Patent Application No. 63/322,703, filed 23 Mar. 2022, the entire disclosures of which are hereby incorporated by reference in their entirety.

FIELD OF THE INVENTION

The present invention relates to co-crystals or salts comprising psilocybin. Methods of treating and preventing conditions using the co-crystals or salts are also described.

BACKGROUND OF THE INVENTION

Psilocybin (4-phosphoryloxy-N,N-dimethyltryptamine) is a tryptamine serotoninergic psychedelic. The IUPAC name of psilocybin is [3-(2-dimethylaminoethyl)-1H-indol-4-yl]dihydrogen phosphate. The structure of psilocybin is shown below.

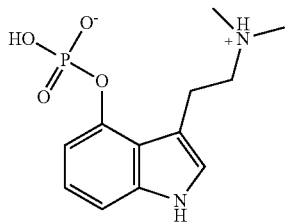

The $pK_a$ values of psilocybin are reported to be $pK_a1=1.3$ ($1^{st}$ phosphate oxygen); $pK_a2=6.5$ ($2^{nd}$ phosphate oxygen); $pK_a3=10.4$ (tertiary amine) (estimated) and given these values, psilocybin is often referred to as a permanent zwitterion.

Pharmaceutical compounds may exist in a number of different solid forms. This includes crystalline forms, salts, hydrates and solvates, and amorphous phases. Different solid forms of a pharmaceutical compound have different properties, for instance in relation to crystallinity, chemical and physical stability, and processability.

Psilocybin is currently being investigated as a potential treatment for various psychiatric disorders (for example, demoralization, depression, anxiety and adjustment disorders) in a variety of clinical settings. There is accordingly a need to develop new forms of psilocybin with particularly advantageous properties for use in such treatments.

SUMMARY OF THE INVENTION

It is a finding of the invention that a co-crystal comprising psilocybin and a co-former provides a crystalline form with favourable properties such as high crystallinity and/or beneficial morphology. The co-crystal also has good physical and chemical stability, as well as suitability for secondary processing (including improved flowability and compaction). The use of the co-crystal may also provide modulation of the dissolution rate and kinetic solubility, which can be useful in pharmaceutical settings.

In particular, the inventors have found that co-crystals or salts of psilocybin formed with a co-former selected from benzylamine, diethylaminoethanol, 4-(2-hydroxyethyl)-morpholine, 1-(2-hydroxyethyl) pyrrolidine, deanol, piperazine, pyridoxine, tert-butylamine, urea and propyl gallate are well suited to pharmaceutical formulation.

The present invention accordingly provides a co-crystal comprising psilocybin and a co-former, wherein the co-former is selected from piperazine, benzylamine, diethylaminoethanol, 4-(2-hydroxyethyl)-morpholine, 1-(2-hydroxyethyl) pyrrolidine, deanol, pyridoxine, tert-butylamine, urea and propyl gallate. The invention alternatively provides a salt comprising psilocybin and a co-former, wherein the co-former is selected from piperazine, benzylamine, diethylaminoethanol, 4-(2-hydroxyethyl)-morpholine, 1-(2-hydroxyethyl) pyrrolidine, deanol, pyridoxine, tert-butylamine, urea and propyl gallate.

The invention further provides a pharmaceutical composition comprising a co-crystal or salt as described herein; and a pharmaceutically acceptable excipient or diluent. The invention also provides a method of treating or preventing a disease or condition selected from psychological, neurological and central nervous system disorders in a patient, the method comprising administering a therapeutically effective amount of a co-crystal or salt as described herein to the patient.

Also provided by the invention is a kit comprising a co-crystal, salt or a pharmaceutical composition as described herein; and instructions for use of the co-crystal, salt or pharmaceutical composition in a method of treating or preventing a disease or condition as described herein.

DETAILED DESCRIPTION OF THE INVENTION

Figure 1:
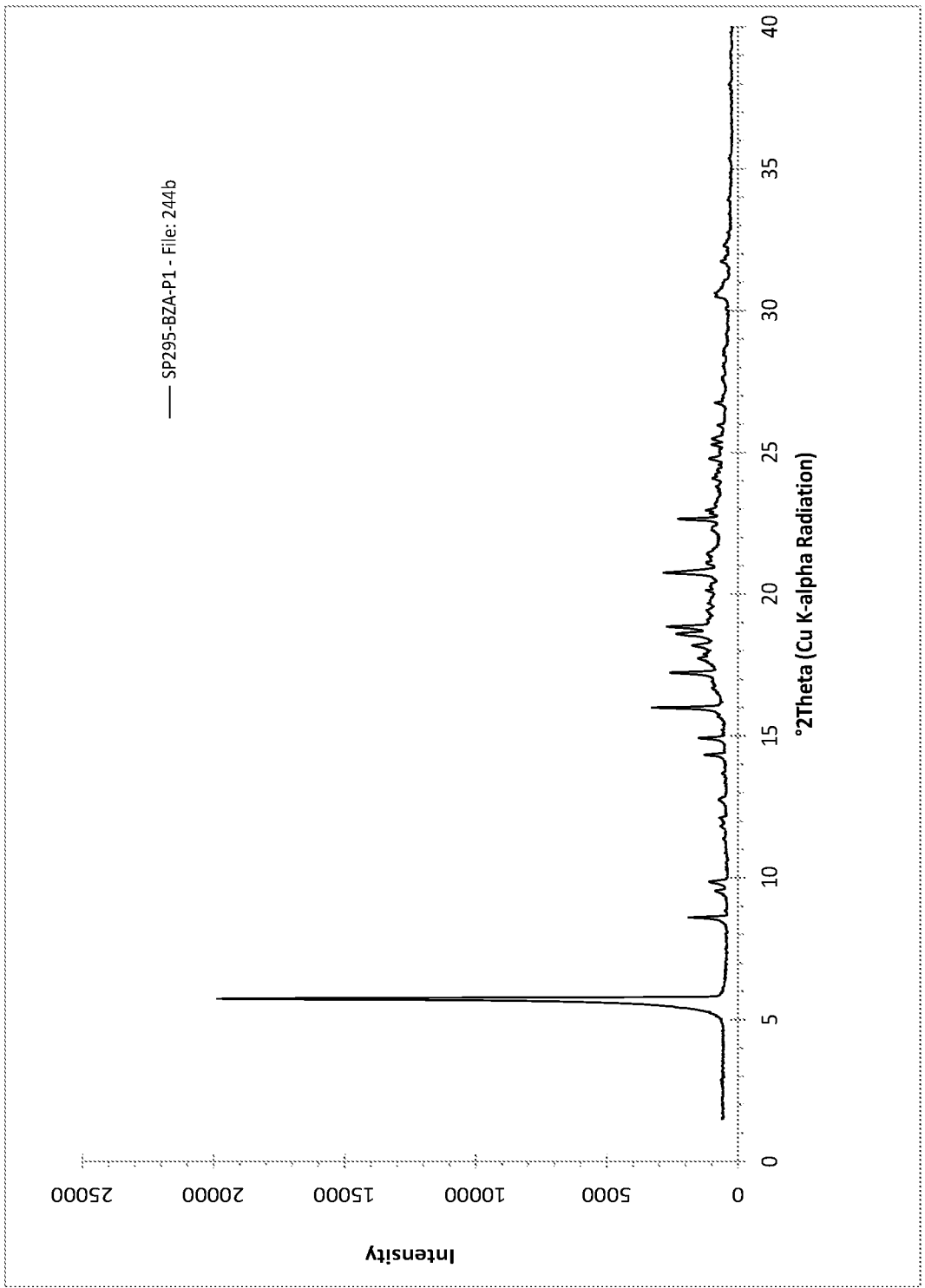
FIG. 1 shows the XRPD 2θ diffractogram of Pattern 1 of a co-crystal comprising psilocybin and benzylamine.

The co-crystal according to the invention comprises psilocybin and a co-former.

A co-crystal is a solid crystalline material comprising two or more different molecular and/or ionic compounds, for instance an active agent and a co-former. The active agent and the co-former are in the same crystal lattice. A co-crystal is typically neither a solvate nor a simple salt, although a co-crystal may additionally be hydrated or solvated (i.e. it may comprise the active agent, the co-former and water or solvent molecules) or one of the components in the co-crystal (e.g. the co-former) may itself be a salt.

A co-crystal may comprise an active agent and a co-former. The active agent and co-former are typically arranged in a regular repeating crystal structure. A co-crystal has a different crystal structure to that of either the active agent or co-former alone.

The co-crystal may consist essentially of psilocybin and the co-former and, optionally, water or a solvent. If the co-crystal comprises a co-former and one or more additional co-formers, the co-crystal may consist essentially of psilocybin and the co-formers and, optionally water or a solvent. The co-crystal may comprise at least 90% by weight, at least 95% by weight or at least 99% by weight of psilocybin, the co-former(s) and optionally water or a solvent. The co-crystal may consist essentially of psilocybin and the co-former(s). The co-crystal may comprise at least 90% by weight, at least 95% by weight or at least 99% by weight of psilocybin and the co-former(s). The co-crystal may consist of psilocybin and the co-former(s). The term "consist essentially of" as used here means that the co-crystal contains only the specified components (i.e. psilocybin, the co-former(s) and, optionally, water or a solvent) and any additional component which does not materially affect the essential characteristics or function of the specified components.

The co-former is typically selected from piperazine, benzylamine, diethylaminoethanol, 4-(2-hydroxyethyl)-morpholine, 1-(2-hydroxyethyl) pyrrolidine, deanol, pyridoxine, tert-butylamine, urea and propyl gallate. Preferably, the co-former is selected from piperazine, deanol, pyridoxine, and tert-butylamine. More preferably, the co-former is piperazine.

In one embodiment, the co-crystal is a co-crystal comprising psilocybin and piperazine, wherein the molar ratio of psilocybin:piperazine is about 1:0.5. The molar ratio may be 1:0.5. Alternatively, the molar ratio may be about 1:1, 1:1.5, or 1:2.

In one embodiment, the co-crystal is a co-crystal comprising psilocybin and benzylamine, wherein the molar ratio of psilocybin:benzylamine is about 1:1. The molar ratio may be 1:1. Alternatively, the molar ratio may be about 1:0.5, 1:1.5, or 1:2.

In one embodiment, the co-crystal is a co-crystal comprising psilocybin and diethylaminoethanol, wherein the molar ratio of psilocybin:diethylaminoethanol is about 1:1.5. The molar ratio may be 1:1.5. Alternatively, the molar ratio may be about 1:0.5, 1:1, or 1:2.

In one embodiment, the co-crystal is a co-crystal comprising psilocybin and 4-(2-hydroxyethyl)-morpholine, wherein the molar ratio of psilocybin:4-(2-hydroxyethyl)-morpholine is about 1:1. The molar ratio may be 1:1. Alternatively, the molar ratio may be about 1:0.5, 1:1.5, or 1:2.

In one embodiment, the co-crystal is a co-crystal comprising psilocybin and 1-(2-hydroxyethyl) pyrrolidine, wherein the molar ratio of psilocybin:1-(2-hydroxyethyl) pyrrolidine is about 1:1. The molar ratio may be 1:1. Alternatively, the molar ratio may be about 1:0.5, 1:1.5, or 1:2.

In one embodiment, the co-crystal is a co-crystal comprising psilocybin and deanol, wherein the molar ratio of psilocybin:deanol is about 1:1. The molar ratio may be 1:1. In an alternative embodiment, the co-crystal is a co-crystal comprising psilocybin and deanol, wherein the molar ratio of psilocybin:deanol is about 1:6. The molar ratio may be 1:6. Alternatively, the molar ratio may be about 1:0.5, 1:1.5, or 1:2.

In one embodiment, the co-crystal is a co-crystal comprising psilocybin and pyridoxine, wherein the molar ratio of psilocybin:pyridoxine is about 1:1. The molar ratio may be 1:1. Alternatively, the molar ratio may be about 1:0.5, 1:1.5, or 1:2.

In one embodiment, the co-crystal is a co-crystal comprising psilocybin and tert-butylamine, wherein the molar ratio of psilocybin:tert-butylamine is about 1:1. The molar ratio may be 1:1. Alternatively, the molar ratio may be about 1:0.5, 1:1.5, or 1:2.

In one embodiment, the co-crystal is a co-crystal comprising psilocybin and urea, wherein the molar ratio of psilocybin:urea is about 1:1. The molar ratio may be 1:1. Alternatively, the molar ratio may be about 1:0.5, 1:1.5, or 1:2.

In one embodiment, the co-crystal is a co-crystal comprising psilocybin and propyl gallate, wherein the molar ratio of psilocybin:propyl gallate is about 1:1.5. The molar ratio may be 1:1.5. Alternatively, the molar ratio may about 1:0.5, 1:1 or 1:2.

As stated herein, values of ° 2θ are as measured using an x-ray wavelength of CuK α1 radiation (Δ=1.54060 Å). If an x-ray powder diffraction pattern comprises a peak, the relative intensity of that peak is typically at least 5% or at least 10%. Error margins for the values of ° 2θ are typically ±0.2° 2θ, but the error margin may alternatively be ±0.1° 2θ.

The co-crystal comprising psilocybin and benzylamine may be in the form of the crystalline form designated as Pattern 1. Pattern 1 of the co-crystal comprising psilocybin and benzylamine typically has an x-ray powder diffraction (XRPD) pattern comprising peaks at 5.7°, 16.0° and 20.8°±0.2° 2θ.

The XRPD pattern of Pattern 1 of the co-crystal comprising psilocybin and benzylamine typically further comprises one or more peaks selected from 17.2°, 18.6°, 18.9°, and 22.7°±0.2° 2θ. Pattern 1 of the co-crystal comprising psilocybin and benzylamine may further comprise peaks at 17.2°, 18.6°, 18.9°, and 22.7°±0.2° 2θ.

The XRPD pattern of Pattern 1 of the co-crystal comprising psilocybin and benzylamine may comprise five or more peaks selected from 5.7°, 8.6°, 16.0°, 17.2°, 18.2°, 18.6°, 18.9°, 20.8° and 22.7°±0.2° 2θ. The XRPD pattern may comprise seven or more of these peaks. The XRPD pattern may comprise all of these peaks. The XRPD pattern of Pattern 1 of the co-crystal comprising psilocybin and benzylamine may comprise the following peaks.

| Pattern 1 of the co-crystal of psilocybin and benzylamine | |
|---|---|
| Angle [°2θ] | Rel. Intensity [%] |
| 5.7 | 100 |
| 8.6 | 11 |
| 9.8 | 7 |
| 14.3 | 8 |
| 14.9 | 9 |
| 16.0 | 20 |
| 17.2 | 15 |
| 17.7 | 9 |
| 18.2 | 10 |
| 18.6 | 14 |
| 18.9 | 16 |
| 19.4 | 7 |
| 19.7 | 7 |
| 20.2 | 7 |
| 20.8 | 17 |
| 21.1 | 7 |
| 21.4 | 7 |
| 22.7 | 14 |
| 22.9 | 7 |
| 24.8 | 7 |

The XRPD pattern of Pattern 1 of the co-crystal comprising psilocybin and benzylamine may be substantially as shown in FIG. 1.

The co-crystal comprising psilocybin and benzylamine may be in the form of the crystalline form designated as Pattern 2. Pattern 2 of the co-crystal comprising psilocybin and benzylamine typically has an x-ray powder diffraction (XRPD) pattern comprising peaks at 7.1°, 10.4° and 20.2°±0.2° 2θ.

The XRPD pattern of Pattern 2 of the co-crystal comprising psilocybin and benzylamine typically further comprises one or more peaks selected from 16.5°, 19.1°, and 19.9°±0.2° 2θ. The XRPD pattern of Pattern 2 of the co-crystal comprising psilocybin and benzylamine may further comprise peaks at 16.5°, 19.1°, and 19.9°±0.2° 2θ.

The XRPD pattern of Pattern 2 of the co-crystal comprising psilocybin and benzylamine may comprise five or more peaks selected from 7.1°, 10.4°, 11.1°, 13.8°, 16.5°, 18.2°, 19.1°, 19.9°, 20.2° and 22.8°±0.2° 2θ. The XRPD pattern may comprise seven or more of these peaks. The XRPD pattern may comprise all of these peaks. The XRPD pattern of Pattern 2 of the co-crystal comprising psilocybin and benzylamine may comprise the following peaks.

| Pattern 2 of the co-crystal of psilocybin and benzylamine | |
|---|---|
| Angle [°2θ] | Rel. Intensity [%] |
| 7.1 | 100 |
| 8.8 | 29 |
| 10.4 | 53 |
| 11.1 | 34 |
| 11.9 | 25 |
| 13.8 | 30 |
| 14.4 | 28 |
| 16.5 | 37 |
| 17.3 | 25 |
| 17.7 | 24 |
| 18.2 | 34 |
| 19.1 | 38 |
| 19.4 | 17 |
| 19.9 | 41 |
| 20.2 | 65 |
| 20.9 | 21 |
| 21.4 | 21 |
| 21.7 | 26 |
| 22.2 | 26 |
| 22.8 | 35 |
| 24.3 | 19 |
| 24.8 | 16 |
| 25.5 | 50 |
| 25.8 | 25 |
| 26.6 | 19 |
| 27.3 | 19 |

Figure 2:
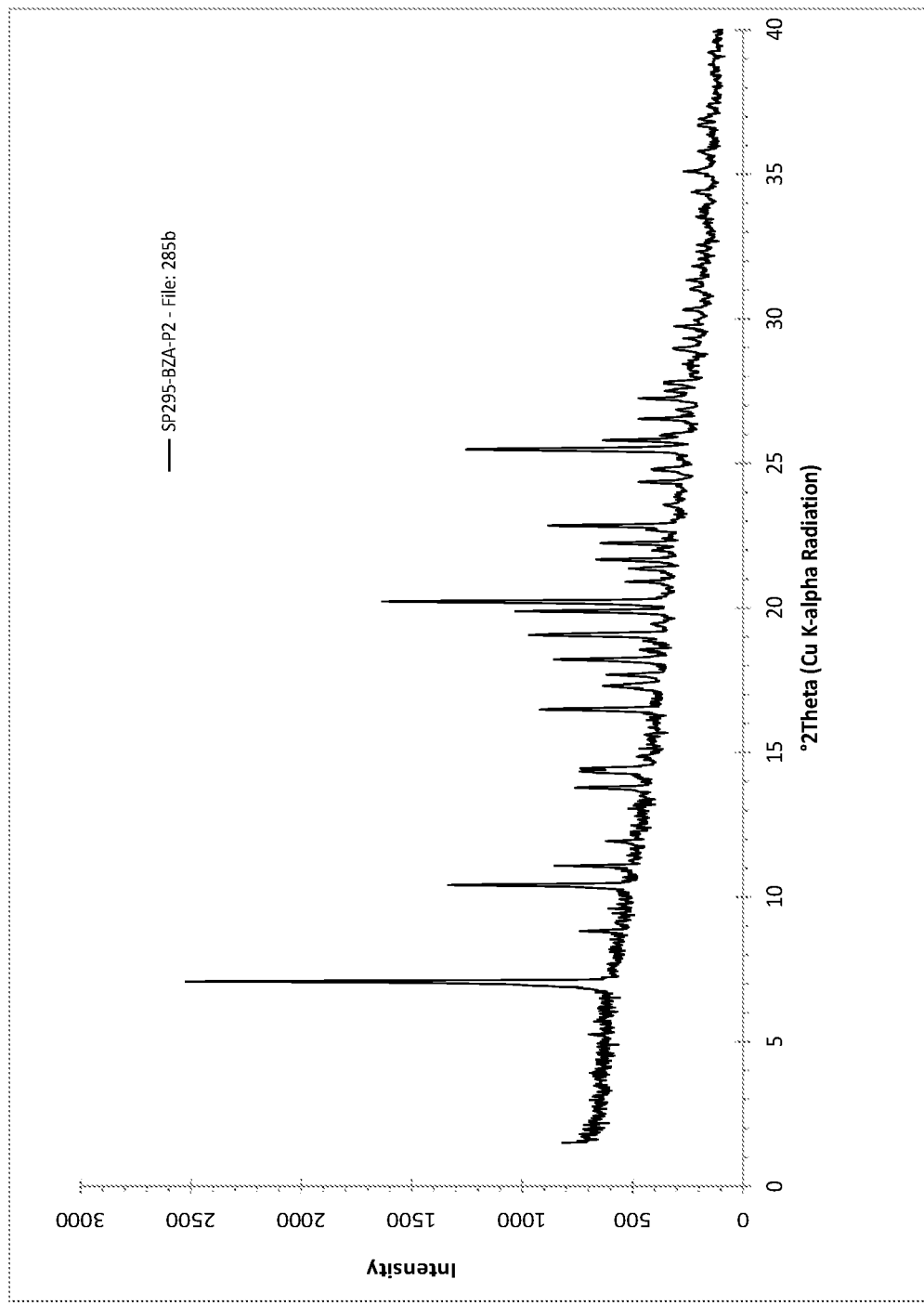
FIG. 2 shows the XRPD 2θ diffractogram of Pattern 2 of a co-crystal comprising psilocybin and benzylamine.

The XRPD pattern of Pattern 2 of the co-crystal comprising psilocybin and benzylamine may be substantially as shown in FIG. 2.

The co-crystal comprising psilocybin and diethylaminoethanol may be in the form of the crystalline form designated as Pattern 1. Pattern 1 of the co-crystal comprising psilocybin and diethylaminoethanol typically has an x-ray powder diffraction (XRPD) pattern comprising peaks at 5.6° and 14.5°±0.2° 2θ.

Figure 3:
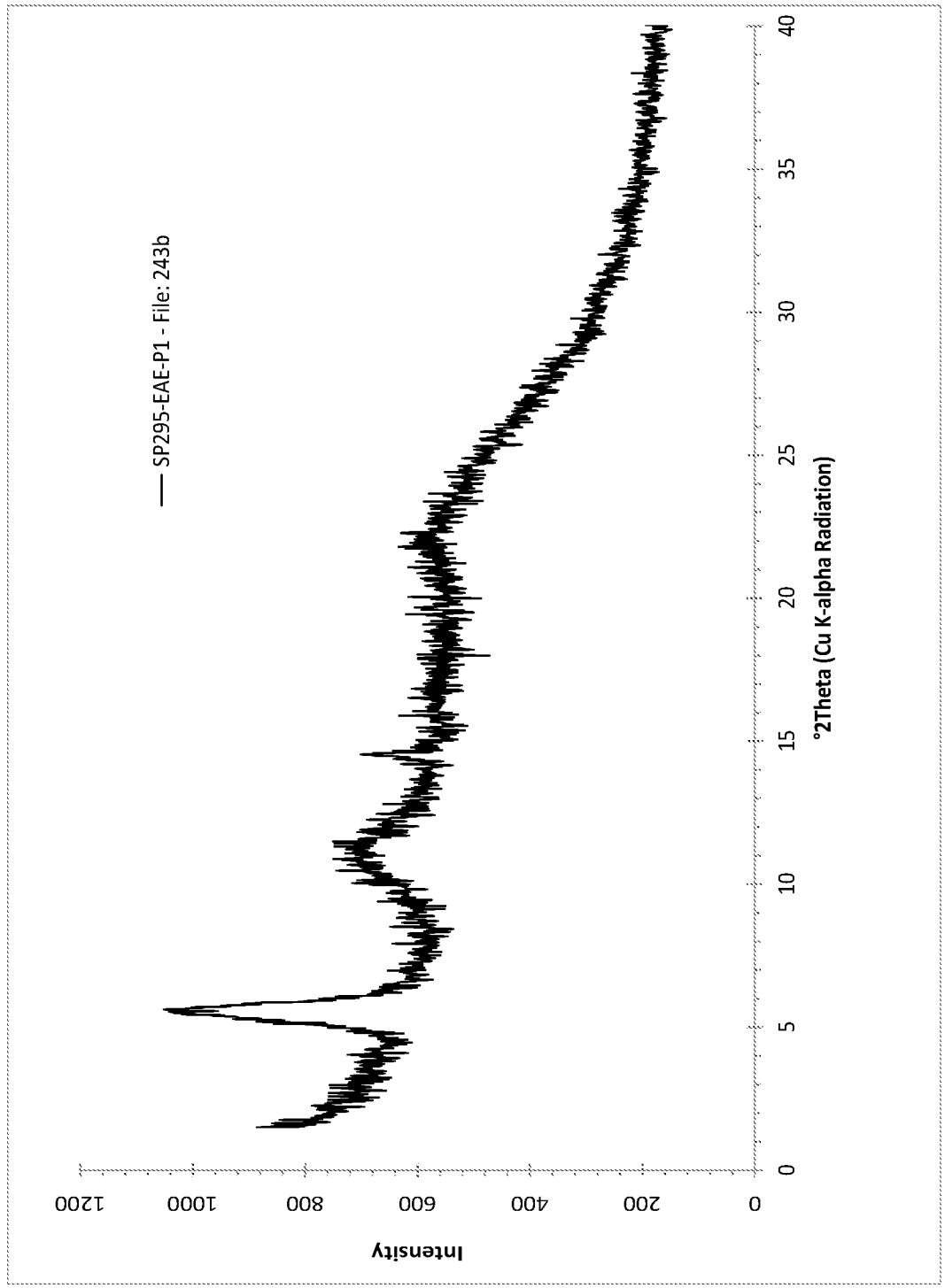
FIG. 3 shows the XRPD 2θ diffractogram of Pattern 1 of a co-crystal comprising psilocybin and diethylaminoethanol.

The XRPD pattern of Pattern 1 of the co-crystal comprising psilocybin and diethylaminoethanol may be substantially as shown in FIG. 3.

The co-crystal comprising psilocybin and 4-(2-hydroxyethyl) morpholine may be in the form of the crystalline form designated as Pattern 1. Pattern 1 of the co-crystal comprising psilocybin and 4-(2-hydroxyethyl) morpholine typically has an x-ray powder diffraction (XRPD) pattern comprising peaks at 12.3°, 22.3° and 23.7°±0.2° 2θ.

The XRPD pattern of Pattern 1 of the co-crystal comprising psilocybin and 4-(2-hydroxyethyl) morpholine typically further comprises one or more peaks selected from 5.8°, 11.8° and 24.4°±0.2° 2θ. The XRPD pattern of Pattern 1 of the co-crystal comprising psilocybin and 4-(2-hydroxyethyl) morpholine may further comprise peaks at 5.8°, 11.8° and 24.4°±0.2° 2θ.

The XRPD pattern of Pattern 1 of the co-crystal comprising psilocybin and 4-(2-hydroxyethyl) morpholine may comprise five or more peaks selected from 5.8°, 11.8°, 12.3°, 15.3°, 15.9°, 17.6°, 22.3°, 23.7°, 24.4° and 25.3°±0.2° 2θ. The XRPD pattern may comprise seven or more of these peaks. The XRPD pattern may comprise all of these peaks. The XRPD pattern of Pattern 1 of the co-crystal comprising psilocybin and 4-(2-hydroxyethyl) morpholine may comprise the following peaks.

| Pattern 1 of the co-crystal of psilocybin and 4-(2-hydroxyethyl) morpholine | |
|---|---|
| Angle [°2θ] | Rel. Intensity [%] |
| 5.8 | 50 |
| 11.8 | 45 |
| 12.3 | 90 |
| 14.00 | 24 |
| 14.8 | 25 |
| 15.3 | 33 |
| 15.9 | 31 |
| 17.6 | 33 |
| 17.9 | 25 |
| 19.2 | 19 |
| 19.7 | 16 |
| 20.3 | 23 |
| 20.5 | 25 |
| 21.0 | 25 |
| 21.7 | 29 |
| 22.3 | 56 |
| 22.6 | 22 |
| 23.7 | 100 |

| Pattern 1 of the co-crystal of psilocybin and 4-(2-hydroxyethyl) morpholine | |
|---|---|
| Angle [°2θ] | Rel. Intensity [%] |
| 24.4 | 42 |
| 24.6 | 19 |
| 24.9 | 16 |
| 25.3 | 37 |
| 25.8 | 21 |
| 27.4 | 19 |
| 30.7 | 19 |

Figure 4:
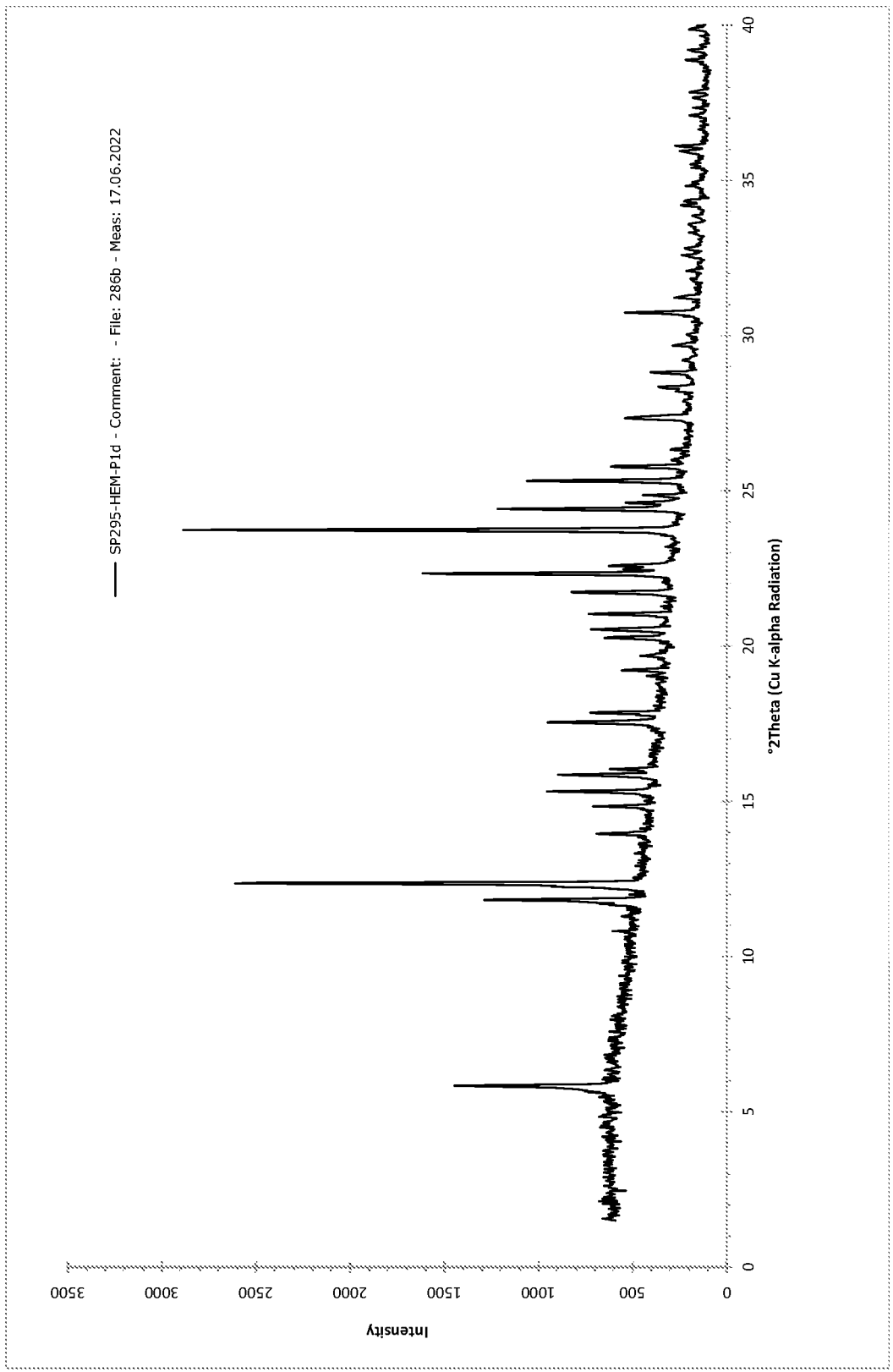
FIG. 4 shows the XRPD 2θ diffractogram of Pattern 1 of a co-crystal comprising psilocybin and 4-(2-hydroxyethyl)-morpholine.

The XRPD pattern of Pattern 1 of the co-crystal comprising psilocybin and 4-(2-hydroxyethyl) morpholine may be substantially as shown in FIG. 4.

The co-crystal comprising psilocybin and 1-(2-hydroxyethyl) pyrrolidine may be in the form of the crystalline form designated as Pattern 1. Pattern 1 of the co-crystal comprising psilocybin and 1-(2-hydroxyethyl) pyrrolidine typically has an x-ray powder diffraction (XRPD) pattern comprising peaks at 11.0°, 23.4° and 23.7°±0.2° 2θ.

The XRPD pattern of Pattern 1 of the co-crystal comprising psilocybin and 1-(2-hydroxyethyl) pyrrolidine typically further comprises one or more peaks selected from 12.1°, 18.7° and 20.1°±0.2° 2θ. The XRPD pattern of Pattern 1 of the co-crystal comprising psilocybin and 1-(2-hydroxyethyl) pyrrolidine may further comprise peaks at 12.1°, 18.7° and 20.1°±0.2° 2θ.

The XRPD pattern of Pattern 1 of the co-crystal comprising psilocybin and 1-(2-hydroxyethyl) pyrrolidine may comprise five or more peaks selected from 11.0°, 12.1°, 13.5°, 18.7°, 19.7°, 20.1°, 21.1°, 23.4°, 23.7° and 24.5°±0.2° 2θ. The XRPD pattern may comprise seven or more of these peaks. The XRPD pattern may comprise all of these peaks. The XRPD pattern of Pattern 1 of the co-crystal comprising psilocybin and 1-(2-hydroxyethyl) pyrrolidine may comprise the following peaks.

| Pattern 1 of the co-crystal of psilocybin and 1-(2-hydroxyethyl) pyrrolidine | |
|---|---|
| Angle [°2θ] | Rel. Intensity [%] |
| 3.2 | 24 |
| 5.6 | 20 |
| 6.5 | 24 |
| 11.0 | 100 |
| 11.6 | 26 |
| 12.1 | 39 |
| 13.1 | 22 |
| 13.5 | 32 |
| 15.0 | 23 |
| 15.8 | 21 |
| 18.2 | 20 |
| 18.7 | 39 |
| 19.0 | 24 |
| 19.7 | 29 |
| 20.1 | 38 |
| 21.1 | 29 |
| 21.9 | 54 |
| 22.7 | 26 |
| 23.4 | 59 |
| 23.7 | 70 |
| 24.5 | 32 |
| 25.3 | 17 |
| 25.7 | 20 |
| 30.6 | 16 |

Figure 5:
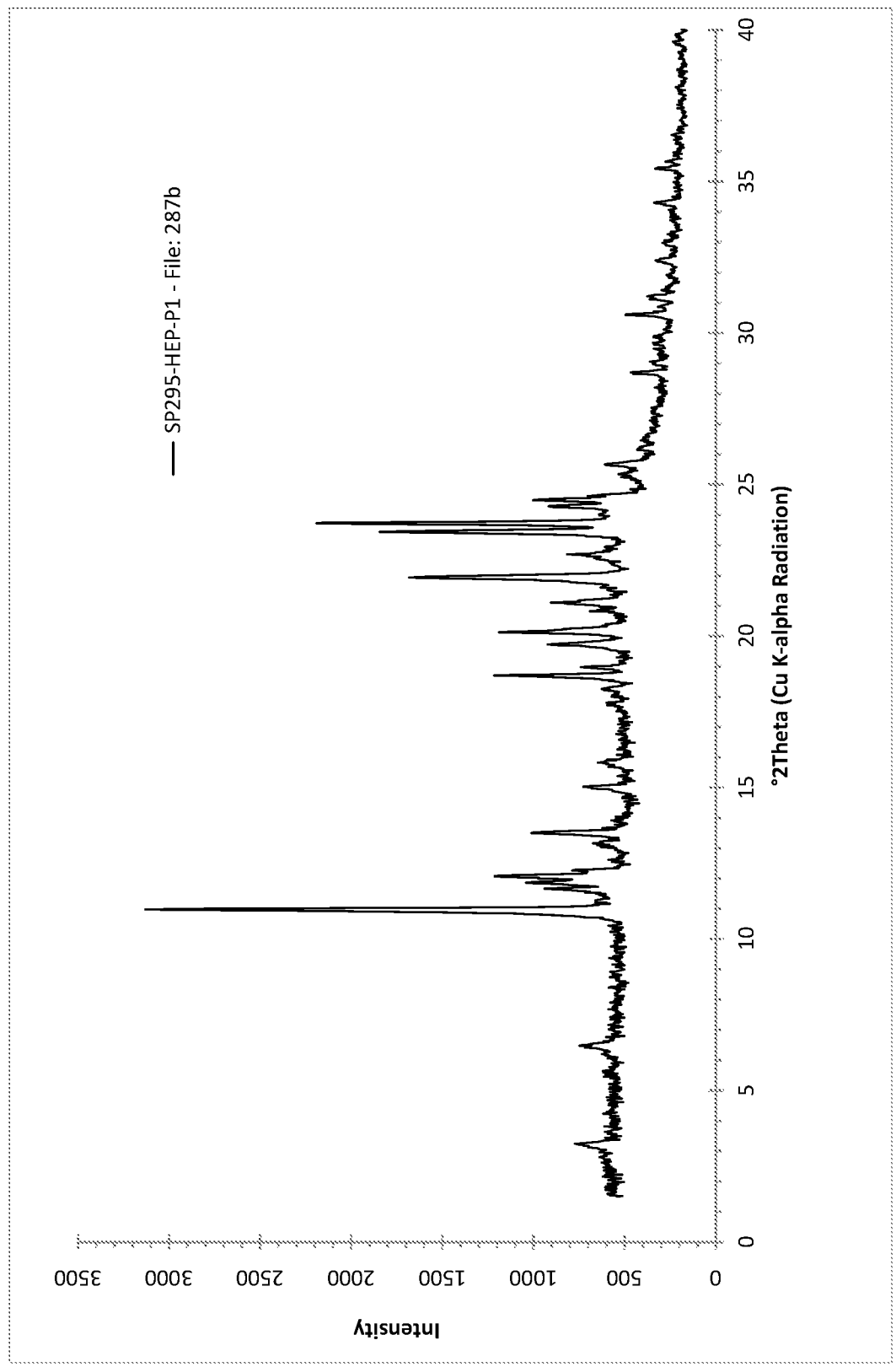
FIG. 5 shows the XRPD 2θ diffractogram of Pattern 1 of a co-crystal comprising psilocybin and 1-(2-hydroxyethyl) pyrrolidine.

The XRPD pattern of Pattern 1 of the co-crystal comprising psilocybin and 1-(2-hydroxyethyl) pyrrolidine may be substantially as shown in FIG. 5.

The co-crystal comprising psilocybin and deanol may be in the form of the crystalline form designated as Pattern 1. Pattern 1 of the co-crystal comprising psilocybin and deanol typically has an x-ray powder diffraction (XRPD) pattern comprising peaks at 21.4°, 23.3° and 24.3°±0.2° 2θ.

The XRPD pattern of Pattern 1 of the co-crystal comprising psilocybin and deanol typically further comprises one or more peaks selected from 10.8°, 11.6° and 20.9°±0.2° 2θ. The XRPD pattern of Pattern 1 of the co-crystal comprising psilocybin and deanol may further comprise peaks at 10.8°, 11.6° and 20.9°±0.2° 2θ.

The XRPD pattern of Pattern 1 of the co-crystal comprising psilocybin and deanol may comprise five or more peaks selected from 10.8°, 11.6°, 12.1°, 20.9°, 21.4°, 23.3°, 24.3°, 28.4° and 29.1°±0.2° 2θ. The XRPD pattern may comprise seven or more of these peaks. The XRPD pattern may comprise all of these peaks. The XRPD pattern of Pattern 1 of the co-crystal comprising psilocybin and deanol may comprise the following peaks.

| Pattern 1 of the co-crystal of psilocybin and deanol | |
|---|---|
| Angle [°2θ] | Rel. Intensity [%] |
| 5.2 | 12 |
| 5.6 | 13 |
| 10.8 | 40 |
| 11.3 | 18 |
| 11.6 | 51 |
| 12.1 | 22 |
| 13.3 | 16 |
| 17.5 | 12 |
| 19.3 | 18 |
| 19.9 | 12 |
| 20.9 | 54 |
| 21.4 | 100 |
| 22.5 | 20 |
| 22.9 | 14 |
| 23.3 | 85 |
| 24.3 | 98 |
| 24.7 | 12 |
| 28.4 | 37 |
| 29.1 | 27 |
| 30.1 | 17 |
| 32.8 | 11 |
| 34.6 | 18 |
| 35.1 | 20 |

Figure 6:
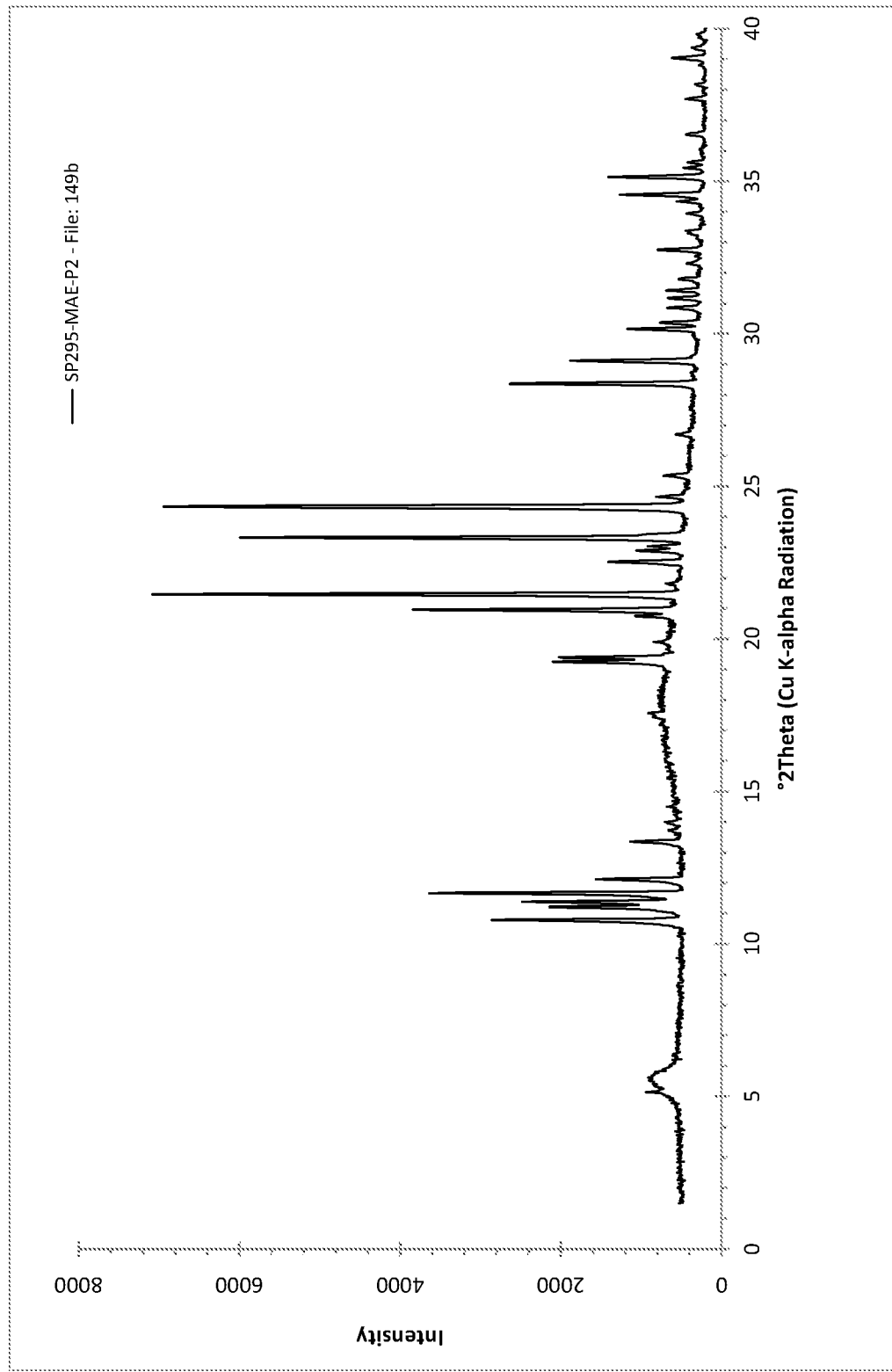
FIG. 6 shows the XRPD 2θ diffractogram of Pattern 1 of a co-crystal comprising psilocybin and deanol.

The XRPD pattern of Pattern 1 of the co-crystal comprising psilocybin and deanol may be substantially as shown in FIG. 6.

The co-crystal comprising psilocybin and deanol may be in the form of the crystalline form designated as Pattern 2. Pattern 2 of the co-crystal comprising psilocybin and deanol typically has an x-ray powder diffraction (XRPD) pattern comprising peaks at 12.4°, 19.9° and 20.6°±0.2° 2θ.

The XRPD pattern of Pattern 2 of the co-crystal comprising psilocybin and deanol typically further comprises one or more peaks selected from 14.0°, 17.5° and 23.2°±0.2° 2θ. The XRPD pattern of Pattern 2 of the co-crystal comprising psilocybin and deanol may further comprise peaks at 14.0°, 17.5° and 23.2°±0.2° 2θ.

The XRPD pattern of Pattern 2 of the co-crystal comprising psilocybin and deanol may comprise five or more peaks selected from 10.7°, 12.4°, 14.0°, 17.5°, 19.6°, 19.9°, 20.6°, 21.0° and 23.2°±0.2° 2θ. The XRPD pattern may comprise seven or more of these peaks. The XRPD pattern may comprise all of these peaks. The XRPD pattern of Pattern 2 of the co-crystal comprising psilocybin and deanol may comprise the following peaks.

| Pattern 2 of the co-crystal of psilocybin and deanol | |
|---|---|
| Angle [°2θ] | Rel. Intensity [%] |
| 7.0 | 18 |
| 10.7 | 31 |
| 11.3 | 22 |
| 12.4 | 100 |
| 14.0 | 38 |
| 15.0 | 23 |
| 17.5 | 35 |
| 18.1 | 18 |
| 18.6 | 18 |
| 19.0 | 19 |
| 19.6 | 33 |
| 19.9 | 57 |
| 20.4 | 18 |
| 20.6 | 54 |
| 21.0 | 30 |
| 21.3 | 20 |
| 21.8 | 27 |
| 22.7 | 17 |
| 23.2 | 47 |
| 23.5 | 24 |
| 24.1 | 22 |
| 25.0 | 27 |
| 25.8 | 12 |
| 27.2 | 23 |
| 28.4 | 29 |
| 29.6 | 17 |
| 32.6 | 17 |

Figure 7:
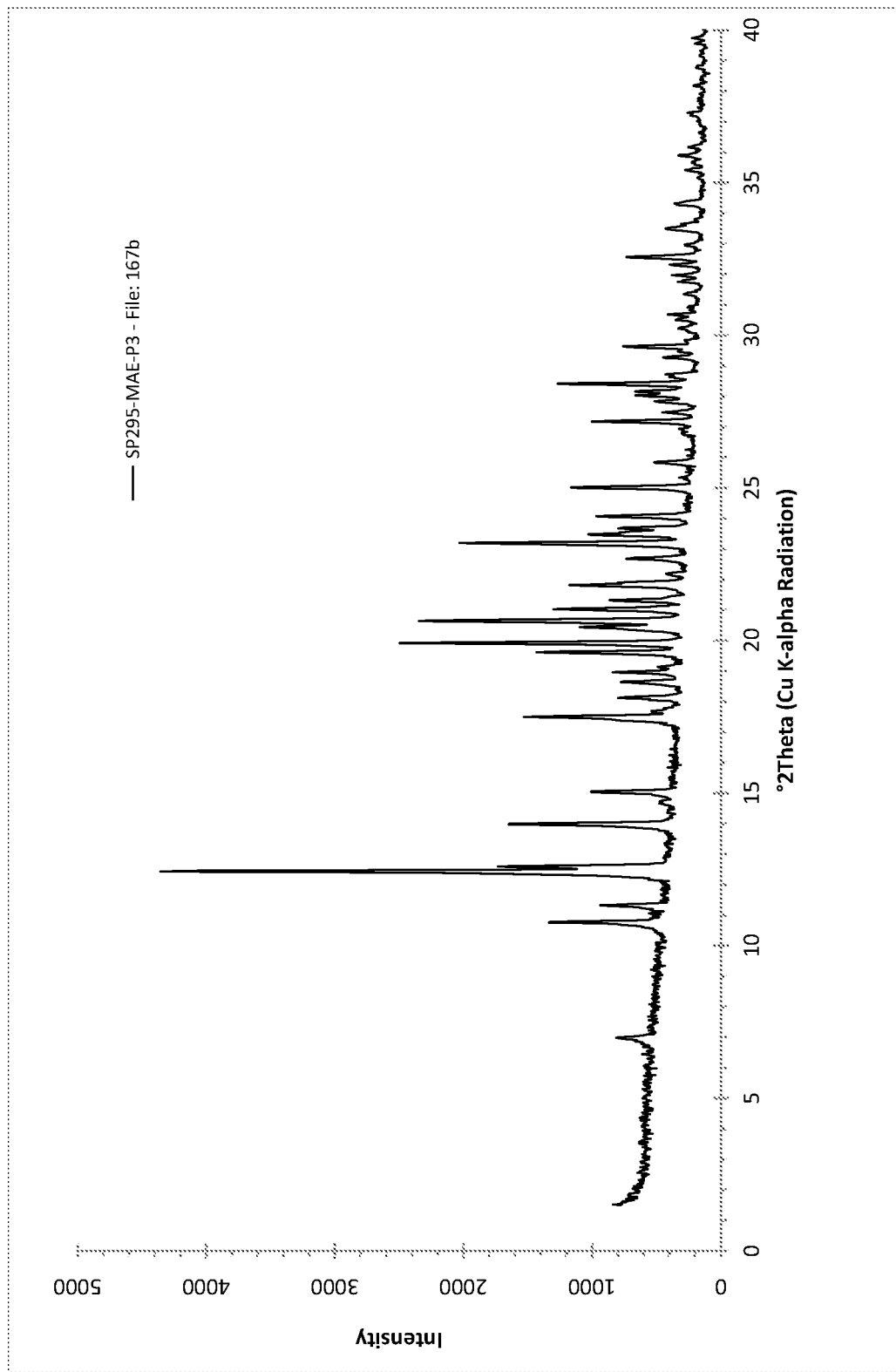
FIG. 7 shows the XRPD 2θ diffractogram of Pattern 2 of a co-crystal comprising psilocybin and deanol.

The XRPD pattern of Pattern 2 of the co-crystal comprising psilocybin and deanol may be substantially as shown in FIG. 7.

The co-crystal comprising psilocybin and deanol may be in the form of the crystalline form designated as Pattern 3. Pattern 3 of the co-crystal comprising psilocybin and deanol typically has an x-ray powder diffraction (XRPD) pattern comprising peaks at 10.30, 12.10 and 19.8°±0.2° 2θ.

The XRPD pattern of Pattern 3 of the co-crystal comprising psilocybin and deanol typically further comprises one or more peaks selected from 14.1°, 22.8° and 24.4°±0.2° 2θ. The XRPD pattern of Pattern 3 of the co-crystal comprising psilocybin and deanol may further comprise peaks at 14.1°, 22.8° and 24.4°±0.2° 2θ.

The XRPD pattern of Pattern 3 of the co-crystal comprising psilocybin and deanol may comprise five or more peaks selected from 10.3°, 12.1°, 14.1°, 14.6°, 17.6°, 19.8°, 21.9°, 22.8° and 24.4°±0.2° 2θ. The XRPD pattern may comprise seven or more of these peaks. The XRPD pattern may comprise all of these peaks. The XRPD pattern of Pattern 3 of the co-crystal comprising psilocybin and deanol may comprise the following peaks.

| Pattern 3 of the co-crystal of psilocybin and deanol | |
|---|---|
| Angle [°2θ] | Rel. Intensity [%] |
| 7.3 | 43 |
| 10.3 | 100 |
| 12.1 | 95 |
| 13.6 | 29 |
| 14.1 | 82 |
| 14.6 | 45 |
| 15.5 | 29 |
| 17.6 | 51 |
| 19.2 | 31 |
| 19.8 | 87 |
| 20.8 | 22 |
| 21.6 | 20 |
| 21.9 | 50 |
| 22.1 | 30 |
| 22.4 | 34 |
| 22.8 | 54 |
| 24.1 | 43 |
| 24.4 | 83 |
| 26.1 | 30 |
| 26.9 | 23 |
| 27.6 | 34 |
| 28.5 | 21 |
| 29.6 | 17 |
| 30.9 | 15 |
| 31.1 | 28 |
| 32.9 | 16 |
| 33.2 | 15 |
| 36.1 | 16 |
| 36.9 | 16 |

Figure 8:
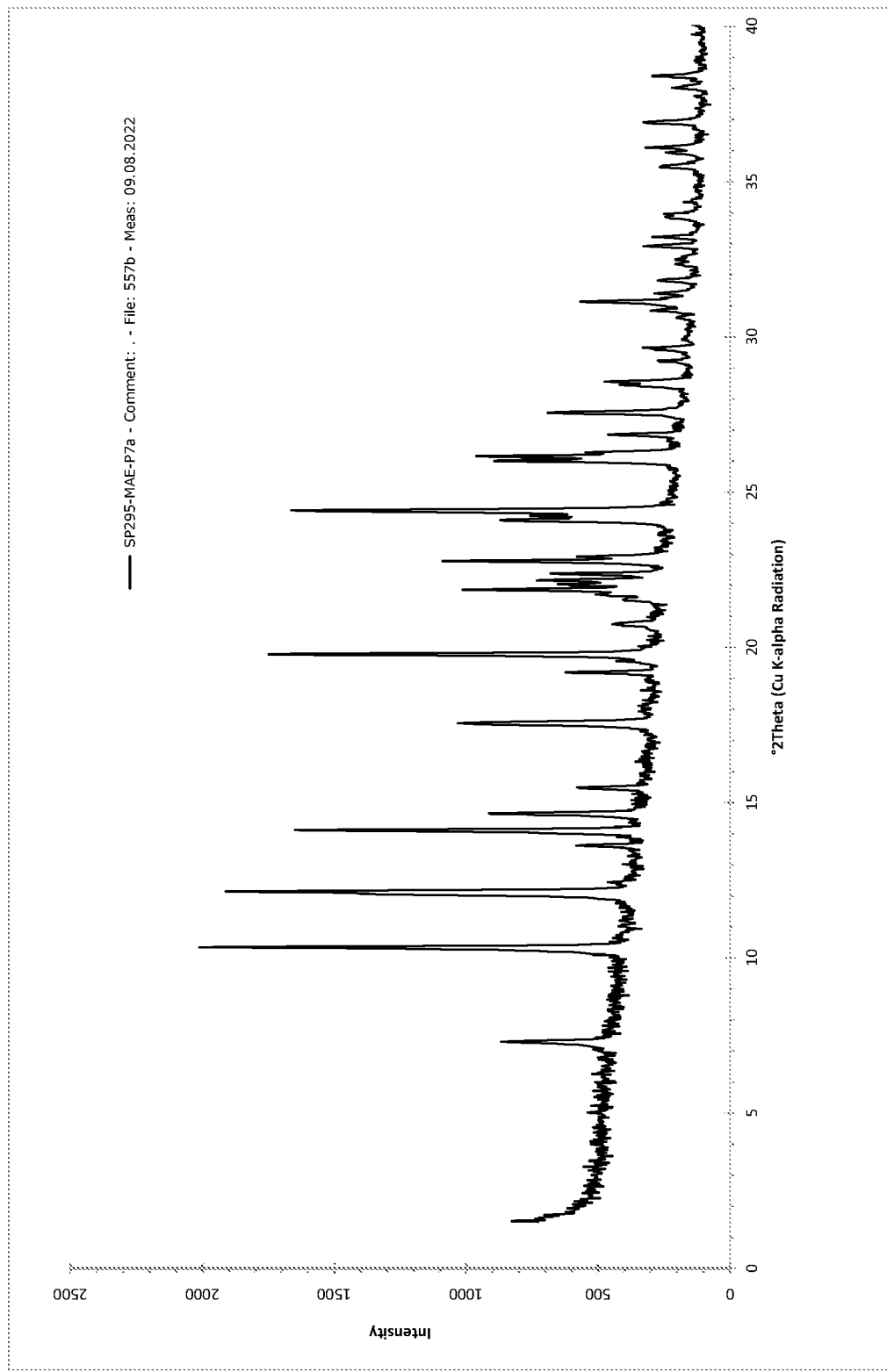
FIG. 8 shows the XRPD 2θ diffractogram of Pattern 3 of a co-crystal comprising psilocybin and deanol.

The XRPD pattern of Pattern 3 of the co-crystal comprising psilocybin and deanol may be substantially as shown in FIG. 8.

The co-crystal comprising psilocybin and piperazine may be in the form of the crystalline form designated as Pattern 1. Pattern 1 of the co-crystal comprising psilocybin and piperazine typically has an x-ray powder diffraction (XRPD) pattern comprising peaks at 13.1°, 15.4° and 24.4°±0.2° 2θ.

The XRPD pattern of Pattern 1 of the co-crystal comprising psilocybin and piperazine typically further comprises one or more peaks selected from 9.2°, 11.3° and 15.0°±0.2° 2θ. The XRPD pattern of Pattern 1 of the co-crystal comprising psilocybin and piperazine may further comprise peaks at 9.2°, 11.3° and 15.0°±0.2° 2θ.

The XRPD pattern of Pattern 1 of the co-crystal comprising psilocybin and piperazine may comprise five or more peaks selected from 9.2°, 11.3°, 13.1°, 15.0°, 15.4°, 19.3°, 22.7°, 23.8° and 24.4°±0.2° 2θ. The XRPD pattern may comprise seven or more of these peaks. The XRPD pattern may comprise all of these peaks. The XRPD pattern of Pattern 1 of the co-crystal comprising psilocybin and piperazine may comprise the following peaks.

| Pattern 1 of the co-crystal of psilocybin and piperazine | |
|---|---|
| Angle [°2θ] | Rel. Intensity [%] |
| 8.0 | 11 |
| 9.2 | 36 |
| 11.3 | 41 |
| 13.1 | 61 |
| 14.5 | 11 |
| 15.0 | 42 |
| 15.4 | 57 |
| 15.7 | 17 |
| 17.7 | 19 |
| 17.9 | 16 |
| 18.5 | 24 |
| 19.3 | 26 |
| 20.5 | 15 |
| 22.7 | 27 |
| 23.8 | 27 |
| 24.4 | 100 |
| 26.5 | 12 |
| 27.9 | 12 |
| 30.6 | 11 |

Figure 9:
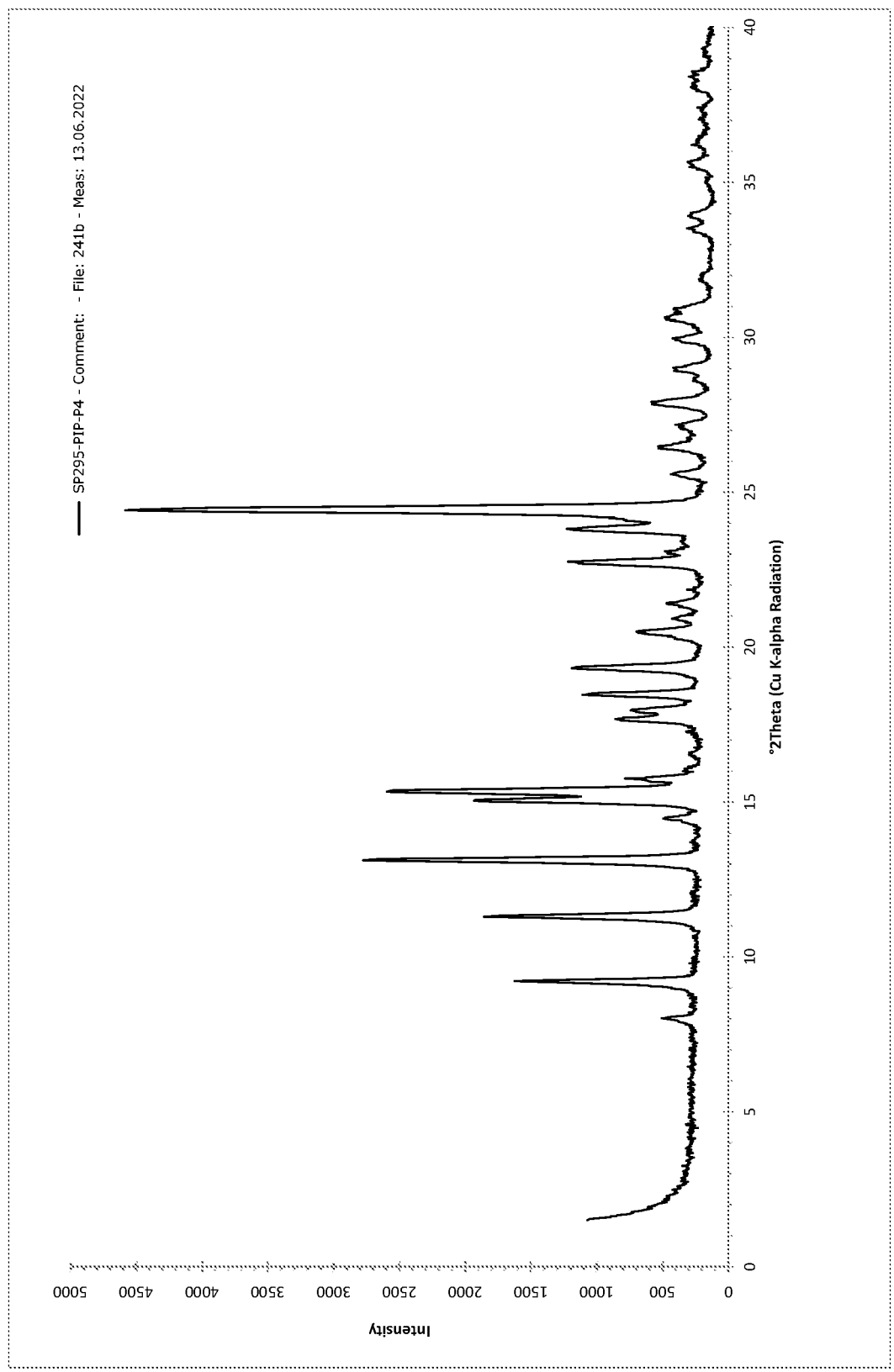
FIG. 9 shows the XRPD 2θ diffractogram of Pattern 1 of a co-crystal comprising psilocybin and piperazine.

The XRPD pattern of Pattern 1 of the co-crystal comprising psilocybin and piperazine may be substantially as shown in FIG. 9.

The co-crystal comprising psilocybin and piperazine may be in the form of the crystalline form designated as Pattern 2. Pattern 2 of the co-crystal comprising psilocybin and piperazine typically has an x-ray powder diffraction (XRPD) pattern comprising peaks at 13.1°, 17.3° and 24.6°±0.2° 2θ.

The XRPD pattern of Pattern 2 of the co-crystal comprising psilocybin and piperazine typically further comprises one or more peaks selected from 12.1°, 15.1° and 15.5°±0.2° 2θ. The XRPD pattern of Pattern 2 of the co-crystal comprising psilocybin and piperazine may further comprise peaks at 12.1°, 15.1° and 15.5°±0.2° 2θ.

The XRPD pattern of Pattern 2 of the co-crystal comprising psilocybin and piperazine may comprise five or more peaks selected from 9.3°, 12.1°, 13.1°, 15.1°, 15.5°, 17.3°, 18.7°, 21.4° and 24.6°±0.2° 2θ. The XRPD pattern may comprise seven or more of these peaks. The XRPD pattern may comprise all of these peaks. The XRPD pattern of Pattern 2 of the co-crystal comprising psilocybin and piperazine may comprise the following peaks.

Pattern 2 of the co-crystal of psilocybin and piperazine

| Angle [°2θ] | Rel. Intensity [%] |
|---|---|
| 6.5 | 11 |
| 9.3 | 30 |
| 12.1 | 39 |
| 13.1 | 48 |
| 13.8 | 17 |
| 15.1 | 47 |
| 15.5 | 33 |
| 17.3 | 61 |
| 17.6 | 13 |
| 18.7 | 31 |
| 19.4 | 13 |
| 20.7 | 23 |
| 21.4 | 31 |
| 21.7 | 26 |
| 24.6 | 100 |
| 25.1 | 18 |
| 25.4 | 12 |
| 25.8 | 16 |
| 29.5 | 11 |
| 30.4 | 15 |

Figure 10:
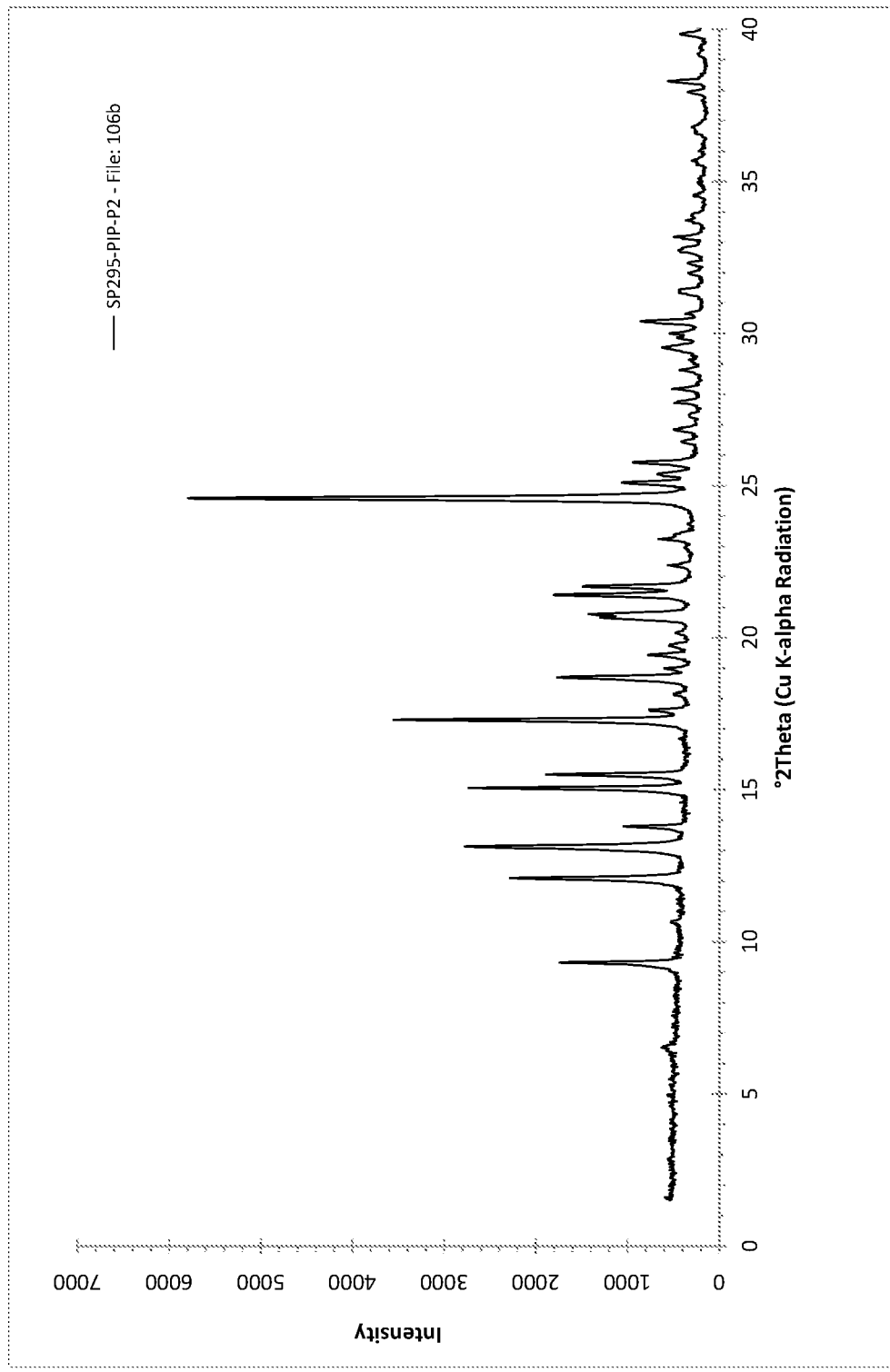
FIG. 10 shows the XRPD 2θ diffractogram of Pattern 2 of a co-crystal comprising psilocybin and piperazine.

The XRPD pattern of Pattern 2 of the co-crystal comprising psilocybin and piperazine may be substantially as shown in FIG. 10.

The co-crystal comprising psilocybin and pyridoxine may be in the form of the crystalline form designated as Pattern 1. Pattern 1 of the co-crystal comprising psilocybin and pyridoxine typically has an x-ray powder diffraction (XRPD) pattern comprising peaks at 8.8°, 13.2° and 20.9°±0.2° 2θ.

The XRPD pattern of Pattern 1 of the co-crystal comprising psilocybin and pyridoxine typically further comprises one or more peaks selected from 13.7°, 24.5° and 26.0°±0.2° 2θ. The XRPD pattern of Pattern 1 of the co-crystal comprising psilocybin and pyridoxine may further comprise peaks at 13.7°, 24.5° and 26.0°±0.2° 2θ.

The XRPD pattern of Pattern 1 of the co-crystal comprising psilocybin and pyridoxine may comprise five or more peaks selected from 8.8°, 13.2°, 13.7°, 15.9°, 20.9°, 22.2°, 24.5°, 25.8° and 26.0°±0.2° 2θ. The XRPD pattern may comprise seven or more of these peaks. The XRPD pattern may comprise all of these peaks. The XRPD pattern of Pattern 1 of the co-crystal comprising psilocybin and pyridoxine may comprise the following peaks.

Pattern 1 of the co-crystal of psilocybin and pyridoxine

| Angle [°2θ] | Rel. Intensity [%] |
|---|---|
| 5.8 | 25 |
| 8.8 | 78 |
| 11.9 | 24 |
| 13.2 | 73 |
| 13.7 | 60 |
| 14.5 | 22 |
| 14.8 | 23 |
| 15.7 | 24 |
| 15.9 | 48 |
| 17.0 | 22 |
| 18.3 | 27 |
| 18.5 | 34 |
| 19.4 | 34 |
| 19.8 | 23 |
| 20.9 | 100 |
| 22.2 | 48 |
| 23.8 | 22 |
| 24.5 | 58 |
| 24.8 | 22 |
| 25.8 | 35 |
| 26.0 | 54 |
| 26.6 | 27 |
| 26.9 | 23 |
| 27.5 | 30 |
| 29.4 | 21 |
| 30.2 | 23 |
| 31.1 | 25 |

Figure 11:
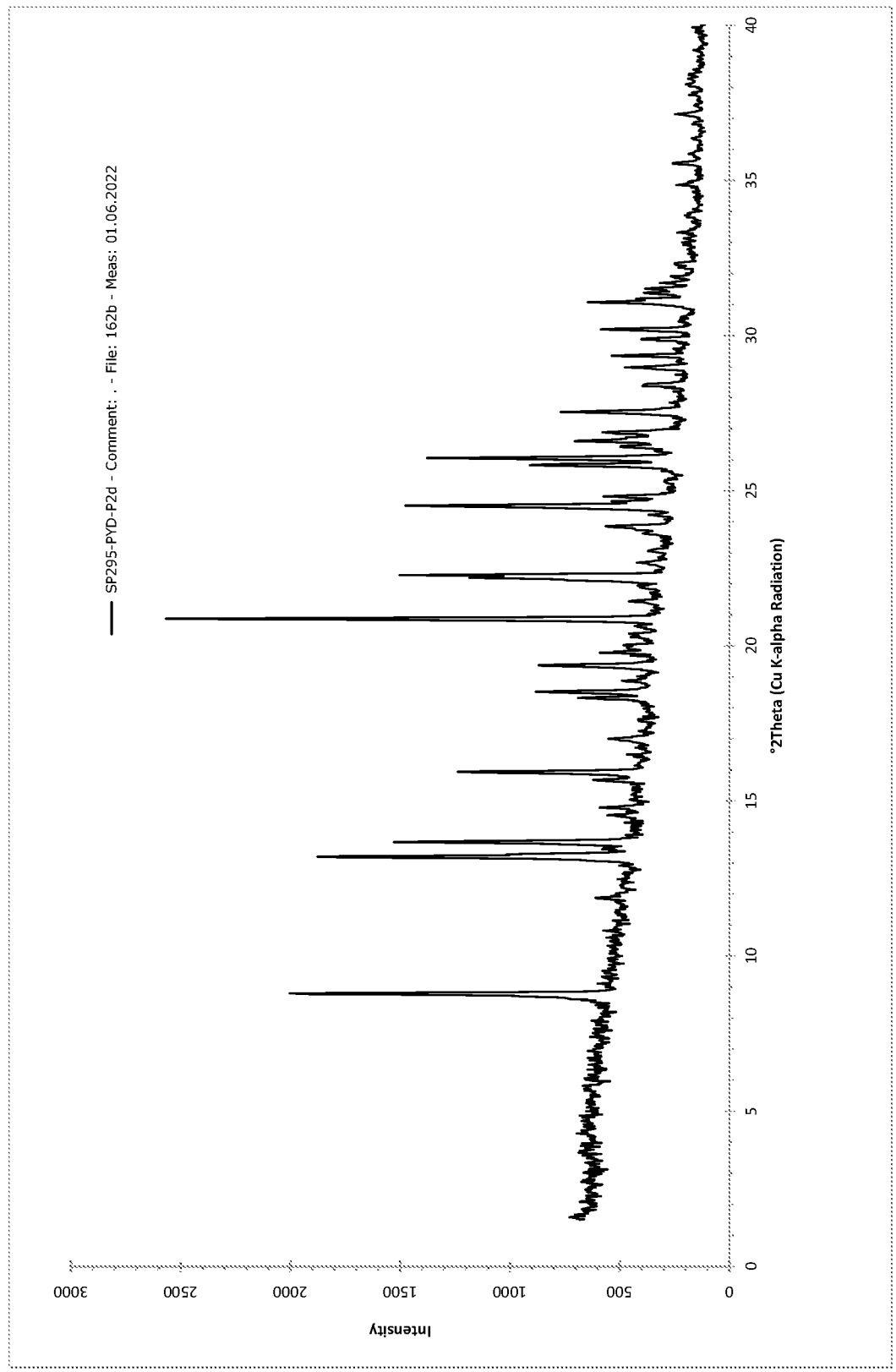
FIG. 11 shows the XRPD 2θ diffractogram of Pattern 1 of a co-crystal comprising psilocybin and pyridoxine.

The XRPD pattern of Pattern 1 of the co-crystal comprising psilocybin and pyridoxine may be substantially as shown in FIG. 11.

The co-crystal comprising psilocybin and tert-butylamine may be in the form of the crystalline form designated as Pattern 1. Pattern 1 of the co-crystal comprising psilocybin and tert-butylamine typically has an x-ray powder diffraction (XRPD) pattern comprising peaks at 7.6°, 10.0° and 21.5°±0.2° 2θ.

The XRPD pattern of Pattern 1 of the co-crystal comprising psilocybin and tert-butylamine typically further comprises one or more peaks selected from 9.1°, 18.4° and 18.9°±0.2° 2θ. The XRPD pattern of Pattern 1 of the co-crystal comprising psilocybin and tert-butylamine may further comprise peaks at 9.1°, 18.4° and 18.9°±0.2° 2θ.

The XRPD pattern of Pattern 1 of the co-crystal comprising psilocybin and tert-butylamine may comprise five or more peaks selected from 5.6°, 7.6°, 9.1°, 10.0°, 14.8°, 18.4°, 18.9°, 19.2°, 20.6° and 21.5°±0.2° 2θ. The XRPD pattern may comprise seven or more of these peaks. The XRPD pattern may comprise all of these peaks. The XRPD pattern of Pattern 1 of the co-crystal comprising psilocybin and tert-butylamine may comprise the following peaks.

Pattern 1 of the co-crystal of psilocybin and tert-butylamine

| Angle [°2θ] | Rel. Intensity [%] |
|---|---|
| 5.6 | 25 |
| 7.6 | 100 |
| 9.1 | 70 |
| 10.0 | 76 |
| 12.1 | 16 |
| 12.7 | 19 |
| 14.8 | 33 |
| 15.9 | 15 |
| 17.2 | 19 |
| 17.4 | 20 |
| 18.4 | 58 |
| 18.9 | 46 |
| 19.2 | 27 |

-continued

Pattern 1 of the co-crystal of psilocybin and tert-butylamine

| Angle [°2θ] | Rel. Intensity [%] |
|---|---|
| 20.6 | 25 |
| 21.5 | 74 |
| 22.3 | 16 |
| 23.4 | 21 |
| 24.4 | 19 |
| 26.3 | 17 |
| 30.2 | 20 |

Figure 12:
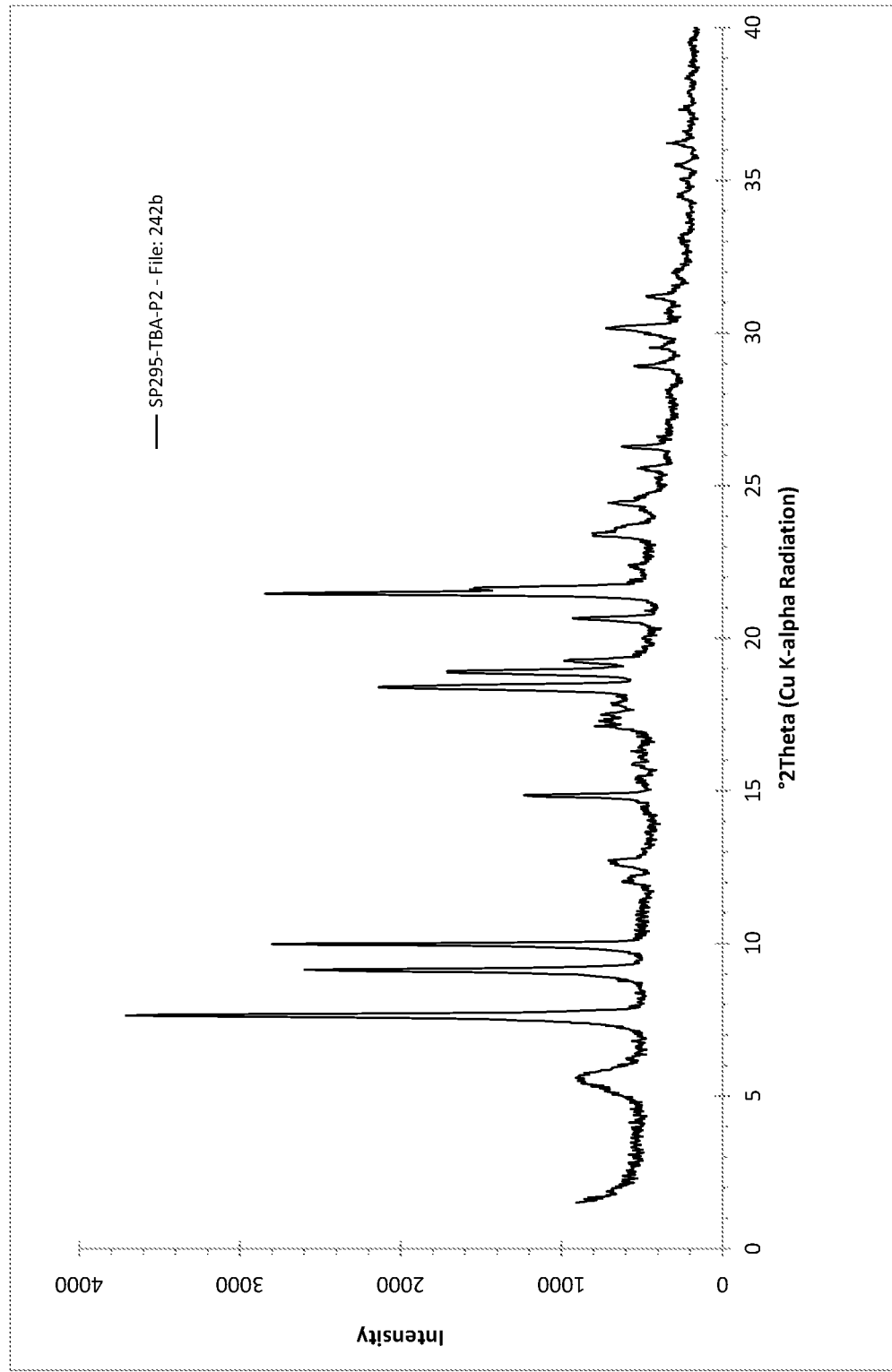
FIG. 12 shows the XRPD 2θ diffractogram of Pattern 1 of a co-crystal comprising psilocybin and tert-butylamine.

The XRPD pattern of Pattern 1 of the co-crystal comprising psilocybin and tert-butylamine may be substantially as shown in FIG. 12.

The co-crystal comprising psilocybin and tert-butylamine may be in the form of the crystalline form designated as Pattern 2. Pattern 2 of the co-crystal comprising psilocybin and tert-butylamine typically has an x-ray powder diffraction (XRPD) pattern comprising peaks at 7.7°, 9.2° and 10.0°±0.2° 2θ.

The XRPD pattern of Pattern 2 of the co-crystal comprising psilocybin and tert-butylamine typically further comprises one or more peaks selected from 18.4°, 18.9° and 21.5°±0.2° 2θ. The XRPD pattern of Pattern 2 of the co-crystal comprising psilocybin and tert-butylamine may further comprise peaks at 18.4°, 18.9° and 21.5°±0.2° 2θ.

The XRPD pattern of Pattern 2 of the co-crystal comprising psilocybin and tert-butylamine may comprise five or more peaks selected from 7.7°, 9.2°, 10.0°, 18.4°, 18.9°, 19.2°, 20.6°, 21.5°, 21.9°±0.2° 2θ. The XRPD pattern may comprise seven or more of these peaks. The XRPD pattern may comprise all of these peaks. The XRPD pattern of Pattern 2 of the co-crystal comprising psilocybin and tert-butylamine may comprise the following peaks.

Pattern 2 of the co-crystal of psilocybin and tert-butylamine

| Angle [°2θ] | Rel. Intensity [%] |
|---|---|
| 7.7 | 100 |
| 9.2 | 77 |
| 10.0 | 78 |
| 14.8 | 48 |
| 18.4 | 61 |
| 18.9 | 57 |
| 19.3 | 51 |
| 20.6 | 50 |
| 21.5 | 72 |
| 21.9 | 47 |
| 23.5 | 44 |
| 26.3 | 32 |
| 30.2 | 25 |
| 35.5 | 18 |
| 36.2 | 17 |

Figure 13:
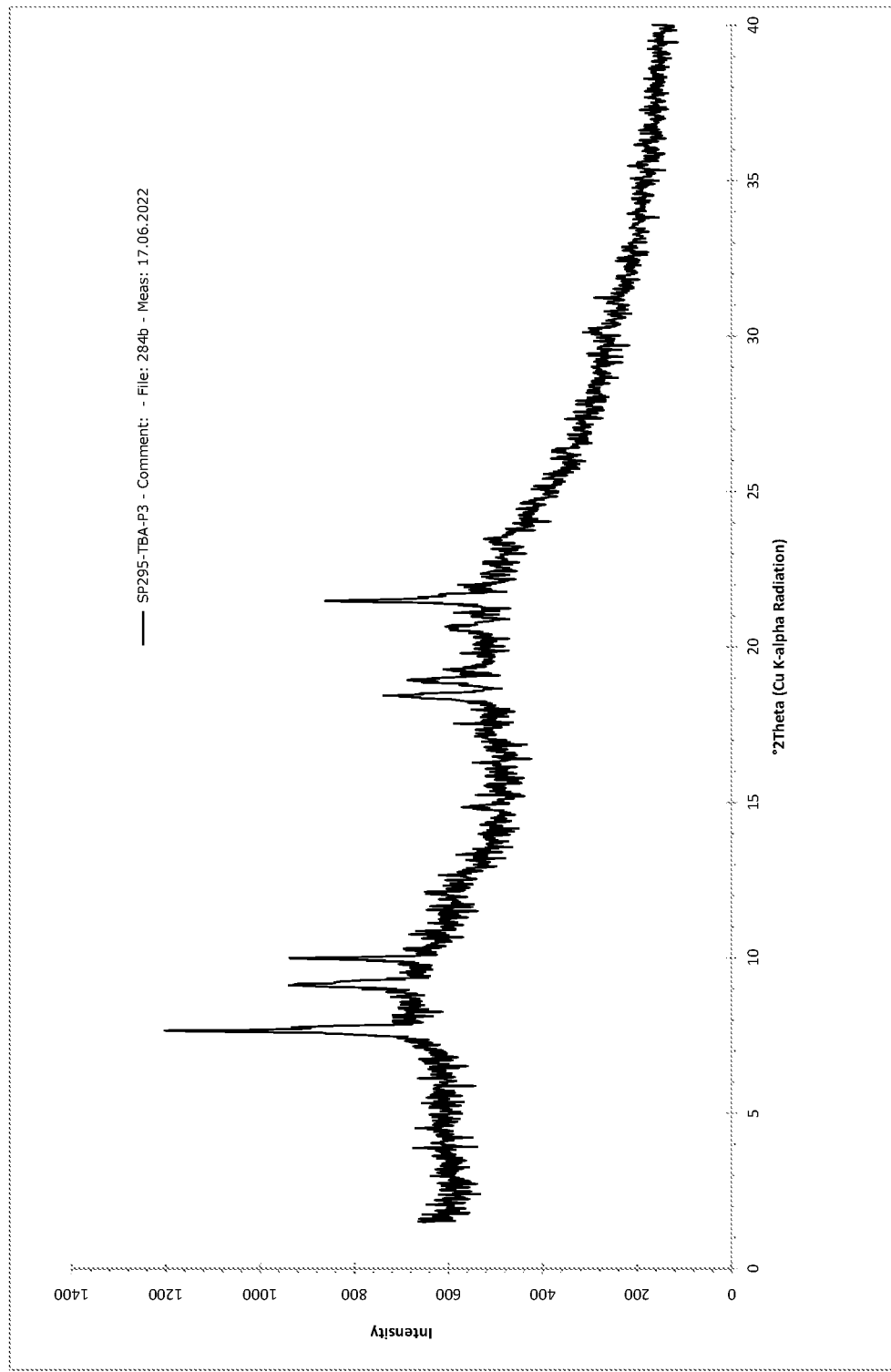
FIG. 13 shows the XRPD 2θ diffractogram of Pattern 2 of a co-crystal comprising psilocybin and tert-butylamine.

The XRPD pattern of Pattern 2 of the co-crystal comprising psilocybin and tert-butylamine may be substantially as shown in FIG. 13.

The co-crystal comprising psilocybin and urea may be in the form of the crystalline form designated as Pattern 1. Pattern 1 of the co-crystal comprising psilocybin and urea typically has an x-ray powder diffraction (XRPD) pattern comprising peaks at 14.4°, 21.1° and 25.0°±0.2° 2θ.

The XRPD pattern of Pattern 1 of the co-crystal comprising psilocybin and urea typically further comprises one or more peaks selected from 20.2°, 23.8° and 24.7°±0.2° 2θ. The XRPD pattern of Pattern 1 of the co-crystal comprising psilocybin and urea may further comprise peaks at 20.2°, 23.8° and 24.7°±0.2° 2θ.

The XRPD pattern of Pattern 1 of the co-crystal comprising psilocybin and urea may comprise five or more peaks selected from 11.2°, 14.4°, 20.2°, 20.6°, 21.1°, 22.2°, 23.8°, 24.7°, 25.0° and 27.7°±0.2° 2θ. The XRPD pattern may comprise seven or more of these peaks. The XRPD pattern may comprise all of these peaks. The XRPD pattern of Pattern 1 of the co-crystal comprising psilocybin and urea may comprise the following peaks.

Pattern 1 of the co-crystal of psilocybin and urea

| Angle [°2θ] | Rel. Intensity [%] |
|---|---|
| 11.2 | 20 |
| 14.4 | 100 |
| 15.1 | 16 |
| 16.5 | 12 |
| 17.2 | 16 |
| 18.4 | 10 |
| 20.2 | 37 |
| 20.6 | 19 |
| 21.1 | 42 |
| 22.2 | 18 |
| 23.8 | 24 |
| 24.2 | 13 |
| 24.7 | 21 |
| 25.0 | 43 |
| 25.6 | 16 |
| 27.7 | 18 |
| 29.1 | 16 |
| 31.9 | 12 |

Figure 14:
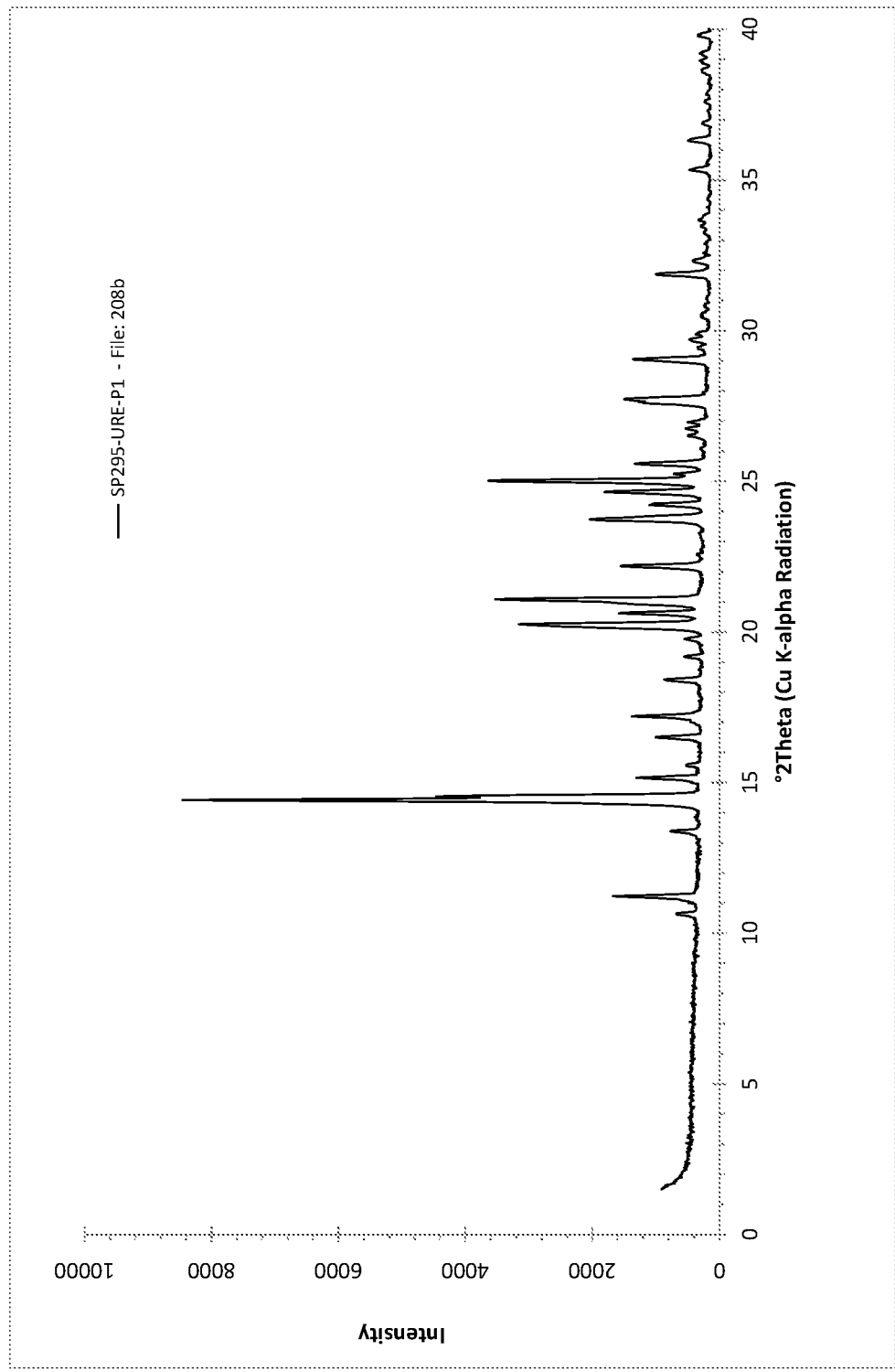
FIG. 14 shows the XRPD 2θ diffractogram of Pattern 1 of a co-crystal comprising psilocybin and urea.

The XRPD pattern of Pattern 1 of the co-crystal comprising psilocybin and urea may be substantially as shown in FIG. 14.

The co-crystal comprising psilocybin and propyl gallate may be in the form of the crystalline form designated as Pattern 1. Pattern 1 of the co-crystal comprising psilocybin and propyl gallate typically has an x-ray powder diffraction (XRPD) pattern comprising peaks at 9.3°, 19.3° and 21.3°±0.2° 2θ.

The XRPD pattern of Pattern 1 of the co-crystal comprising psilocybin and propyl gallate typically further comprises one or more peaks selected from 10.6°, 12.0° and 18.2°±0.2° 2θ. The XRPD pattern of Pattern 1 of the co-crystal comprising psilocybin and propyl gallate may further comprise peaks at 10.6°, 12.0° and 18.2°±0.2° 2θ.

The XRPD pattern of Pattern 1 of the co-crystal comprising psilocybin and propyl gallate may comprise five or more peaks selected from 9.3°, 10.6°, 12.0°, 12.8°, 15.0°, 18.2°, 19.3°, 21.3° and 24.4°±0.2° 2θ. The XRPD pattern may comprise seven or more of these peaks. The XRPD pattern may comprise all of these peaks. The XRPD pattern of Pattern 1 of the co-crystal comprising psilocybin and propyl gallate may comprise the following peaks.

Pattern 1 of the co-crystal of psilocybin and propyl gallate

| Angle [°2θ] | Rel. Intensity [%] |
|---|---|
| 9.3 | 64 |
| 10.6 | 54 |
| 12.0 | 50 |
| 12.8 | 41 |
| 15.0 | 43 |
| 17.0 | 27 |
| 18.2 | 61 |
| 19.3 | 83 |
| 21.3 | 100 |

-continued

Pattern 1 of the co-crystal of psilocybin and propyl gallate

| Angle [°2θ] | Rel. Intensity [%] |
|---|---|
| 22.1 | 40 |
| 24.4 | 46 |
| 28.5 | 26 |

Figure 15:
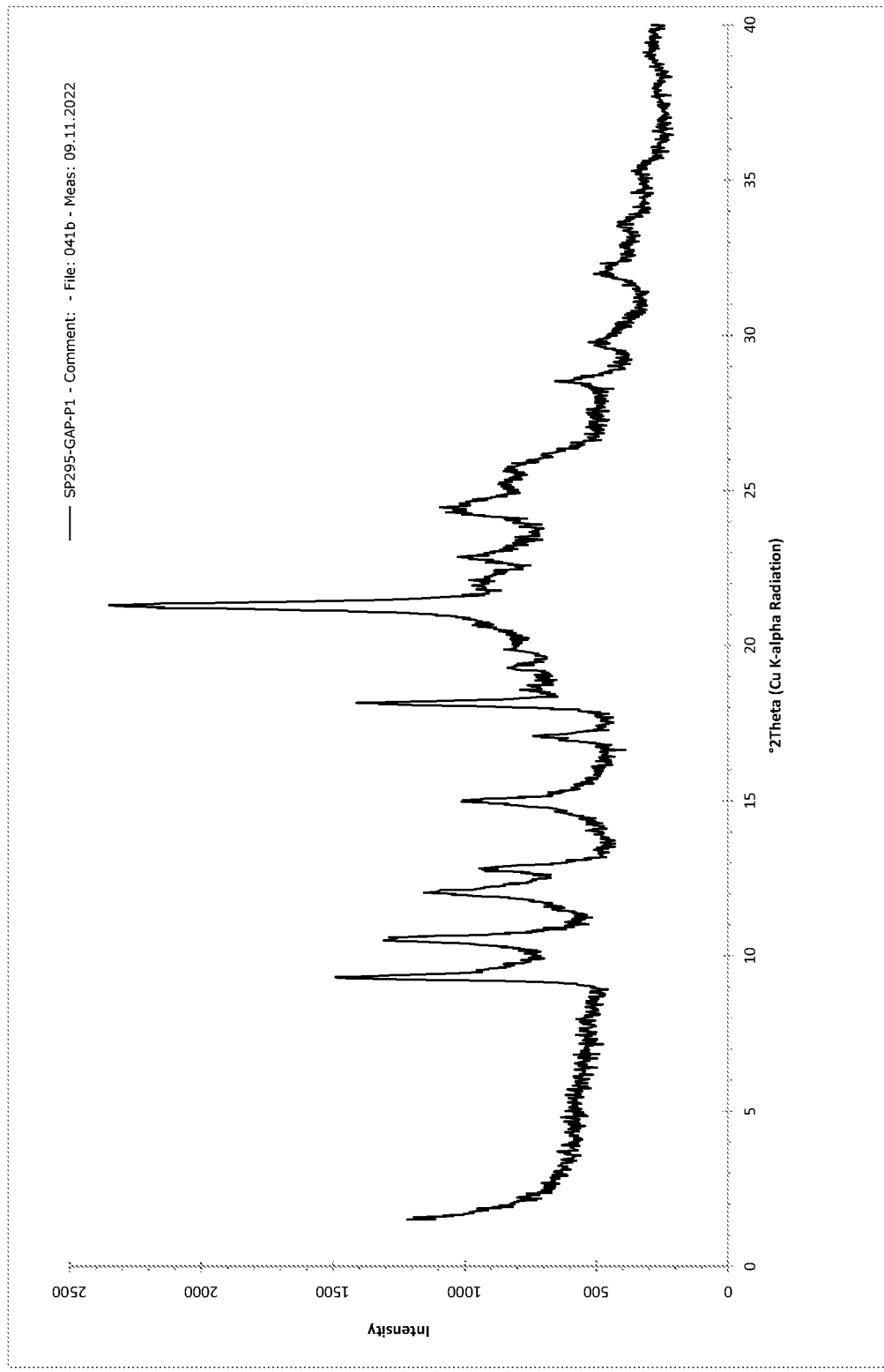
FIG. 15 shows the XRPD 2θ diffractogram of Pattern 1 of a co-crystal comprising psilocybin and propyl gallate.

The XRPD pattern of Pattern 1 of the co-crystal comprising psilocybin and propyl gallate may be substantially as shown in FIG. 15.

The invention also provides a composition comprising the co-crystal, where at least 50 wt %, at least 80 wt % or at least 90 wt % of the co-crystal is in the form of a crystalline form of that co-crystal defined herein.

Co-Crystals with Acid

Also disclosed herein is a co-crystal comprising psilocybin and a co-former, wherein the co-former is an acid. An acid may be any substance which can act as a proton donor. Alternatively, an acid may be any substance which can act as an electron pair acceptor. Alternatively, an acid may be any substance which increases the concentration of $H_3O^+$ ions in an aqueous solution.

The co-former may be an organic acid or an inorganic acid. Typically, the co-former is an organic acid.

Typically, the co-former is a compound which comprises one or more acidic functional groups. The acidic functional group may be selected from, for example, a carboxylic acid moiety, a sulfonic acid moiety, a squaric acid moiety, a sulphonamide moiety, a carboxylic sulfonimide moiety, and a sulfimide moiety. Thus, the co-former may be a compound which comprises one or more of a carboxylic acid moiety, a sulfonic acid moiety, a squaric acid moiety, a sulphonamide moiety, a carboxylic sulfonimide moiety, and a sulfimide moiety. Typically, the co-former is a compound which comprises a carboxylic acid moiety. The co-former may be a compound which comprises a sulfonic acid moiety. The co-former may be a compound which comprises a squaric acid moiety. The co-former may be a compound which comprises a sulphonamide moiety. The co-former may be a compound which comprises a carboxylic sulfonimide moiety. The co-former may be a compound which comprises a sulfimide moiety.

A co-former which has a $pK_a$ of less than 1.3 may protonate the phosphate residue in the zwitterionic psilocybin, and thus form a simple salt with psilocybin. Typically, a co-crystal will form where the $pK_a$ of the acid is not sufficiently low enough to facilitate complete transfer of a proton to the phosphoric acid residue in psilocybin. Therefore, the co-former typically has a $pK_a$ of greater than or equal to 1.3, for example greater than or equal to 1.5, 1.75, 2.0, 2.25, 2.5, 2.75, 3.0, 3.5, 4.0, or 4.5. Typically, the co-former typically has a $pK_a$ of greater than or equal to 1.5, 2.0, or 2.5. The co-former may have a $pK_a$ of greater than or equal to 1.5. The co-former may have a $pK_a$ of greater than or equal to 2.0. The co-former may have a $pK_a$ of greater than or equal to 2.5.

The co-former may have a $pK_a$ of less than or equal to 7.0, for example less than or equal to 6.5, 6.0, 5.5, or 5.0. Typically, the co-former has a $pK_a$ of less than or equal to 7.0, 6.0 or 5.0. The co-former may have a $pK_a$ of less than or equal to 7.0. The co-former may have a $pK_a$ of less than or equal to 6.0. The co-former may have a $pK_a$ of less than or equal to 5.0.

The co-former may have a $pK_a$ of from 1.5 to 7.0. For example, the co-former may have a $pK_a$ of from 1.5 to 6.0, or from 1.5 to 5.0, or from 1.5 to 4.5, or from 1.5 to 4.0. The co-former may have a $pK_a$ of from 2.0 to 6.0, or from 2.0 to 5.0, or from 2.0 to 4.5, or from 2.0 to 4.0. The co-former may have a $pK_a$ of from 2.5 to 6.0, or from 2.5 to 5.0, or from 2.5 to 4.5, or from 2.5 to 4.0. Typically, the co-former has a $pK_a$ of from 1.5 to 5.0.

The co-former may be selected from: sulfurous acid, sulfuric acid, sulfoxylic acid, persulfuric acid, disulfuric acid, disulfurous acid, dithionous acid, tetrathionic acid, hydrosulfuric acid, peroxydisulfuric acid, perchloric acid, hydrochloric acid, hypochlorous acid, chlorous acid, chloric acid, hyponitrous acid, nitrous acid, nitric acid, pernitric acid, formic acid, 2-hydroxyethanoic acid, oxoacetic acid, carbonic acid, oxalic acid, acetic acid, fluoroacetic acid, trifluoroacetic acid, chloroacetic acid, dichloroacetic acid, trichloroacetic acid, phosphoric acid, phosphinic acid, perphosphoric acid, hypophosphoric acid, diphosphoric acid, hydrobromic acid, bromous acid, bromic acid, hypobromous acid, perbromic acid, hypoiodous acid, iodous acid, iodic acid, periodic acid, hydroiodic acid, hypofluorous acid, hydrofluoric acid, methanesulfonic acid, ethanesulfonic acid, benzenesulfonic acid, squaric acid, chromic acid, selenic acid, selenous acid, boric acid, telluric acid, citric acid, pyrocitric acid, isocitric acid, sorbic acid, permanganic acid, silicic acid, dichromic acid, cyanic acid, malonic acid, tartronic acid, glycidic acid, tartaric acid (including L-tartaric acid, D-tartaric acid, or a mixture thereof), phthalic acid, barbituric acid, benzilic acid, cinnamic acid, fumaric acid, glutaric acid, gluconic acid, hexanoic acid, heptanoic acid, lactic acid (including L-lactic acid, D-lactic acid, or a mixture thereof), malic acid (including L-malic acid, D-malic acid, or a mixture thereof), oleic acid, linoleic acid, folic acid, propiolic acid, propanoic acid, 2-hydroxypropanoic acid, 3-hydroxypropanoic acid, 2,3-dihydroxypropanoic acid, propenoic acid, pyruvic acid, butyric acid, isobutyric acid, tetrolic acid, valeric acid, pivalic acid, caproic acid, capric acid, fulvic acid, mellitic acid, palmitic acid, adipic acid, phthalic acid, stearic acid, ascorbic acid (including L-ascorbic acid, D-ascorbic acid, or a mixture thereof), gallic acid, N-acetyl glycine, alginic acid, tannic acid, benzoic acid, salicylic acid, 2-(4-hydroxybenzoyl)benzoic acid, 2-(3-hydroxybenzoyl)benzoic acid, 2-(2-hydroxybenzoyl)benzoic acid, 3-(2-hydroxybenzoyl)benzoic acid, 3-(3-hydroxybenzoyl)benzoic acid, 3-(4-hydroxybenzoyl)benzoic acid 4-(2-hydroxybenzoyl)benzoic acid, 4-(3-hydroxybenzoyl)benzoic acid, 4-(4-hydroxybenzoyl)benzoic acid, glucoheptonic acid, 1-naphthoic acid, 2-naphthoic acid, 1-hydroxy-2-naphthoic acid, 3-hydroxy-2-naphthoic acid, 2-hydroxy-1-naphthoic acid, 3-hydroxy-1-naphthoic acid, orotic acid, acetoacetic acid, succinic acid, ketosuccinic acid, methylmalonic acid, ferulic acid, fumaric acid, gentisic acid, p-coumaric acid, m-coumaric acid, o-coumaric acid, disodium EDTA, EDTA, nicotinic acid, glutaric acid, 2-ketoglutaric acid, 3-ketoglutaric acid, 2-furoic acid, tetrahydrofuroic acid, 4-hydroxyphenyl acetic acid, 3-hydroxyphenyl acetic acid, 2-hydroxyphenyl acetic acid, maleic acid, oxalic acid, saccharin, phosphonic acid, ethyl phosphonic acid, propyl phosphonic acid, hippuric acid, sebacic acid, camphoric acid, aconitic acid, and thiodipropionic acid.

The co-former may be selected from: N-acetyl glycine, alginic acid, 2-(4-hydroxybenzoyl)benzoic acid, gluconic acid, glucoheptonic acid, 2-naphthoic acid, orotic acid, succinic acid, L-ascorbic acid, L-tartaric acid, cinnamic acid, ferulic acid, fumaric acid, gentisic acid, gallic acid, citric acid, p-coumaric acid, L-lactic acid, disodium EDTA, nicotinic acid, 1-hydroxy-2-naphthoic acid, 2-ketoglutaric acid, 4-hydroxyphenyl acetic acid, L-malic acid, maleic acid, oxalic acid and saccharin.

Typically, the co-former is selected from citric acid, succinic acid, fumaric acid, gluconic acid, L-tartaric acid, L-ascorbic acid, L-lactic acid, saccharin, disodium EDTA and nicotinic acid.

The co-crystal may comprise psilocybin and a co-former which is N-acetyl glycine. The co-crystal may comprise psilocybin and a co-former which is alginic acid. The co-crystal may comprise psilocybin and a co-former which is 2-(4-hydroxybenzoyl)benzoic acid. The co-crystal may comprise psilocybin and a co-former which is gluconic acid. The co-crystal may comprise psilocybin and a co-former which is glucoheptonic acid. The co-crystal may comprise psilocybin and a co-former which is 2-naphthoic acid. The co-crystal may comprise psilocybin and a co-former which is orotic acid. The co-crystal may comprise psilocybin and a co-former which is succinic acid. The co-crystal may comprise psilocybin and a co-former which is L-ascorbic acid. The co-crystal may comprise psilocybin and a co-former which is L-tartaric acid. The co-crystal may comprise psilocybin and a co-former which is cinnamic acid. The co-crystal may comprise psilocybin and a co-former which is ferulic acid. The co-crystal may comprise psilocybin and a co-former which is fumaric acid. The co-crystal may comprise psilocybin and a co-former which is gentisic acid. The co-crystal may comprise psilocybin and a co-former which is gallic acid. The co-crystal may comprise psilocybin and a co-former which is citric acid. The co-crystal may comprise psilocybin and a co-former which is p-coumaric acid. The co-crystal may comprise psilocybin and a co-former which is L-lactic acid. The co-crystal may comprise psilocybin and a co-former which is disodium EDTA. The co-crystal may comprise psilocybin and a co-former which is nicotinic acid. The co-crystal may comprise psilocybin and a co-former which is 1-hydroxy-2-naphthoic acid. The co-crystal may comprise psilocybin and a co-former which is 2-ketoglutaric acid. The co-crystal may comprise psilocybin and a co-former which is 4-hydroxyphenyl acetic acid. The co-crystal may comprise psilocybin and a co-former which is L-malic acid. The co-crystal may comprise psilocybin and a co-former which is maleic acid. The co-crystal may comprise psilocybin and a co-former which is oxalic acid. The co-crystal may comprise psilocybin and a co-former which is saccharin.

Co-Crystals with a Base

Also disclosed herein is a co-crystal comprising psilocybin and a co-former, wherein the co-former is a base. A base may be any substance which can act as a proton acceptor. Alternatively, a base may be any substance which can act as an electron pair donor. Alternatively, a base may be any substance which increases the concentration of $OH^-$ ions in an aqueous solution.

The co-former may be an organic base or an inorganic base. Typically, the co-former is an organic base.

Typically, the co-former is a compound which comprises one or more basic functional groups. The basic functional group may be selected from, for example, an amine moiety, a pyridine moiety, a piperazine moiety, an amide moiety, a xanthine moiety and a morpholine moiety. Thus, the co-former may be a compound which comprises one or more of an amine moiety, a pyridine moiety, a piperazine moiety, an amide moiety, a xanthine moiety and a morpholine moiety. Typically, the co-former is a compound which comprises an amine moiety. The co-former may be a compound which comprises a pyridine moiety. The co-former may be a compound which comprises a piperazine moiety. The co-former may be a compound which comprises an amide moiety. The co-former may be a compound which comprises a xanthine moiety. The co-former may be a compound which comprises a morpholine moiety.

A co-former which is a strong base may deprotonate the tertiary amine residue in the zwitterionic psilocybin, and thus form a simple salt with psilocybin. Typically, a co-crystal will form where the $pK_b$ of the base is not sufficiently low enough to facilitate complete transfer of a proton from the amine residue in psilocybin.

Therefore, the co-former typically has a $pK_b$ of greater than or equal to 3.5, for example greater than or equal to 4.0, 4.5, 5.0, 5.5, 6.0, 6.5, 7.0 or 7.5. Typically, the co-former typically has a $pK_b$ of greater than or equal to 3.5, 4.5, or 5.5. The co-former may have a $pK_b$ of greater than or equal to 3.5. The co-former may have a $pK_b$ of greater than or equal to 4.5. The co-former may have a $pK_b$ of greater than or equal to 5.5.

The co-former may have a $pK_b$ of less than or equal to 11.0, for example less than or equal to 10.5, 10.0, 9.5, 9.0, 8.5, or 8.0. Typically, the co-former has a $pK_b$ of less than or equal to 11.0, 10.0 or 9.0. The co-former may have a $pK_b$ of less than or equal to 11.0. The co-former may have a $pK_b$ of less than or equal to 10.0. The co-former may have a $pK_b$ of less than or equal to 9.0.

The co-former may have a $pK_b$ of from 3.5 to 11.0. For example, the co-former may have a $pK_b$ of from 3.5 to 10.5, or from 3.5 to 10.0, or from 3.5 to 9.5, or from 3.5 to 9.0. The co-former may have a $pK_b$ of from 4.5 to 11.0, or from 4.5 to 10.5, or from 4.5 to 10.0, or from 4.5 to 9.5, or from 4.5 to 9.0. The co-former may have a $pK_b$ of from 5.5 to 11.0, or from 5.5 to 10.5, or from 5.5 to 10.0, or from 5.5 to 9.5, or from 5.5 to 9.0. Typically, the co-former has a $pK_b$ of from 5.5 to 11.0.

The co-former may be selected from: 1-aminopentane, 3-aminopentane, N-butylamine, sec-butylamine, tert-butylamine, propylhexedrine, cyclopentamine, cypenamine, cyclopentamine, dibutylamine, diethylamine, diisopropylamine, N,N-diisopropylethylamine, dimethylamine, 1,3-dimethylbutylamine, N,N-dimethylethylamine, dipropylamine, ethylamine, ethylmethylamine, hexylamine, isobutylamine, isopropylamine, methylamine, methylhexanamine, N,N-diethylmethylamine, octodrine, tert-octylamine, propylamine, tributylamine, triethylamine, triisopropylamine, trimethylamine, trioctylamine, 2-aminoheptane, tromethamine, 1,2-diaminocyclohexane, trans-1,2-diaminocyclohexane, 4,4-diaminodicyclohexylmethane, diaminomaleonitrile, 1,8-diaminonaphthalene, 1,5-diaminonaphthalene, diaminopropane, 1,2-diaminopropane, 1,3-diaminopropane, 2,4-diaminotoluene, 2,5-diaminotoluene, 1,4-diazacycloheptane, 1,5-diazacyclooctane, diazinane, N,N'-dimethyl-1,3-propanediamine, dimethyl-4-phenylenediamine, dimethylaminopropylamine, dimethylethylenediamine, 1,1-dimethylethylenediamine, 1,2-dimethylethylenediamine, diphenylethylenediamine, ethylenediamine, diethanolamine, N,N-diethylethanolamine, N,N-dimethylethanolamine (deanol), N,N-diisopropylaminoethanol, ethanolamine, methanolamine, pyridine, 1-methylpyridine, 2-methylpyridine, 3-methylpyridine, 4-methylpyridine, 2,4-dimethylpyridine, 2,6-dimethylpyridine, 1-ethylpyridine, 2-ethylpyridine, 3-ethylpyridine, 4-ethylpyridine, 2,4-diethylpyridine, 2,6-diethylpyridine, 2,2-bipyridine, 2,3-bipyridine, 2,4-bipyridine, 3,3-bipyridine, 3,4-bipyridine, 4,4-bipyridine, pyridoxine, pyridoxal, pyridoxamine, piperazine, 1-benzylpiperazine, 1-methyl-4-benzylpiperazine, 1,4-dibenzylpiperazine, 3,4-methylenedioxy-1-benzylpiperazine, methoxypiperamide, 1-phenylpiperazine, 2-methylphenylpiperazine, 2-methoxyphenylpiperazine, 3-methylphenylpiperazine, 3-methoxyphenylpiperazine, 4-methylphenylpiperazine, 4-methoxyphenylpiperazine, 2,3-methylphenylpiperazine, acetamide, benzamide, N-methylbenzamide, 4-methylbenzamide, 3-methylbenzamide, dimethylformamide, dimethylacetamide, diethylacetamide, butanamide, N-methylbutanamide, formamide, N-methylformamide, propanamide, 2-methylpropanamide, N-methylpropanamide, nicotinamide, isonicotinamide, morpholine, N-methylmorpholine, 2-methylmorpholine, 3-methylmorpholine, N-ethylmorpholine, 2-ethylmorpholine, 3-ethylmorpholine, N-propylmorpholine, 2-propylmorpholine, 3-propylmorpholine, N-methylmorpholine N-oxide, 4-(2-hydroxyethyl)-morpholine, 4-(1-hydroxyethyl)-morpholine, 4-(3-hydroxypropyl)-morpholine, 4-(2-hydroxypropyl)-morpholine, 1,3-dimethylxanthine (theophylline), 1-methylxanthine, 3-methylxanthine, 1,3-diethylxanthine, 1-ethylxanthine, 2-ethylxanthine, xanthine, indole, purine, isoindole, carbazole, quinoline, and isoquinoline.

The co-former may be selected from: 4,4-bipyridine, pyridoxine, deanol, 4-(2-hydroxyethyl)-morpholine, piperazine, theophylline, nicotinamide, isonicotinamide, tromethamine, tert-butyl amine and diethylamine.

Typically, the co-former is selected from theophylline, nicotinamide, isonicotinamide, and tromethamine.

The co-crystal may comprise psilocybin and a co-former which is 4,4-bipyridine. The co-crystal may comprise psilocybin and a co-former which is pyridoxine. The co-crystal may comprise psilocybin and a co-former which is deanol. The co-crystal may comprise psilocybin and a co-former which is 4-(2-hydroxyethyl)-morpholine. The co-crystal may comprise psilocybin and a co-former which is piperazine. The co-crystal may comprise psilocybin and a co-former which is theophylline. The co-crystal may comprise psilocybin and a co-former which is nicotinamide. The co-crystal may comprise psilocybin and a co-former which is isonicotinamide. The co-crystal may comprise psilocybin and a co-former which is tromethamine. The co-crystal may comprise psilocybin and a co-former which is tert-butyl amine. The co-crystal may comprise psilocybin and a co-former which is diethylamine.

Co-Crystals with a Neutral Compound

Also disclosed herein is a co-crystal comprising psilocybin and a co-former, wherein the co-former is a neutral compound. A neutral compound is: (i) a compound which is amphoteric; (ii) a compound which is zwitterionic; (iii) a compound which comprises neither an acidic moiety nor a basic moiety; or (iv) a compound which is an inorganic salt.

The co-former may be a compound which is amphoteric. The co-former may be a compound which is zwitterionic. Typically, the co-former is an amino acid or amino acid derivative.

The co-former may be selected from: DL-alanine, D-alanine, L-alanine, DL-arginine, D-arginine, L-arginine, DL-asparagine, D-asparagine, L-asparagine, DL-aspartic acid, D-aspartic acid, L-aspartic acid, DL-cysteine, D-cysteine, L-cysteine, DL-glutamine, D-glutamine, L-glutamine, DL-glutamic acid, D-glutamic acid, L-glutamic acid, glycine, DL-histidine, D-histidine, L-histidine, DL-isoleucine, D-isoleucine, L-isoleucine, DL-leucine, D-leucine, L-leucine, DL-lysine, D-lysine, L-lysine, DL-methionine, D-methionine, L-methionine, DL-phenylalanine, D-phenylalanine, L-phenylalanine, DL-proline, D-proline, L-proline, DL-serine, D-serine, L-serine, DL-threonine, D-threonine, L-threonine, DL-tryptophan, D-tryptophan, L-tryptophan, DL-tyrosine, D-tyrosine, L-tyrosine, DL-valine, D-valine, L-valine, DL-pyroglutamic acid, D-pyroglutamic acid, L-pyroglutamic acid, DL-selenocysteine, D-selenocysteine, L-selenocysteine, DL-pyrrolysine, D-pyrrolysine, L-pyrrolysine, N-formylmethionine, hydroxyproline, selenomethionine, carnitine, gamma-aminobutyric acid, levothyroxine, 2-aminoisobutyric acid, ornithine, citrulline and beta-alanine.

The co-former may be selected from: L-lysine, L-histidine, L-tyrosine, L-pyroglutamic acid, DL-cysteine, and L-glutamic acid.

Typically, the co-crystal is selected from L-pyroglutamic acid, DL-cysteine, and L-glutamic acid.

The co-former may be a compound which comprises neither an acidic moiety nor a basic moiety. Typically, the co-former is a compound which comprises one or more functional groups selected from: an ester moiety, an ether moiety, an alcohol moiety a phenol moiety, and a carboxamide moiety. Typically, the co-former is a compound which comprises an alcohol moiety and/or a phenol moiety. The co-former may be a compound which comprises an alcohol moiety. The co-former may be a compound which comprises a phenol moiety. The co-former may be a compound which comprises an ester moiety. The co-former may be a compound which comprises an ether moiety. The co-former may be a compound which comprises a carboxamide moiety.

The co-former may be selected from methyl nitrate, methyl formate, methyl acetate, methyl acrylate, methyl propionate, methyl butyrate, methyl pentanoate, methyl benzoate, methyl anthranilate, methyl salicylate, methyl phenylacetate, methyl cinnamate, ethyl formate, ethyl acetate, ethyl propionate, ethyl lactate, ethyl butyrate, ethyl pentanoate, ethyl isovalerate, ethyl hexanoate, ethyl heptanoate, ethyl benzoate, ethyl salicylate, ethyl octanoate, ethyl cinnamate, ethyl decanoate, propyl acetate, propyl propanoate, propyl hexanoate, allyl hexanoate, isopropyl acetate, isopropyl salicylate, isopropyl palmitate, butyl formate, butyl acetate, isobutyl formate, isobutyl acetate, sec-butyl formate, sec-butyl acetate, tert-butyl formate, tert-butyl acetate, butyl butyrate, amyl acetate, pentyl butyrate, pentyl propanoate, pentyl hexanoate, sec-amyl acetate, benzyl acetate, aspartame, ascorbyl palmitate, (ascorbic acid 6-hexadecanoate, including L-ascorbic acid 6-hexadecanoate and D-ascorbic acid 6-hexadecanoate), dimethyl ether, diethyl ether, dimethoxyethane, dioxane, tetrahydrofuran, anisole, crown ethers, polyethylene glycol, polypropylene glycol, maltol, ethyl maltol, meso-erythritol, threitol, mannitol (including D-mannitol, L-mannitol), sorbitol (including D-sorbitol, L-sorbitol, maltitol, xylitol (including D-xylitol, L-xylitol), inosine, phenol, 2-methylphenol, 3-methylphenol, 4-methylphenol, 2-ethylphenol, 3-ethylphenol, 4-ethylphenol, 2-propylphenol, 3-propylphenol, 4-propylphenol, 2-butylphenol, 3-butylphenol, 4-butylphenol, 2,6-dimethyl-4-methylphenol, 2,6-diethyl-4-methylphenol, 2,6-dipropyl-4-methylphenol, 2,6-di-tert-butyl-4-methylphenol, 2,6-dimethyl-4-ethylphenol, 2,6-diethyl-4-ethylphenol, 2,6-dipropyl-4-ethylphenol, 2,6-di-tert-butyl-4-ethylphenol, 2-tert-butyl-4-methylphenol, 2-tert-butyl-4-ethylphenol, 2,6-di-tert-butyl-4-ethylphenol, 2-methoxyphenol, 3-methoxyphenol, 4-methoxyphenol, 2-ethoxyphenol, 3-ethoxyphenol, 4-ethoxyphenol, 2-methyl-4-methoxyphenol, 2-methyl-3-methoxyphenol, 2-methyl-4-methoxyphenol, 2-methyl-3-ethoxyphenol, 2-methyl-4-ethoxyphenol, 2-tert-butyl-3-methoxyphenol, 2-tert-butyl-4-ethoxyphenol, 2-tert-butyl-3-ethoxyphenol, 2-sec-butyl-4-methoxyphenol, 2-sec-butyl-3-methoxyphenol, 2-sec-butyl-4-ethoxyphenol, 2-sec-butyl-3-ethoxyphenol, vanillin, ethyl vanillin, methylparaben (C$_1$ paraben), ethylparaben (C$_2$ paraben), propylparaben (C$_3$ paraben), butylparaben (C$_4$ paraben), propyl 3,4,5-trihydroxybenzoate (propyl gallate), ethyl 3,4,5-trihydroxybenzoate, methyl 3,4,5-trihydroxybenzoate and urea.

The co-former may be selected from: ethyl maltol, meso-erythritol, D-mannitol, D-sorbitol, D-xylitol, inosine, and L-ascorbic acid 6-hexadecanoate. The co-former may be selected from: 2,6-di-tert-butyl-4-methylphenol, 2-tert-butyl-4-methoxyphenol, vanillin, ethyl vanillin, C1-4 parabens, propyl gallate and urea.

Typically, the co-former is selected from: ethyl maltol, meso-erythritol, D-mannitol, D-sorbitol, D-xylitol, inosine, L-ascorbic acid 6-hexadecanoate, propyl gallate, 2,6-di-tert-butyl-4-methylphenol, 2-tert-butyl-4-methoxyphenol and urea.

The co-former may be a compound which is an inorganic salt.

The co-former may be selected from: calcium chloride, potassium dichromate, sodium chloride, sodium dihydrogen phosphate, sodium hydrogen phosphate, trisodium phosphate, calcium dihydrogen phosphate, calcium hydrogen phosphate, tricalcium phosphate, magnesium dihydrogen phosphate, magnesium hydrogen phosphate, trimagnesium phosphate, monopotassium phosphate, dipotassium phosphate, tripotassium phosphate, sodium bisulfate, sodium sulfate, calcium sulfate, magnesium sulfate, potassium sulfate, potassium bisulfate, sodium sulphite, calcium sulphite, magnesium sulphite, potassium sulphite, sodium bisulfite, calcium bisulfite, magnesium bisulfite, potassium bisulfite, acesulfame potassium, acesulfame sodium, and sodium formaldehyde sulfoxylate.

The co-former may be selected from: sodium dihydrogen phosphate, sodium bisulfite, acesulfame potassium and sodium formaldehyde sulfoxylate.

Typically the co-former is selected from: sodium bisulfite, acesulfame potassium, and sodium formaldehyde sulfoxylate.

The co-crystal may comprise psilocybin and a co-former which is L-lysine. The co-crystal may comprise psilocybin and a co-former which is L-histidine. The co-crystal may comprise psilocybin and a co-former which is L-tyrosine. The co-crystal may comprise psilocybin and a co-former which is L-pyroglutamic acid. The co-crystal may comprise psilocybin and a co-former which is DL-cysteine. The co-crystal may comprise psilocybin and a co-former which is L-glutamic acid. The co-crystal may comprise psilocybin and a co-former which is ethyl maltol. The co-crystal may comprise psilocybin and a co-former which is meso-erythritol. The co-crystal may comprise psilocybin and a co-former which is D-mannitol. The co-crystal may comprise psilocybin and a co-former which is D-sorbitol. The co-crystal may comprise psilocybin and a co-former which is D-xylitol. The co-crystal may comprise psilocybin and a co-former which is inosine. The co-crystal may comprise psilocybin and a co-former which is L-ascorbic acid 6-hexadecanoate. The co-crystal may comprise psilocybin and a co-former which is 2,6-di-tert-butyl-4-methylphenol. The co-crystal may comprise psilocybin and a co-former which is 2-tert-butyl-4-methoxyphenol. The co-crystal may comprise psilocybin and a co-former which is vanillin. The co-crystal may comprise psilocybin and a co-former which is ethyl vanillin. The co-crystal may comprise psilocybin and a co-former which is C$_{1-4}$ parabens. The co-crystal may comprise psilocybin and a co-former which is propyl gallate. The co-crystal may comprise psilocybin and a co-former which is urea. The co-crystal may comprise psilocybin and a co-former which is sodium dihydrogen phosphate. The co-crystal may comprise psilocybin and a co-former which is sodium bisulfite. The co-crystal may comprise psilocybin and a co-former which is acesulfame potassium. The co-crystal may comprise psilocybin and a co-former which is sodium formaldehyde sulfoxylate.

The co-crystal may comprise one or more additional co-formers. Typically, however, the co-crystal comprises a single co-former.

The co-former typically is a compound having a molar mass of no greater than 500 g/mol, no greater than 350 g/mol or no greater than 200 g/mol. The co-former may have a molar mass of at least 30 g/mol, at least 50 g/mol or at least 100 g/mol.

A co-former may contain one or more chiral centres. Unless otherwise specified, references herein to a co-former encompass all enantiomeric and diastereomeric forms of the co-former, mixtures thereof (e.g. racemic mixtures) and enantiomerically and diastereomerically pure forms thereof.

Stoichiometry

The molar ratio of psilocybin:co-former in the co-crystal may be from 1:0.25 to 1:6, for example 1:0.25 to 1:4. The molar ratio of psilocybin:co-former may be from 1:0.25 to 1:3, or from 1:0.5 to 1:3, or from 1:0.5 to 1:2, or from 1:0.5 to 1:1.5. Typically, the molar ratio of psilocybin:co-former in the co-crystal is from 1:0.5 to 1:3, or from 1:0.5 to 1:2.

The molar ratio of psilocybin:co-former in the co-crystal may be about 1:0.25, about 1:0.5, about 1:0.75, about 1:1, about 1:1.25, about 1:1.5, about 1:1.75, about 1:2, about 1:2.5, about 1:3, about 1:3.5, about 1:4, about 1:4.5, about 1:5, about 1:5.5 or about 1:6. Typically, the molar ratio of psilocybin:co-former in the co-crystal is about 1:0.5, about 1:1, or about 1:2. The molar ratio of psilocybin:co-former in the co-crystal may be 1:0.5, for instance 1.0:0.50. The molar ratio of psilocybin:co-former in the co-crystal may be 1:1, for instance 1.0:1.0. The molar ratio of psilocybin:co-former in the co-crystal may be 1:2, for instance 1.0:2.0.

If the co-crystal comprises more than one co-former, the molar ratio of psilocybin to each co-former may be as defined above. Alternatively, the molar ratio of psilocybin to the total amount of co-former may be as defined above.

As used herein, the term "about" means any value that the skilled person would appreciate is a reasonable variation of the value that is referred to by the term "about". Typically, "about" means±10% or ±5%.

In one embodiment, the co-crystal is a co-crystal comprising psilocybin and citric acid, wherein the molar ratio of psilocybin:citric acid is 1:1. Alternatively, the co-crystal may be a co-crystal comprising psilocybin and citric acid, wherein the molar ratio of psilocybin:citric acid is 1:0.5. Alternatively, the co-crystal may be a co-crystal comprising psilocybin and citric acid, wherein the molar ratio of psilocybin:citric acid is 1:2.

In one embodiment, the co-crystal is a co-crystal comprising psilocybin and fumaric acid, wherein the molar ratio of psilocybin:fumaric acid is 1:1. Alternatively, the co-crystal may be a co-crystal comprising psilocybin and fumaric acid, wherein the molar ratio of psilocybin:fumaric acid is 1:0.5. Alternatively, the co-crystal may be a co-crystal comprising psilocybin and fumaric acid, wherein the molar ratio of psilocybin:fumaric acid is 1:2.

In one embodiment, the co-crystal is a co-crystal comprising psilocybin and succinic acid, wherein the molar ratio of psilocybin:succinic acid is 1:1. Alternatively, the co-crystal may be a co-crystal comprising psilocybin and succinic acid, wherein the molar ratio of psilocybin:succinic acid is 1:0.5. Alternatively, the co-crystal may be a co-crystal comprising psilocybin and succinic acid, wherein the molar ratio of psilocybin:succinic acid is 1:2.

In one embodiment, the co-crystal is a co-crystal comprising psilocybin and gluconic acid, wherein the molar ratio of psilocybin:gluconic acid is 1:1. Alternatively, the co-crystal may be a co-crystal comprising psilocybin and gluconic acid, wherein the molar ratio of psilocybin:gluconic acid is 1:0.5. Alternatively, the co-crystal may be a co-crystal comprising psilocybin and gluconic acid, wherein the molar ratio of psilocybin:gluconic acid is 1:2.

In one embodiment, the co-crystal is a co-crystal comprising psilocybin and L-tartaric acid, wherein the molar ratio of psilocybin:L-tartaric acid is 1:1. Alternatively, the co-crystal may be a co-crystal comprising psilocybin and L-tartaric acid, wherein the molar ratio of psilocybin:L-tartaric acid is 1:0.5. Alternatively, the co-crystal may be a co-crystal comprising psilocybin and L-tartaric acid, wherein the molar ratio of psilocybin:L-tartaric acid is 1:2.

In one embodiment, the co-crystal is a co-crystal comprising psilocybin and L-ascorbic acid, wherein the molar ratio of psilocybin:L-ascorbic acid is 1:1.

Alternatively, the co-crystal may be a co-crystal comprising psilocybin and L-ascorbic acid, wherein the molar ratio of psilocybin:L-ascorbic acid is 1:0.5. Alternatively, the co-crystal may be a co-crystal comprising psilocybin and L-ascorbic acid, wherein the molar ratio of psilocybin:L-ascorbic acid is 1:2.

In one embodiment, the co-crystal is a co-crystal comprising psilocybin and L-lactic acid, wherein the molar ratio of psilocybin:L-lactic acid is 1:1. Alternatively, the co-crystal may be a co-crystal comprising psilocybin and L-lactic acid, wherein the molar ratio of psilocybin:L-lactic acid is 1:0.5. Alternatively, the co-crystal may be a co-crystal comprising psilocybin and L-lactic acid, wherein the molar ratio of psilocybin:L-lactic acid is 1:2.

In one embodiment, the co-crystal is a co-crystal comprising psilocybin and saccharin, wherein the molar ratio of psilocybin:saccharin is 1:1. Alternatively, the co-crystal may be a co-crystal comprising psilocybin and saccharin, wherein the molar ratio of psilocybin:saccharin is 1:0.5. Alternatively, the co-crystal may be a co-crystal comprising psilocybin and saccharin, wherein the molar ratio of psilocybin:saccharin is 1:2.

In one embodiment, the co-crystal is a co-crystal comprising psilocybin and disodium EDTA, wherein the molar ratio of psilocybin:disodium EDTA is 1:1. Alternatively, the co-crystal may be a co-crystal comprising psilocybin and disodium EDTA, wherein the molar ratio of psilocybin:disodium EDTA is 1:0.5. Alternatively, the co-crystal may be a co-crystal comprising psilocybin and disodium EDTA, wherein the molar ratio of psilocybin:disodium EDTA is 1:2.

In one embodiment, the co-crystal is a co-crystal comprising psilocybin and nicotinic acid, wherein the molar ratio of psilocybin:nicotinic acid is 1:1. Alternatively, the co-crystal may be a co-crystal comprising psilocybin and nicotinic acid, wherein the molar ratio of psilocybin:nicotinic acid is 1:0.5. Alternatively, the co-crystal may be a co-crystal comprising psilocybin and nicotinic acid, wherein the molar ratio of psilocybin:nicotinic acid is 1:2.

In one embodiment, the co-crystal is a co-crystal comprising psilocybin and theophylline, wherein the molar ratio of psilocybin:theophylline is 1:1. Alternatively, the co-crystal may be a co-crystal comprising psilocybin and theophylline, wherein the molar ratio of psilocybin:theophylline is 1:0.5. Alternatively, the co-crystal may be a co-crystal comprising psilocybin and theophylline, wherein the molar ratio of psilocybin:theophylline is 1:2.

In one embodiment, the co-crystal is a co-crystal comprising psilocybin and nicotinamide, wherein the molar ratio of psilocybin:nicotinamide is 1:1. Alternatively, the co-crystal may be a co-crystal comprising psilocybin and nicotinamide, wherein the molar ratio of psilocybin:nicotinamide is 1:0.5. Alternatively, the co-crystal may be a co-crystal comprising psilocybin and nicotinamide, wherein the molar ratio of psilocybin:nicotinamide is 1:2.

In one embodiment, the co-crystal is a co-crystal comprising psilocybin and isonicotinamide, wherein the molar ratio of psilocybin:isonicotinamide is 1:1.

Alternatively, the co-crystal may be a co-crystal comprising psilocybin and isonicotinamide, wherein the molar ratio of psilocybin:isonicotinamide is 1:0.5.

Alternatively, the co-crystal may be a co-crystal comprising psilocybin and isonicotinamide, wherein the molar ratio of psilocybin:isonicotinamide is 1:2.

In one embodiment, the co-crystal is a co-crystal comprising psilocybin and tromethamine, wherein the molar ratio of psilocybin:tromethamine is 1:1.

Alternatively, the co-crystal may be a co-crystal comprising psilocybin and tromethamine, wherein the molar ratio of psilocybin:tromethamine is 1:0.5.

Alternatively, the co-crystal may be a co-crystal comprising psilocybin and tromethamine, wherein the molar ratio of psilocybin:tromethamine is 1:2.

In one embodiment, the co-crystal is a co-crystal comprising psilocybin and L-pyroglutamic acid, wherein the molar ratio of psilocybin:L-pyroglutamic acid is 1:1.

Alternatively, the co-crystal may be a co-crystal comprising psilocybin and L-pyroglutamic acid, wherein the molar ratio of psilocybin:L-pyroglutamic acid is 1:0.5.

Alternatively, the co-crystal may be a co-crystal comprising psilocybin and L-pyroglutamic acid, wherein the molar ratio of psilocybin:L-pyroglutamic acid is 1:2.

In one embodiment, the co-crystal is a co-crystal comprising psilocybin and DL-cysteine, wherein the molar ratio of psilocybin:DL-cysteine is 1:1. Alternatively, the co-crystal may be a co-crystal comprising psilocybin and DL-cysteine, wherein the molar ratio of psilocybin:DL-cysteine is 1:0.5. Alternatively, the co-crystal may be a co-crystal comprising psilocybin and DL-cysteine, wherein the molar ratio of psilocybin:DL-cysteine is 1:2.

In one embodiment, the co-crystal is a co-crystal comprising psilocybin and L-glutamic acid, wherein the molar ratio of psilocybin:L-glutamic acid is 1:1.

Alternatively, the co-crystal may be a co-crystal comprising psilocybin and L-glutamic acid, wherein the molar ratio of psilocybin:L-glutamic acid is 1:0.5. Alternatively, the co-crystal may be a co-crystal comprising psilocybin and L-glutamic acid, wherein the molar ratio of psilocybin:L-glutamic acid is 1:2.

In one embodiment, the co-crystal is a co-crystal comprising psilocybin and ethyl maltol, wherein the molar ratio of psilocybin:ethyl maltol is 1:1. Alternatively, the co-crystal may be a co-crystal comprising psilocybin and ethyl maltol, wherein the molar ratio of psilocybin:ethyl maltol is 1:0.5. Alternatively, the co-crystal may be a co-crystal comprising psilocybin and ethyl maltol, wherein the molar ratio of psilocybin:ethyl maltol is 1:2.

In one embodiment, the co-crystal is a co-crystal comprising psilocybin and meso-erythritol, wherein the molar ratio of psilocybin:meso-erythritol is 1:1. Alternatively, the co-crystal may be a co-crystal comprising psilocybin and meso-erythritol, wherein the molar ratio of psilocybin:meso-erythritol is 1:0.5. Alternatively, the co-crystal may be a co-crystal comprising psilocybin and meso-erythritol, wherein the molar ratio of psilocybin:meso-erythritol is 1:2.

In one embodiment, the co-crystal is a co-crystal comprising psilocybin and D-mannitol, wherein the molar ratio of psilocybin:D-mannitol is 1:1. Alternatively, the co-crystal may be a co-crystal comprising psilocybin and D-mannitol, wherein the molar ratio of psilocybin:D-mannitol is 1:0.5. Alternatively, the co-crystal may be a co-crystal comprising psilocybin and D-mannitol, wherein the molar ratio of psilocybin:D-mannitol is 1:2.

In one embodiment, the co-crystal is a co-crystal comprising psilocybin and D-sorbitol, wherein the molar ratio of psilocybin:D-sorbitol is 1:1. Alternatively, the co-crystal may be a co-crystal comprising psilocybin and D-sorbitol, wherein the molar ratio of psilocybin:D-sorbitol is 1:0.5. Alternatively, the co-crystal may be a co-crystal comprising psilocybin and D-sorbitol, wherein the molar ratio of psilocybin:D-sorbitol is 1:2.

In one embodiment, the co-crystal is a co-crystal comprising psilocybin and D-xylitol, wherein the molar ratio of psilocybin:D-xylitol is 1:1. Alternatively, the co-crystal may be a co-crystal comprising psilocybin and D-xylitol, wherein the molar ratio of psilocybin:D-xylitol is 1:0.5. Alternatively, the co-crystal may be a co-crystal comprising psilocybin and D-xylitol, wherein the molar ratio of psilocybin:D-xylitol is 1:2.

In one embodiment, the co-crystal is a co-crystal comprising psilocybin and inosine, wherein the molar ratio of psilocybin:inosine is 1:1. Alternatively, the co-crystal may be a co-crystal comprising psilocybin and inosine, wherein the molar ratio of psilocybin:inosine is 1:0.5. Alternatively, the co-crystal may be a co-crystal comprising psilocybin and inosine, wherein the molar ratio of psilocybin:inosine is 1:2.

In one embodiment, the co-crystal is a co-crystal comprising psilocybin and L-ascorbic acid 6-hexadecanoate, wherein the molar ratio of psilocybin:L-ascorbic acid 6-hexadecanoate is 1:1. Alternatively, the co-crystal may be a co-crystal comprising psilocybin and L-ascorbic acid 6-hexadecanoate, wherein the molar ratio of psilocybin:L-ascorbic acid 6-hexadecanoate is 1:0.5. Alternatively, the co-crystal may be a co-crystal comprising psilocybin and L-ascorbic acid 6-hexadecanoate, wherein the molar ratio of psilocybin:L-ascorbic acid 6-hexadecanoate is 1:2.

In one embodiment, the co-crystal is a co-crystal comprising psilocybin and propyl gallate, wherein the molar ratio of psilocybin:propyl gallate is 1:1. Alternatively, the co-crystal may be a co-crystal comprising psilocybin and propyl gallate, wherein the molar ratio of psilocybin:propyl gallate is 1:0.5. Alternatively, the co-crystal may be a co-crystal comprising psilocybin and propyl gallate, wherein the molar ratio of psilocybin:propyl gallate is 1:2.

In one embodiment, the co-crystal is a co-crystal comprising psilocybin and 2,6-di-tert-butyl-4-methylphenol, wherein the molar ratio of psilocybin:2,6-di-tert-butyl-4-methylphenol is 1:1. Alternatively, the co-crystal may be a co-crystal comprising psilocybin and 2,6-di-tert-butyl-4-methylphenol, wherein the molar ratio of psilocybin:2,6-di-tert-butyl-4-methylphenol is 1:0.5. Alternatively, the co-crystal may be a co-crystal comprising psilocybin and 2,6-di-tert-butyl-4-methylphenol, wherein the molar ratio of psilocybin:2,6-di-tert-butyl-4-methylphenol is 1:2.

In one embodiment, the co-crystal is a co-crystal comprising psilocybin and 2-tert-butyl-4-methoxyphenol, wherein the molar ratio of psilocybin:2-tert-butyl-4-methoxyphenol is 1:1. Alternatively, the co-crystal may be a co-crystal comprising psilocybin and 2-tert-butyl-4-methoxyphenol, wherein the molar ratio of psilocybin:2-tert-butyl-4-methoxyphenol is 1:0.5. Alternatively, the co-crystal may be a co-crystal comprising psilocybin and 2-tert-butyl-4-methoxyphenol, wherein the molar ratio of psilocybin:2-tert-butyl-4-methoxyphenol is 1:2.

In one embodiment, the co-crystal is a co-crystal comprising psilocybin and urea, wherein the molar ratio of psilocybin:urea is 1:1. Alternatively, the co-crystal may be a co-crystal comprising psilocybin and urea, wherein the molar ratio of psilocybin:urea is 1:0.5. Alternatively, the co-crystal may be a co-crystal comprising psilocybin and urea, wherein the molar ratio of psilocybin:urea is 1:2.

In one embodiment, the co-crystal is a co-crystal comprising psilocybin and sodium bisulfite, wherein the molar ratio of psilocybin:sodium bisulfite is 1:1. Alternatively, the co-crystal may be a co-crystal comprising psilocybin and sodium bisulfite, wherein the molar ratio of psilocybin:sodium bisulfite is 1:0.5. Alternatively, the co-crystal may be a co-crystal comprising psilocybin and sodium bisulfite, wherein the molar ratio of psilocybin:sodium bisulfite is 1:2.

In one embodiment, the co-crystal is a co-crystal comprising psilocybin and acesulfame potassium, wherein the molar ratio of psilocybin:acesulfame potassium is 1:1. Alternatively, the co-crystal may be a co-crystal comprising psilocybin and acesulfame potassium, wherein the molar ratio of psilocybin:acesulfame potassium is 1:0.5. Alternatively, the co-crystal may be a co-crystal comprising psilocybin and acesulfame potassium, wherein the molar ratio of psilocybin:acesulfame potassium is 1:2.

In one embodiment, the co-crystal is a co-crystal comprising psilocybin and sodium formaldehyde sulfoxylate, wherein the molar ratio of psilocybin:sodium formaldehyde sulfoxylate is 1:1. Alternatively, the co-crystal may be a co-crystal comprising psilocybin and sodium formaldehyde sulfoxylate, wherein the molar ratio of psilocybin:sodium formaldehyde sulfoxylate is 1:0.5. Alternatively, the co-crystal may be a co-crystal comprising psilocybin and sodium formaldehyde sulfoxylate, wherein the molar ratio of psilocybin:sodium formaldehyde sulfoxylate is 1:2.

Solvates and Hydrates

The co-crystal may be in the form of a solvate. The term "solvate" as used herein describes a co-crystals that have solvent molecules (typically organic solvents) incorporated into their co-crystal lattice. As such, the co-crystal solvate comprises the active agent, the co-former and the solvent molecules. A solvate may contain molecules of organic solvent and water. A hydrate is a solvate which contains incorporated water molecules as the only solvent molecules.

The solvate is typically a solvate with an organic solvent. Suitable organic solvents are known to the person skilled in the art. For example, the organic solvent may be carbon tetrachloride, 1,2-dichloroethane, 1,1-dichloroethane, 1,1,1-trichloroethane, acetonitrile, chlorobenzene, chloroform, cumene, cyclohexane, cyclopentyl methyl ether, 1,2-dichloroethene, dichloromethane, 1,2-dimethoxyethane, N,N-dimethylacetamide, N,N-dimethylformamide, 1,4-dioxane, 2-ethoxyethanol, ethyleneglycol, formamide, hexane, methanol, 2-methoxyethanol, methylbutyl ketone, methylcyclohexane, methylisobutylketone, N-methylpyrrolidone, nitromethane, pyridine, sulfolane, t-butyl alcohol, tetrahydrofuran, tetralin, toluene, 1,1,2-trichloroethene, xylene, acetic acid, acetone, anisole, 1-butanol, 2-butanol, butyl acetate, t-butyl methyl ether, dimethyl sulfoxide, ethanol, ethyl acetate, ethyl ether, ethyl formate, formic acid, heptane, isobutyl acetate, isopropyl acetate, methyl acetate, 3-methyl-1-butanol, methylethyl ketone, 2-methyl-1-propanol, 2-methyltetrahydrofuran, pentane, 1-pentanol, 1-propanol, 2-propanol, propyl acetate, triethylamine, 1,1-diethoxypropane, 1,1-dimethoxymethane, 2,2-dimethoxypropane, isooctane, isopropyl ether, methylisopropyl ketone, 2-methyltetrahydrofuran, petroleum ether, trichloroacetic acid, 2,2,2-trifluoroethanol, 1,1,1,3,3,3-hexafluoropropan-2-ol, (trifluoromethyl)benzene or trifluoroacetic acid.

Typically, the organic solvent is selected from: acetonitrile, chlorobenzene, chloroform, cumene, cyclohexane, cyclopentyl methyl ether, 1,2-dichloroethene, dichloromethane, 1,2-dimethoxyethane, N,N-dimethylacetamide, N,N-dimethylformamide, 1,4-dioxane, 2-ethoxyethanol, ethyleneglycol, formamide, hexane, methanol, 2-methoxyethanol, methylbutyl ketone, methylcyclohexane, methylisobutylketone, N-methylpyrrolidone, nitromethane, pyridine, sulfolane, t-butyl alcohol, tetrahydrofuran, tetralin, toluene, 1,1,2-trichloroethene, xylene, acetic acid, acetone, anisole, 1-butanol, 2-butanol, butyl acetate, t-butyl methyl ether, dimethyl sulfoxide, ethanol, ethyl acetate, ethyl ether, ethyl formate, formic acid, heptane, isobutyl acetate, isopropyl acetate, methyl acetate, 3-methyl-1-butanol, methylethyl ketone, 2-methyl-1-propanol, 2-methyltetrahydrofuran, pentane, 1-pentanol, 1-propanol, 2-propanol, propyl acetate, triethylamine, 1,1-diethoxypropane, 1,1-dimethoxymethane, 2,2-dimethoxypropane, isooctane, isopropyl ether, methylisopropyl ketone, 2-methyltetrahydrofuran, petroleum ether, 2,2,2-trifluoroethanol, 1,1,1,3,3,3-hexafluoropropan-2-ol, (trifluoromethyl)benzene, trichloroacetic acid, and trifluoroacetic acid.

Typically, the organic solvent is a pharmaceutically acceptable organic solvent.

The co-crystal may be in the form a hydrate. Alternatively, the co-crystal may be in the form of a non-hydrate. The co-crystal may be anhydrous.

The solvate and/or hydrate may be stoichiometric, i.e. have a molar ratio of co-crystal:solvent of 1:1. Alternatively, the solvate and/or hydrate may be non-stoichiometric, i.e. have a non-integer molar ratio of co-crystal:solvent, for example 1:1.1. A non-stoichiometric solvate and/or hydrate may also be known as a channel solvate and/or hydrate.

Process for Producing Co-Crystals

The process for producing a co-crystal as described herein comprises combining psilocybin and a co-former, for example a co-former which is an acid, a base or a neutral compound. Suitable methods are well known to the person skilled in the art.

The process may comprise reactive crystallisation. Reactive crystallisation typically comprises combining a solution of psilocybin with a solution of the co-former, stirring, and isolating the resulting co-crystal.

The process may comprise crystallisation. Crystallisation typically comprises dissolving psilocybin and the co-former (either directly or via mechanical grinding) in a solvent or solvent system to yield a clear solution, allowing supersaturation, and isolating the resulting co-crystal.

The process may comprise slurry or suspension mediated crystallisation. Slurry or suspension mediated crystallisation typically comprises suspending psilocybin and the co-former in a solvent or solvent system such that a small fraction remains in excess, stirring the suspension, and isolating the resulting co-crystal.

The process may comprise solid state grinding. Solid state grinding typically comprises grinding psilocybin and the co-former together, and isolating the resulting co-crystal.

The process may comprise liquid assisted grinding. Liquid assisted grinding typically comprises mixing psilocybin and the co-former in a small volume (typically, but not confined to, 1:4 volume:weight ratio of total solid) of a solvent/solvent system, grinding the psilocybin with the co-former (including grinding using a resonant acoustic mixer), and isolating the resulting co-crystal.

The process may comprise a solid state mediated process. A solid state mediated process typically comprises mixing psilocybin and the co-former, and either exposing to laser irradiation or an electrochemical source, then isolating the resulting co-crystal.

The process may comprise melt mediated crystallisation. Melt mediated crystallisation typically comprises simultaneously mixing the psilocybin and co-former and melting the psilocybin and co-former, and isolating the resulting co-crystal.

Pharmaceutical Compositions

The present invention provides a pharmaceutical composition comprising the co-crystal and a pharmaceutically acceptable excipient or diluent. The co-crystal may be as further defined herein.

An appropriate conventional excipient or diluent will depend on the mode of administration used. Pharmaceutically acceptable excipients and diluents are well known to the skilled person. The pharmaceutical composition may further comprise one or more of a buffer, a lubricant, a diluent, or a carrier.

Methods of Treatment

The co-crystal of the invention may be useful as a medicament. In one embodiment, the invention provides a co-crystal as described herein for use as a medicine.

In one embodiment, the invention provides a method of treating or preventing a disease or condition selected from psychological, neurological and central nervous system disorders.

The disease or condition may be selected from: disruptive mood dysregulation disorder, depression, major depressive disorder (MDD), treatment-resistant depression, persistent depressive disorder (dysthymia), demoralization, hopelessness, premenstrual dysphoric disorder, substance/medication-induced depressive disorder, post-partum depression, depressive disorder due to another medical condition, separation anxiety disorder, selective mutism, specific phobia, social anxiety disorder (social phobia), panic disorder, panic attack, agoraphobia, generalized anxiety disorder, anxiety, death anxiety, substance-medication-induced anxiety disorder, anxiety disorder due to another medical condition, somatic symptom disorder, illness anxiety disorder (hypochondriac), conversion disorder (functional neurological symptom disorder), factitious disorder, post-traumatic stress disorder (PTSD), adjustment disorders, acute distress disorder, obsessive-compulsive disorder, body dysmorphic disorder, hoarding disorder, trichotillomania (hair-pulling) disorder, excoriation (skin-picking) disorder, substance/medication-induced obsessive-compulsive and related disorder, obsessive-compulsive and related disorder due to another medical condition, substance-related disorders, alcohol-related disorders, cannabis-related disorders, hallucinogen-related disorders, inhalant-related disorders, cocaine-related disorders, opioid-related disorders, sedative-, hypnotic-, or anxiolytic-related disorders, stimulant-related disorders, tobacco-related disorders, non-substance-related disorders (gambling or gaming disorder), migraines, cluster headaches (including chronic cluster headaches), cyclical vomiting, tension-type headache, dysphasia, pica, anorexia nervosa, bulimia nervosa, binge-eating disorder, oppositional defiant disorder, intermittent explosive disorder, conduct disorder, antisocial personality disorder, psychopathy, pyromania, kleptomania, autism spectrum disorder, antisocial personality disorder, attention-deficit/ hyperactivity disorder, schizotypal (personality) disorder, delusional disorder, schizophrenia, schizoaffective disorder, insomnia disorder, hypersomnolence disorder, narcolepsy, primary central sleep apnea, bipolar I disorder, bipolar II disorder, cyclothymic disorder, pain, phantom pain, chronic pain, myelopathy, traumatic brain injury, intellectual disabilities, mania, neurodegeneration, paraphilic disorders (e.g, paedophilic disorder), suicidal behavior disorder, suicidal ideation, desire for hastened death, non-suicidal self-injury, persistent complex bereavement disorder, epilepsy, locked-in syndrome and restless leg syndrome.

In one embodiment, the method is a method of treating or preventing a disease or condition selected from depression, anxiety, death anxiety, demoralization, adjustment disorders, hopelessness, suicidal ideation and desire for hastened death.

In one embodiment, the method is a method of treating or preventing cocaine-related disorders, opioid-related disorders, or stimulant-related disorders.

The method may be a method of treating or preventing depression in a patient. The method may be a method of treating or preventing anxiety in a patient. As used herein, treating or preventing depression and/or anxiety includes reducing the symptoms of depression and/or anxiety or achieving remission of depression and/or anxiety. In one embodiment, treating or preventing depression and/or anxiety comprises reducing the symptoms of depression and/or anxiety. The patient may report a reduction of symptoms of depression and/or anxiety.

In one embodiment, the patient has been identified as being in need of treatment to alleviate depression and/or anxiety. In one embodiment, the patient has indicated that he or she is suffering from depression and/or anxiety.

The symptoms of depression and/or anxiety may be measured using the Hospital Anxiety and Depression Scale (HADS; Zigmond and Snaith (1983), "The hospital anxiety and depression Scale", *Acta Psychiatrica Scand,* 67: 361-370). In this test, lower numbers indicate lower levels of depression and/or anxiety. Subscale scores can be calculated for depression (HADS-D) and anxiety (HADS-A). A subscale score equal to or above 8 and a full scale score over 12 indicates the possible presence of a clinical disorder.

Accordingly, in the method of the invention a total Hospital Anxiety and Depression Scale score of the patient may be reduced after administration of the co-crystal. In one embodiment, the total HADS score of the patient is reduced to below about 12 after administration of the co-crystal.

The severity of depression may also be measured using the Beck Depression Inventory-II (BDI-II; Beck et al (1988), "Psychometric properties of the Beck Depression Inventory: Twenty-five years of evaluation", *Clin Psych Rev,* 8: 77-100). Scores above 12 indicate possible clinical depression.

Accordingly, in the method of the invention a Beck Depression Inventory-II score of the patient may be reduced after administration of the co-crystal. In one embodiment, the Beck Depression Inventory-II score of the patient is reduced to below about 12 after administration of the co-crystal.

The method may be a method of treating or preventing death anxiety. The method may be a method of treating or preventing demoralization (i.e. loss of meaning in life). The method may be a method of treating or preventing hopelessness. Death anxiety, demoralization and hopelessness are aspects of existential distress. Thus, the method may also be a method of treating or preventing existential distress in a patient, wherein treating or preventing existential distress includes reducing levels of at least one of death anxiety, hopelessness and demoralization.

In the method of treating or preventing death anxiety in a patient, death anxiety is reduced relative to the death anxiety of the patient before the administration of the co-crystal. Death anxiety is typically measured according to the Death Anxiety Scale (Templer (1970), "The construction and validation of a death anxiety scale", *J Gen Psychol,* 82: 165-177). Scores below 8 are considered normative levels of death anxiety. Accordingly, in the method of the invention a death anxiety score of the patient may be reduced to less than 8 after administration of the co-crystal.

In the method of treating or preventing demoralization in a patient, demoralization is reduced relative to the demoralization of the patient before the administration of the co-crystal. Demoralization is typically measured according to the Demoralization Scale (Kissane et al. (2004), "The demoralization scale: A report of its development and preliminary validation", *J Palliat Care,* 20: 269-276). Scores above 30 are considered indicative of clinical levels of demoralization. Accordingly, in the method of the invention a demoralization score of the patient may be reduced to less than 30 after administration of the co-crystal.

In the method of treating or preventing hopelessness in a patient, hopelessness is reduced relative to the hopelessness of the patient before the administration of the co-crystal. Hopelessness is typically measured according to the Hopelessness Assessment in Illness instrument (Rosenfeld et al. (2011), "Assessing hopelessness in terminally ill cancer patients: Development of the Hopelessness Assessment in Illness Questionnaire", *Psychol Assess,* 23: 325-336), on a scale of 0-16. Higher scores indicate higher levels of hopelessness. Accordingly, in the method of the invention a Hopelessness Assessment in Illness score of the patient may be reduced to less than 8 after administration of the co-crystal.

The method may be a method of treating or preventing suicidal ideation in a patient. As used herein, treating or preventing suicidal ideation includes reducing or preventing suicidal thinking, suicidal planning and/or suicide attempts. The patient may report a reduction in suicidal thinking and/or suicidal planning. The patient may make less frequent suicide attempts.

In one embodiment, the patient has been identified as being in need of treatment to prevent or reduce suicidal ideation. Accordingly, the method of the invention may include a step of assessing the level of suicidal ideation in the patient prior to administering the co-crystal to said patient. In one embodiment, the patient has indicated that he or she is suffering from suicidal ideation.

Suicidal ideation may be measured using a composite test comprising elements from the Beck Depression Inventory-II (BDI-II; Beck et al (1988), "Psychometric properties of the Beck Depression Inventory: Twenty-five years of evaluation", *Clin Psych Rev,* 8: 77-100) and the Brief Symptom Inventory (BSI; Derogatis 1993). In the BDI, Item #9 queries suicidal ideation with the following options: 0=I don't have any thoughts of killing myself; 1=I have thoughts of killing myself, but I would not carry them out; 2=I would like to kill myself; 3=I would kill myself if I had the chance. In the BSI, item #9 ("Thoughts of ending your life") also correlates to suicidal ideation, and is measured on a Likert scale: 0=Not at all; 1=Little; 2=Moderately; 3=Quite a bit; 4=Extremely. The aggregate composite suicidal ideation score is calculated by adding the scores from BDI-II item #9 to BSI Item #9. The composite score may be calculated by computing Z-scores for each item and summing them, and then the composite Z-scores may be transformed into standardized T-scores with a range of 0 to 100 (Song et al., 2013). Higher scores indicate higher suicidal ideation.

Accordingly, in the method of the invention a composite suicidal ideation score of the patient may be reduced after administration of the co-crystal. Typically, a composite suicidal ideation score of the patient is reduced by at least 20%, at least 30%, at least 40%, at least 50% or at least 75% after administration of the co-crystal. In one embodiment, a composite suicidal ideation score of the patient after administration of the co-crystal is less than 50, less than 45 or less than 40.

The method may be a method of treating or preventing desire for hastened death in a patient. As used herein, treating or preventing desire for hastened death includes preventing or reducing the desire for a more rapid death than would naturally occur. The patient may report a reduction in desire for a more rapid death than would naturally occur.

In one embodiment, the patient has been identified as being in need of treatment to prevent or reduce desire for hastened death. Accordingly, the method of the invention may include a step of assessing the level of desire for hastened death in the patient prior to administering the co-crystal to said patient. In one embodiment, the patient has indicated that he or she is suffering from desire for hastened death.

Desire for hastened death may be measured using the schedule of attitudes towards hastened death (SAHD) (Rosenfeld 2000). The SAHD is a 20-item true/false measure of desire for hastened death, which has been validated in patients with cancer. Alternatively, DHD can be measured using the loss of meaning factor from the Demoralization Scale (Kissane et al. (2004)). In particular, a composite desire for hastened death score can be created from the following five items from the loss of meaning factor, as measured on a Likert scale from zero to four: "Life is no longer worth living", "I would rather not be alive", "My life seems to be pointless", "My role in life has been lost", and "There is no purpose to the activities in my life".

Accordingly, in the method of the invention a composite desire for hastened death score of the patient may be reduced after administration of the co-crystal. Typically, a composite desire for hastened death score of the patient is reduced by at least 20%, at least 40%, at least 60% or at least 80% after administration of the co-crystal.

The method of the invention comprises administering a therapeutically effective amount of a co-crystal as defined herein to the patient. The therapeutically effective amount may be any amount of co-crystal which contains an amount of psilocybin that is effective in treating and/or preventing a disease or condition as described herein. An effective amount of psilocybin may be from about 0.001 mg/kg to about 10 mg/kg, for instance from about 0.01 mg/kg to about 1 mg/kg, where mg/kg is mg per kg of the patient's body weight at the time of the administration of the co-crystal. Typically, an effective amount of psilocybin may be a dose of from about 0.1 mg/kg to about 0.5 mg/kg, or from about 0.2 mg/kg to about 0.4 mg/kg. In one embodiment, the effective amount of psilocybin is about 0.3 mg/kg.

In the method of the invention, the therapeutically effective amount of the co-crystal may be administered as a single dose or as multiple doses. Typically, the therapeutically effective amount of the co-crystal is administered as a single dose.

A single dose of the co-crystal may contain from about 0.1 to about 100 mg of psilocybin. In one embodiment, the psilocybin is administered in a single effective dose of from about 10 mg to about 40 mg. Typically, the single dose may be from about 10 mg to about 35 mg, or from about 15 mg to about 30 mg, or from about 20 mg to about 30 mg. In one embodiment, the single dose is about 25 mg. In one embodiment, the single dose is from about 1 mg to about 10 mg.

The co-crystal may be administered to the patient by any acceptable route of administration including, but not limited to, inhaled, oral, nasal, topical (including transdermal) and parenteral modes of administration. The co-crystal may be administered as, for example: a tablet, capsule, powder, solution or suspension for oral administration; a solution or suspension for injection; or a solution, suspension or powder for inhalation.

The patient to be treated may be suffering from a life-threatening disease. The life-threatening disease may be any chronic disease which has the potential to reduce the normal life expectancy of a patient suffering from the disease. The life-threatening disease may be selected from cancer, heart disease, chronic obstructive pulmonary disease (COPD), diabetes mellitus, Alzheimer's, dementia, motor neurone disease, amyotrophic lateral sclerosis (ALS), Parkinson's disease, epilepsy, multiple sclerosis, and myalgic encephalopathy (ME). In one embodiment, the life-threatening disease is cancer.

Also provided by the invention is a co-crystal as described herein for use in the treatment or prevention of a disease or condition as described herein. In one embodiment, the invention provides a co-crystal as described herein for use in the treatment or prevention of a disease or condition selected from depression, anxiety, death anxiety, demoralization, adjustment disorders, hopelessness, suicidal ideation and desire for hastened death. In one embodiment, the disease or condition is selected from cocaine-related disorders, opioid-related disorders and stimulant-related disorders.

The invention further provides use of a co-crystal as described herein in the manufacture of a medicament for the treatment or prevention of a disease or condition as described herein. In one embodiment, the invention provides use of a co-crystal as described herein in the manufacture of a medicament for the treatment or prevention of a disease or condition selected from depression, anxiety, death anxiety, demoralization, adjustment disorders, hopelessness, suicidal ideation and desire for hastened death. In one embodiment, the disease or condition is selected from cocaine-related disorders, opioid-related disorders and stimulant-related disorders. The treatment or prevention of the disease or condition may be as described herein.

Kits

The kit of the invention comprises a co-crystal or a pharmaceutical composition as described herein, and instructions for use of the co-crystal or pharmaceutical composition in a method of treating or preventing a disease or condition selected from depression, anxiety, death anxiety, demoralization, adjustment disorders, hopelessness, suicidal ideation and desire for hastened death. The kit may comprise instructions for use of the co-crystal or pharmaceutical composition in a method of treating or preventing a disease or condition selected from cocaine-related disorders, opioid-related disorders and stimulant-related disorders.

Salts

The invention also provides a salt of psilocybin and a co-former as described herein. Typically, if psilocybin and the co-former have a $\Delta pK_a$ ($pK_a$ (conjugate acid of base)-$pK_a$ (acid))≥1, there will be substantial proton transfer between psilocybin and the co-former, leading to potential formation of a salt.

For instance, the invention provides a salt of psilocybin and benzylamine. The salt of psilocybin and benzylamine may be in the crystalline form designated as benzylamine Pattern 1 or Pattern 2. The invention also provides a salt of psilocybin and diethylaminoethanol. The salt of psilocybin and diethylaminoethanol may be in the crystalline form designated as diethylaminoethanol Pattern 1. The invention also provides a salt of psilocybin and 4-(2-hydroxyethyl)-morpholine. The salt of psilocybin and 4-(2-hydroxyethyl)-morpholine may be in the crystalline form designated as 4-(2-hydroxyethyl)-morpholine Pattern 1. The invention also provides a salt of psilocybin and 1-(2-hydroxyethyl) pyrrolidine. The salt of psilocybin and 1-(2-hydroxyethyl) pyrrolidine may be in the crystalline form designated as 1-(2-hydroxyethyl) pyrrolidine Pattern 1. The invention also provides a salt of psilocybin and deanol. The salt of psilocybin and deanol may be in the crystalline form designated as deanol Pattern 1, Pattern 2 or Pattern 3. The invention also provides the salt of psilocybin and piperazine. The salt of psilocybin and piperazine may be in the crystalline form designated as piperazine Pattern 1 or Pattern 2. The invention also provides a salt of psilocybin and pyridoxine. The salt of psilocybin and pyridoxine may be in the crystalline form designated as pyridoxine Pattern 1. The invention also provides a salt of psilocybin and tert-butylamine. The salt of psilocybin and tert-butylamine may be in the crystalline form designated as tert-butylamine Pattern 1 or Pattern 2. The invention also provides a salt of psilocybin and urea. The salt of psilocybin and urea may be in the crystalline form designated as urea Pattern 1. The invention also provides a salt of psilocybin and propyl gallate. The salt of psilocybin and propyl gallate may be in the crystalline form designated as propyl gallate Pattern 1.

The salt of psilocybin and piperazine may be in the crystalline form designated as piperazine Pattern 1, wherein Pattern 1 has an x-ray powder diffraction (XRPD) pattern comprising peaks at 13.1°, 15.4° and 24.4°±0.2° 2θ. The XRPD pattern of Pattern 1 of the salt of psilocin and piperazine typically further comprises one or more peaks selected from 9.2°, 11.3° and 15.0°±0.2° 2θ. Pattern 1 of the salt of psilocybin and piperazine may further comprise peaks at 9.2°, 11.3° and 15.0°±0.2° 2θ. The XRPD pattern of Pattern 1 of the salt of psilocin and piperazine may comprise five or more peaks selected from 9.2°, 11.3°, 13.1°, 15.0°, 15.4°, 19.3°, 22.7°, 23.8° and 24.4°±0.2° 2θ. The XRPD pattern may comprise seven or more of these peaks. The XRPD pattern may comprise all of these peaks.

The salt of psilocybin and piperazine may be in the crystalline form designated as piperazine Pattern 2, wherein Pattern 2 has an x-ray powder diffraction (XRPD) pattern comprising peaks at 13.1°, 17.3° and 24.6°±0.2° 2θ. The XRPD pattern of Pattern 2 of the salt of psilocin and piperazine typically further comprises one or more peaks selected from 12.1°, 15.1° and 15.5°±0.2° 2θ. Pattern 1 of the salt of psilocybin and piperazine may further comprise peaks at 12.1°, 15.1° and 15.5°±0.2° 2θ. The XRPD pattern of Pattern 1 of the salt of psilocin and piperazine may comprise five or more peaks selected from 9.3°, 12.1°, 13.1°, 15.1°, 15.5°, 17.3°, 18.7°, 21.4° and 24.6°±0.2° 2θ. The XRPD pattern may comprise seven or more of these peaks. The XRPD pattern may comprise all of these peaks.

The invention is described in more detail by the following Examples. Although preferred embodiments have been depicted and described in detail herein, it will be apparent to those skilled in the relevant art that various modifications, additions, substitutions and the like can be made without departing from the spirit of the invention and these are therefore considered to be within the scope of the invention as defined in the claims which follow.

The texts of references cited in this disclosure are herein incorporated by reference in their entireties.

EXAMPLES

Example 1: Screening

Screening Methods

An in silico co-crystal screen was performed using two independent approaches, the machine learning (ML) model and the COSMO-RS method.

The first method was based on COSMO-RS predictions of the API-co-former miscibility, as measured by the excess enthalpy ($H_{ex}$) property. The predictions are performed in an amorphous-type phase. The screening was performed with COSMOtherm software, where multiple conformers are generated for each co-former by RDKit with an RMSD cut-off value of 0.5 Å. The generated conformations are further optimized in a perfect conductor media by the Turbomole package at the BP/TZVP/COSMO-RS level of theory.

The mixing enthalpy property ($H_{ex}$) was used to characterize the co-crystallization tendency (the overall stability changes of the system). Assuming that the mixing entropy ($\Delta S_{mix}$) and the change of melting free energy ($\Delta\Delta G_{fus}$) can be ignored, the enthalpy change ($\Delta H_{ex}$) of supercooled liquid mixing can be used to characterize the thermodynamic tendency of cocrystallization:

$$\Delta G_{cocrystal} = \Delta H_{ex} - \Delta S_{mix}T + \Delta\Delta G_{fus} \approx \Delta H_{ex}$$

The second method was a screening approach based on machine learning (ML) models. In this approach, the co-former screening models were built and validated using the Random Forest algorithm. The observations for co-formers were extracted from the CSD database, published experimental studies, and co-crystallization experiments. 2D descriptors were generated by the RDKit and CDK packages. The ML models can predict the probability of co-crystal formation between psilocybin and the co-former.

The $pK_a$ values of psilocybin are shown below for basic (amine) and acidic (phosphate) centres. Psilocybin has a strong propensity to be a zwitterion. The $pK_a$ of psilocybin was taken as $pK_a$ (acidic)=6.5 since the other strongly ionized spots tend to form the zwitterion. The value used to calculate $\Delta pK_a$ for acidic/basic psilocybin is marked by the circle. The $pK_a$ values of psilocybin were calculated by MarvinSketch.

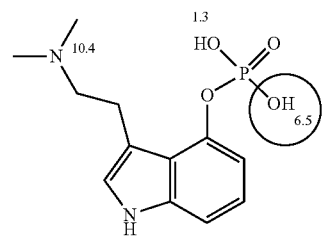 [SMILES: CN(C)CCc1c[nH]c2cccc(OP(=O)(O)O)c12]

Table 1 lists the co-formers that were assessed using the above in silico methods.

TABLE 1

Melting point and p$K_a$ properties of the assessed co-formers

| Coformer name | CAS | Melting point (° C.) | p$K_a$ (acidic) | p$K_a$ (basic) |
|---|---|---|---|---|
| theophylline | 58-55-9 | 273 | 8.81 | — |
| nicotinamide | 98-92-0 | 130 | — | 3.35 |
| citric acid | 77-92-9 | 153 | 2.79 | — |
| fumaric acid | 110-17-8 | 298-300 | 3.03 | — |
| propyl gallate (3,4,5-trihydroxybenzoate) | 121-79-9 | 130 | 7.94 | — |
| succinic acid | 110-15-6 | 188 | 4.21 | — |
| gluconic acid | 526-95-4 | 131.0 | 3.6 | — |
| L-tartaric acid | 87-69-4 | 170-172 | 2.89 | — |
| L-ascorbic acid | 50-81-7 | 190-194 | 4.70 | — |
| L-ascorbic acid, 6-hexadecanoate | 137-66-6 | 115-118 | — | — |
| isonicotinamide | 1453-82-3 | 156 | — | 3.61 |
| 2,6-di-tert-butyl-4-methylphenol | 128-37-0 | 71.0 | — | — |
| urea | 57-13-6 | 132.7 | — | 0.10 |
| 2-tert-butyl-4-methoxyphenol | 121-00-6 | 48-63 | — | — |
| L-lactic acid | 79-33-4 | 40.86 | 3.83 | — |
| saccharin | 81-07-2 | 228 | — | — |
| ethylmaltol | 4940-11-8 | 90-91 | — | — |
| tromethamine | 77-86-1 | 171-172 | — | 8.95 |
| sodium bisulfite | 7631-90-5 | 150 | — | — |
| acesulfame potassium | 55589-62-3 | 229-232 | — | — |
| L-pyroglutamic acid | 98-79-3 | 184.7 | 3.48 | — |
| disodium EDTA | 139-33-3 | 248 | — | — |
| sodium formaldehyde sulfoxylate | 149-44-0 | 63-64 | — | — |
| meso-erythritol | 149-32-6 | 121.5 | 13.90 | — |
| D-mannitol | 69-65-8 | 168 | 13.50 | — |
| D-sorbitol | 50-70-4 | 98-100 | 13.60 | — |
| DL-cystiene | 3374-22-9 | 260 | 1.71 | 8.33 |
| inosine | 58-63-9 | 218 | — | — |
| nicotinic acid | 59-67-6 | 236-6 | 4.75 | — |
| D-xylitol | 87-99-0 | 98-75 | — | — |
| L-glutamic acid | 56-86-0 | 213 | 2.19 | 9.67 |

Results

Co-former screening results are presented in Table 2.

Based on the $H_{ex}$ property and the ML probability of specific combinations of psilocybin and a co-former, all evaluated co-formers were classified and separated into categories based the predicted propensity of each co-former to form a co-crystal with psilocybin.

Class A co-formers: Machine Learning probability greater than 0.5.

Class B co-formers: $H_{ex}$ less than −12.0 kJ/mol and Machine Learning probability less than 0.5.

Class C co-formers: Machine Learning probability less than 0.5 and $H_{ex}$ greater than −12.0 kJ/mol but less than 0 kJ/mol.

Class D co-formers: Those that failed to meet the above criteria, but are retained as possible co-formers.

Co-formers that have delta p$K_a$ greater than 3.0 were left out due to relatively higher salt (rather than co-crystal) formation propensity. The Δp$K_a$ values were calculated by the following equation:

$$\Delta pK_a = pK_a(\text{conjugate acid of base}) - pK_a(\text{acid})$$

Class A includes citric acid, fumaric acid, succinic acid, gluconic acid, L-tartaric acid, and L-ascorbic acid. Class B includes L-lactic acid and saccharin. Class C includes disodium EDTA and nicotinic acid.

TABLE 2

Co-former screening results

| Coformer name | Δp$K_a$ (API acid) | Δp$K_a$ (API base) | $H_{ex}$ (KJ/mol) | ML | Class |
|---|---|---|---|---|---|
| citric acid | — | — | −24.07 | 0.34 | B |
| fumaric acid | — | — | −22.37 | 0.34 | B |
| succinic acid | — | — | −15.78 | 0.31 | B |
| gluconic acid | — | — | −12.83 | 0.26 | B |
| L-tartaric acid | — | — | −25.85 | 0.26 | B |
| L-ascorbic acid | — | — | −15.24 | 0.26 | B |
| L-lactic acid | — | — | −8.28 | 0.39 | C |
| saccharin | — | — | −3.04 | 0.39 | C |
| disodium EDTA | — | — | −6.80 | 0.31 | D |
| nicotinic acid | — | — | −4.66 | 0.25 | D |
| theophylline | — | — | −0.10 | 0.52 | B |
| nicotinamide | −3.15 | — | 0.25 | 0.51 | B |
| isonicotinamide | −2.89 | — | 0.12 | 0.48 | C |
| tromethamine | 2.45 | — | −1.32 | 0.34 | C |
| propyl gallate (3,4,5-trihydroxybenzoate) | — | — | −18.58 | 0.33 | B |
| L-ascorbic acid 6-hexadecanoate | — | — | −14.80 | 0.24 | B |
| 2,6Di-Tert-Butyl-4-Methylphenol | — | — | −1.21 | 0.43 | C |
| 2-tert-butyl-4-methoxyphenol | — | — | −9.84 | 0.41 | C |
| urea | −6.4 | — | 0.02 | 0.42 | C |
| ethylmaltol | — | — | 0.11 | 0.36 | C |
| sodium bisulfite | — | — | −5.88 | 0.34 | C |
| acesulfame potassium | — | — | 0.15 | 0.32 | C |
| L-pyroglutamic acid | — | — | −3.29 | 0.31 | D |
| sodium formaldehyde sulfoxylate | — | — | −5.85 | 0.31 | D |
| meso-erythritol | — | — | −3.56 | 0.30 | D |
| D-mannitol | — | — | −5.69 | 0.30 | D |
| D-sorbitol | — | — | −4.94 | 0.30 | D |
| DL-cysteine | 1.83 | — | −5.20 | 0.29 | D |
| inosine | — | — | −2.82 | 0.26 | D |
| D-xylitol | — | — | −3.19 | 0.24 | D |
| L-glutamic acid | 3.17 | — | 0.36 | 0.22 | D |

Based on the above considerations, co-formers were recommended for an experimental follow-up.

Example 2: Preparation Methods

Co-crystals are prepared according to the methods below.

(a) Reactive Crystallisation

Feed solutions, at predefined molar equivalents, each containing psilocybin or the co-former in a solvent/solvent system are mixed together and stirred either manually, mechanically or with the use of ultrasound (ultrasonication). Supersaturation is achieved either by evaporation, cooling, anti-solvent addition, spray-drying or freeze drying. The resulting co-crystal is isolated and dried.

(b) Crystallisation

A predefined molar equivalent ratio of psilocybin and co-former is either dissolved directly or via mechanical grinding (for example using a pestle and mortar), at a defined temperature, in a solvent/solvent system to yield a clear solution. Supersaturation is achieved either by evaporation, cooling, anti-solvent addition, spray-drying or freeze drying. The resulting co-crystal is isolated and dried.

(c) Slurry or Suspension Mediated Crystallisation

Predefined molar equivalents of psilocybin and co-former are suspended in a solvent/solvent system such that a solid fraction remains in excess. The suspension is then stirred either manually, by mechanical means or via the use of ultrasound, or with the use of a shear granulation process. The experiment is either performed isothermally or with a temperature gradient or thermal cycling. The resulting co-crystal is isolated and dried.

(d) Solid State Grinding

Predefined molar equivalents of psilocybin and co-former are mixed and ground either manually or mechanically (for example with a ball mill or an extruder). The resultant co-crystal is isolated.

(e) Liquid Assisted Grinding

Predefined molar equivalents of psilocybin and co-former are mixed along with a small volume (typically 1:4 volume: weight ratio of total solid) of a solvent/solvent system and ground either manually, mechanically (for example with the use of a ball mill) or with the use of a resonant acoustic mixer. The resultant co-crystal is isolated and dried.

(f) Solid State Mediated

Predefined molar equivalents of psilocybin and co-former are mixed together and either exposed to high power laser irradiation or an electrochemical source. The resultant co-crystal is isolated.

(g) Melt Mediated Crystallisation

Predefined molar equivalents of psilocybin and co-former are mixed together and simultaneously melted and mixed either directly or mechanically (for example via a hot melt extruder). The resultant molten mixture is then cooled to obtain the resultant co-crystal.

Example 3: Initial Crystallisation Experiments

More than 40 small-scale crystallization experiments were conducted using suitable crystallization methods such as slurry equilibration, precipitation, vapor diffusion, and solvent drop grinding. 23 formers were tested, namely L-arginine, ascorbic acid, benzylamine, citric acid, diethylaminoethanol, L-glutamine, glutamic acid, 4-(2-hydroxyethyl)-morpholine, 1-(2-hydroxyethyl) pyrrolidine, L-histidine, L-tartaric acid, deanol, nicotinamide, piperazine, L-proline, pyridoxine, saccharin, succinic acid, tert-butylamine, theophiline, tromethamine, urea, and L-valine. The experiments were conducted on a 40 mg-scale.

Solvent Drop Grinding

Solvent drop grinding experiments were carried out with the co-formers and solvent systems described in Table 3. All the experiments were conducted at room temperature using an agate mortar and pestle, expect for the experiment with citric acid which was conducted in a milling jar with two milling balls. Most of the experiments were conducted using a solvent system; 50 µL of solvent was typically added to the powder mixture, and milling was conducted for 1-2 minutes. The obtained powder was then gathered in the middle of the mortar with a spatula, solvent was again added, and the milling process was repeated. This milling was conducted a total of three times for each experiment. No solvent was used for the experiment with tert-butylamine, which is a liquid base. For citric acid, a ball milling experiment was performed with one equivalent of citric acid and an acetone/water 1:1 mixture. This mixture was placed in a milling jar with two balls and milling was conducted for 3×5 minutes with 5 minutes of break between each step. The sample was dried overnight, under vacuum (<5 mbar, r.t.).

TABLE 3

| Solvent drop grinding experiments | |
|---|---|
| Co-former | Solvent |
| ascorbic acid | Acetone |
| citric acid | Acetone/water 1:1 |
| glutamic acid | — |

TABLE 3-continued

| Solvent drop grinding experiments | |
|---|---|
| Co-former | Solvent |
| nicotinamide | Acetone/water 1:1 |
| piperazine | Ethyl acetate |
| L-proline | Ethanol |
| Pyridoxine | THF |
| succinic acid | THF |
| tert-butylamine | — |
| theophiline | MeOH/water 1:1 |

Vapor Diffusion Experiments

Vapor diffusion experiments were conducted by dissolving psilocybin and 1.1 equivalents of the former in DMSO. The obtained solution was placed in an open glass vial that was then placed in a larger receptacle containing toluene. The whole system was closed and allowed to stand under the conditions outlined in Table 4. The solids were isolated by filtration.

TABLE 4

| Vapor diffusion experiments | |
|---|---|
| Co-former | Conditions |
| L-tartaric acid | r.t. one week, then 5° C. for 3 days |
| Saccharin | r.t. one week |
| Nicotinamide | r.t. one week |

Slurry Experiments

For solid co-formers, approx. 40 mg of psilocybin was suspended in 1 mL of the concentrated coformer solution such that the co-former was in excess, and the obtained suspension was stirred over several days. The suspension was then filtered. A corresponding set of experiments was also carried out using 1.1 equivalents of co-former.

For liquid co-formers, psilocybin was suspended in the desired liquid co-former, and the obtained suspension was equilibrated over several days. The solid was then isolated by filtration.

The conducted experiments are summarised in Table 5.

TABLE 5

| Slurry experiments | | |
|---|---|---|
| Co-former (amount) | Solvent | Conditions |
| Ascorbic acid (excess) | DMF | 25° C., several weeks |
| Citric acid (excess) | THF | 25° C., 5 days |
| L-tartaric acid (excess) | THF | 25-35° C., 6 days |
| Nicotinamide (excess) | ACN | 25-35° C., 6 days |
| Piperazine (excess) | MEK | 25° C., 6 days |
| Pyridoxine (excess) | NMP | 25° C., 6 days |
| Saccharin (excess) | Acetone | 25-35° C., 6 days |
| Succinic acid (excess) | Dioxane | r.t., 1 week |
| Urea (excess) | DMF | 25° C., 6 days |
| Benzylamine | — | r.t. 5 days |
| Diethylaminoethanol | — | r.t., 5 days |
| 4-(2hydroxyethyl) morpholine | — | 25° C., 1 week |
| 1-(2-hydroxyethyl) pyrrolidine | — | 25-35° C., 3 days |
| Deanol | — | 25° C., 1 week |
| Tert-butylamine | — | r.t., 5 days |
| Glutamic acid (1:1) | Acetic acid | 25° C., 6 days |
| L-glutamine (1:1) | Water | r.t., 5 days |
| L-histidine (1:1) | Water | r.t., 5 days |
| Piperazine | Ethyl acetate | r.t., 5 days |
| Pyridoxine | THF | r.t., 5 days |

TABLE 5-continued

Slurry experiments

| Co-former (amount) | Solvent | Conditions |
|---|---|---|
| Succinic acid | Mixture* | 25-35° C., 1 week |
| Tromethamine | NMP | r.t., 1 week |
| Urea | Acetonitrile | r.t., 1 week |
| L-valine | Water | r.t., 5 days |

*equimolar amounts of anisole, 2-butanol, butylacetate, butyronitrile, DMF, dioxane, MIBK, 2-propanol, toluene, water Based on the outcome of these small scale crystallisation experiments, co-formers were taken forward for further investigation and analysis. In particular, it was found that the co-formers piperazine, benzylamine, diethylaminoethanol, 4-(2-hydroxyethyl)-morpholine, 1-(2-hydroxyethyl) pyrrolidine, deanol, pyridoxine, tert-butylamine, urea and propyl gallate were able to form crystalline co-crystals with psilocybin.

Example 4: Analytical Methods

In the following examples, the following analytical methods were used.

DSC

Differential scanning calorimetry was carried out with a TA Instruments Q2000 or a DSC 2500 instrument. Closed pans (hermetically sealed or with a pinhole in the lid) were used for the measurement. The aluminium sample pans were filled with sample under ambient conditions. The measurements were conducted with a heating rate of 10° C./min. The melting point is understood as the peak maximum.

DVS

Dynamic vapor sorption was carried out with a proUmid SPS23-100n instrument. The following program was applied to all DVS measurements: 50% r.h.-0% r.h.-95% r.h.-0% r.h.-95% r.h.-50% r.h., scan rate of 5% r.h. per hour, T=25° C.

PXRD (XRPD)

Stoe Stadi P equipped with a Mythen1 K Detector; Cu-K$\alpha$1 radiation; standard measurement conditions: transmission; 40 kV and 40 mA tube power; curved Ge monochromator; 0.02° 2θ step size, 48 s step time, 1.5-50.5° 2θ scanning range; detector mode: step scan; 1° 2θ detector step. The samples (10-20 mg of powder) were measured between two acetate foils or Kapton foils. No special treatment was used in preparing the samples other than the application of slight pressure to distribute the powder over the irradiated surface area. An ambient air atmosphere was used for all measurements, and each sample was rotated during the measurement.

TG-FTIR

Thermogravimetric measurements were carried out with a Netzsch Thermo-Microbalance TG 209 F1 Nevio coupled to a Bruker FT-IR Spectrometer Tensor II. Aluminium sample pans with a pinhole, $N_2$ atmosphere, heating rate 10° C./min.

Solubility in FaSSiF

A powder of the co-crystal was suspended in 0.5 mL of FaSSiF, and the mixture was equilibrated with 700 rpm at 37° C. After four hours, the obtained suspensions or solutions were then filtered using centrifugal unit filters (0.5 mL, PVDF, 0.1 µm, 3000 rcf, 1 minute). The concentrations in the recovered clear solutions were determined by HPLC.

The HPLC device used was from Agilent, Series 1260 with Chromeleon Version 7.2.10 software, according to the following parameters.

| Parameter | Description |
|---|---|
| column | Agilent InfinityLab Poroshell 120 EC-C18, 100 × 4.6 mm, 2.7 µm |
| sample dilution solvent | 1000 mL water + 1 mL HCl |
| mobile phase A | water + 0. 1% TFA |
| mobile phase B | water/ACN 1:1 + 0.1% TFA |
| gradient | 0.0 min: 5% B |
|  | 5.0 min: 5% B |
|  | 18.0 min: 80% B |
|  | 23.0 min. 80% B |
|  | 23.1 min: 5% B |
|  | 30.0 min: 5% B |
| flow | 1 mL min$^{-1}$ |
| injection volume | 5 µL |
| detection | 220 nm |
| column temperature | 30° C. |
| sample temperature | 25° C. |
| run time | 30 min |
| max. pressure | 210 bar |

Example 5: Preparation of Co-Crystals (i) Benzylamine

Approximately 40 mg psilocybin was suspended in excess benzylamine (liquid base). After five days of stirring at r.t., the suspension was filtered, and a mixture of powder and gel was obtained. PXRD investigation on this mixture revealed a new PXRD pattern, herein designated as benzylamine Pattern 1, the XRPD characteristics of which are shown in Table 6 below and in FIG. 1.

The remaining wet sample was then washed with TBME, and the obtained solid was vacuum dried (<10 mbar, r.t.). A new PXRD pattern was obtained after drying, herein designated as benzylamine Pattern 2, the XRPD characteristics of which are shown in Table 7 below and in FIG. 2.

TABLE 6

XRPD peak list for benzylamine co-crystal Pattern 1

| Angle °2-Theta | d-spacing in Angstrom | Rel. Intensity % |
|---|---|---|
| 5.71 | 15.47 | 100 |
| 8.59 | 10.29 | 11 |
| 8.84 | 10.00 | 3 |
| 9.52 | 9.29 | 5 |
| 9.84 | 8.98 | 7 |
| 11.38 | 7.77 | 3 |
| 11.82 | 7.48 | 4 |
| 12.08 | 7.32 | 4 |
| 12.74 | 6.94 | 4 |
| 13.67 | 6.47 | 4 |
| 14.34 | 6.17 | 8 |
| 14.92 | 5.93 | 9 |
| 16.00 | 5.53 | 20 |
| 16.68 | 5.31 | 6 |
| 17.21 | 5.15 | 15 |
| 17.73 | 5.00 | 9 |
| 18.19 | 4.87 | 10 |
| 18.58 | 4.77 | 14 |
| 18.85 | 4.70 | 16 |
| 19.41 | 4.57 | 7 |
| 19.70 | 4.50 | 7 |
| 20.15 | 4.40 | 7 |
| 20.32 | 4.37 | 6 |
| 20.76 | 4.28 | 17 |
| 21.12 | 4.20 | 7 |
| 21.44 | 4.14 | 7 |
| 22.32 | 3.98 | 6 |
| 22.66 | 3.92 | 14 |
| 22.94 | 3.87 | 7 |
| 23.78 | 3.74 | 5 |

TABLE 6-continued

XRPD peak list for benzylamine co-crystal Pattern 1

| Angle °2-Theta | d-spacing in Angstrom | Rel. Intensity % |
|---|---|---|
| 24.11 | 3.69 | 6 |
| 24.79 | 3.59 | 7 |
| 25.26 | 3.52 | 6 |
| 25.50 | 3.49 | 6 |
| 25.94 | 3.43 | 5 |
| 26.75 | 3.33 | 5 |
| 26.98 | 3.30 | 4 |
| 27.62 | 3.23 | 4 |
| 28.05 | 3.18 | 4 |
| 28.62 | 3.12 | 3 |
| 29.17 | 3.06 | 3 |
| 30.10 | 2.97 | 3 |
| 30.57 | 2.92 | 5 |
| 30.94 | 2.89 | 4 |
| 31.74 | 2.82 | 4 |
| 32.32 | 2.77 | 3 |
| 32.75 | 2.73 | 2 |
| 33.94 | 2.64 | 2 |
| 35.37 | 2.54 | 2 |
| 37.99 | 2.37 | 2 |
| 38.60 | 2.33 | 2 |
| 39.11 | 2.30 | 2 |
| 40.18 | 2.24 | 2 |

TABLE 7

XRPD peak list for benzylamine co-crystal Pattern 2

| Angle °2-Theta | d-spacing in Angstrom | Rel. Intensity % |
|---|---|---|
| 7.06 | 12.51 | 100 |
| 8.82 | 10.01 | 29 |
| 10.41 | 8.49 | 53 |
| 11.07 | 7.99 | 34 |
| 11.92 | 7.42 | 25 |
| 13.77 | 6.43 | 30 |
| 14.40 | 6.15 | 28 |
| 16.49 | 5.37 | 37 |
| 17.29 | 5.12 | 25 |
| 17.67 | 5.02 | 24 |
| 18.20 | 4.87 | 34 |
| 19.08 | 4.65 | 38 |
| 19.44 | 4.56 | 17 |
| 19.89 | 4.46 | 41 |
| 20.22 | 4.39 | 65 |
| 20.92 | 4.24 | 21 |
| 21.35 | 4.16 | 21 |
| 21.66 | 4.10 | 26 |
| 22.24 | 3.99 | 26 |
| 22.82 | 3.89 | 35 |
| 23.56 | 3.77 | 14 |
| 24.34 | 3.65 | 19 |
| 24.79 | 3.59 | 16 |
| 25.49 | 3.49 | 50 |
| 25.80 | 3.45 | 25 |
| 26.55 | 3.36 | 19 |
| 26.84 | 3.32 | 12 |
| 27.25 | 3.27 | 19 |
| 27.79 | 3.21 | 14 |
| 28.36 | 3.14 | 10 |
| 28.96 | 3.08 | 13 |
| 29.72 | 3.00 | 12 |
| 30.32 | 2.95 | 11 |
| 31.04 | 2.88 | 10 |
| 34.38 | 2.61 | 9 |
| 35.11 | 2.55 | 11 |
| 35.78 | 2.51 | 8 |

Further analysis of benzylamine Pattern 2 gave the following results.

Based on $^1$H-NMR analysis, 1.1 eq of benzylamine were estimated. Shifts were observed for the methyl signal (2.71 ppm→2.54 ppm) and the aromatic signals, compared to the free drug reference.

(ii) Diethylaminoethanol

Approximately 40 mg psilocybin was suspended in excess diethylaminoethanol (liquid base). After five days of stirring at r.t., the slightly yellowish suspension was filtered, and a mixture of powder and gel was obtained. PXRD investigation on the mixture revealed a PXRD pattern, herein designated as diethylaminoethanol Pattern 1, the XRPD characteristics of which are shown in Table 8 below and in FIG. 3.

TABLE 8

XRPD peak list for diethylaminoethanol co-crystal Pattern 1

| Angle °2-Theta | d-spacing in Angstrom | Rel. Intensity % |
|---|---|---|
| 5.57 | 15.86 | 100 |
| 14.52 | 6.10 | 67 |

Further analysis of diethylaminoethanol Pattern 1 gave the following results.

Based on $^1$H-NMR analysis, 1.6 eq. of diethylaminoethanol were estimated. Slight shifts were observed for the methyl signal (2.71 ppm→2.68 ppm) and the aromatic signals compared to the free drug reference.

(iii) 4-(2-hydroxyethyl)-morpholine

Approximately 40 mg psilocybin was suspended in excess 4-(2-hydroxyethyl)-morpholine and the obtained suspension was equilibrated at 25° C. After seven days of stirring, the solid was isolated by filter centrifugation, and the wet sample was then dried under vacuum (<5 mbar, r.t.) for one day. The obtained solid was investigated by PXRD, and a new crystalline PXRD pattern was obtained, herein designated as 4-(2-hydroxyethyl)-morpholine Pattern 1, the XRPD characteristics of which are shown in Table 9 below and in FIG. 4.

TABLE 9

XRPD peak list for 4-(2-hydroxyethyl)-morpholine co-crystal Pattern 1

| Angle °2-Theta | d-spacing in Angstrom | Rel. Intensity % |
|---|---|---|
| 5.83 | 15.14 | 50 |
| 11.82 | 7.48 | 45 |
| 12.34 | 7.17 | 90 |
| 13.95 | 6.34 | 24 |
| 14.83 | 5.97 | 25 |
| 15.31 | 5.78 | 33 |
| 15.85 | 5.59 | 31 |
| 17.56 | 5.05 | 33 |
| 17.85 | 4.97 | 25 |
| 19.23 | 4.61 | 19 |
| 19.70 | 4.50 | 16 |
| 20.28 | 4.37 | 23 |
| 20.52 | 4.32 | 25 |
| 21.04 | 4.22 | 25 |
| 21.73 | 4.09 | 29 |
| 22.32 | 3.98 | 56 |
| 22.57 | 3.94 | 22 |
| 23.74 | 3.74 | 100 |
| 24.41 | 3.64 | 42 |
| 24.64 | 3.61 | 19 |
| 24.85 | 3.58 | 16 |
| 25.33 | 3.51 | 37 |
| 25.78 | 3.45 | 21 |

TABLE 9-continued

XRPD peak list for 4-(2-hydroxyethyl)-morpholine co-crystal Pattern 1

| Angle °2-Theta | d-spacing in Angstrom | Rel. Intensity % |
|---|---|---|
| 26.33 | 3.38 | 10 |
| 27.35 | 3.26 | 19 |
| 28.31 | 3.15 | 12 |
| 28.80 | 3.10 | 14 |
| 29.23 | 3.05 | 8 |
| 29.70 | 3.01 | 10 |
| 30.00 | 2.98 | 7 |
| 30.73 | 2.91 | 19 |
| 31.25 | 2.86 | 9 |
| 31.80 | 2.81 | 7 |
| 32.08 | 2.79 | 7 |
| 32.57 | 2.75 | 8 |
| 32.81 | 2.73 | 8 |
| 33.56 | 2.67 | 7 |
| 33.85 | 2.65 | 6 |
| 34.27 | 2.61 | 6 |
| 34.86 | 2.57 | 7 |
| 35.50 | 2.53 | 7 |
| 35.91 | 2.50 | 8 |
| 36.12 | 2.48 | 10 |
| 37.09 | 2.42 | 7 |
| 37.64 | 2.39 | 6 |
| 37.84 | 2.38 | 7 |
| 38.87 | 2.32 | 8 |
| 39.19 | 2.30 | 7 |
| 39.90 | 2.26 | 7 |
| 40.51 | 2.23 | 5 |

Further analysis of 4-(2-hydroxyethyl)-morpholine Pattern 1 gave the following results.

The obtained $^1$H-NMR spectrum was consistent with the structure of psilocybin structure, no shifts were observed compared to the signal of the free drug starting material. 1.0 equivalents of 4-(2-hydroxyethyl)-morpholine were found.

(iv) 1-(2-hydroxyethyl)-pyrrolidine

Approximately 40 mg psilocybin was suspended in excess 1-(2-hydroxyethyl)-pyrrolidine. After five days of stirring at r.t. heptane was then added as an antisolvent, and a gel/paste was obtained. This mixture was submitted to temperature cycling 25° C.-35° C., and a suspension was obtained after three days of stirring. The solid was isolated by filter centrifugation and was dried under vacuum (<5 mbar, r.t.) for one day. A new crystalline PXRD pattern was obtained, herein 1-(2-hydroxyethyl)-pyrrolidine Pattern 1, the XRPD characteristics of which are shown in Table 10 below and in FIG. 5.

TABLE 10

XRPD peak list for 1-(2-hydroxyethyl)-pyrrolidine co-crystal Pattern 1

| Angle °2-Theta | d-spacing in Angstrom | Rel. Intensity % |
|---|---|---|
| 3.21 | 27.53 | 24 |
| 5.62 | 15.72 | 20 |
| 6.47 | 13.66 | 24 |
| 10.95 | 8.07 | 100 |
| 11.60 | 7.62 | 26 |
| 12.06 | 7.33 | 39 |
| 13.13 | 6.74 | 22 |
| 13.52 | 6.55 | 32 |
| 15.00 | 5.90 | 23 |
| 15.81 | 5.60 | 21 |
| 18.23 | 4.86 | 20 |
| 18.69 | 4.75 | 39 |
| 18.98 | 4.67 | 24 |
| 19.74 | 4.49 | 29 |
| 20.14 | 4.40 | 38 |
| 21.11 | 4.20 | 29 |
| 21.94 | 4.05 | 54 |
| 22.68 | 3.92 | 26 |
| 23.43 | 3.79 | 59 |
| 23.72 | 3.75 | 70 |
| 24.50 | 3.63 | 32 |
| 25.33 | 3.51 | 17 |
| 25.67 | 3.47 | 20 |
| 28.70 | 3.11 | 15 |
| 29.02 | 3.07 | 11 |
| 30.62 | 2.92 | 16 |
| 31.18 | 2.87 | 11 |
| 32.40 | 2.76 | 11 |
| 32.96 | 2.72 | 9 |
| 34.28 | 2.61 | 11 |
| 35.42 | 2.53 | 11 |
| 38.05 | 2.36 | 7 |
| 39.60 | 2.27 | 8 |

Further analysis of 1-(2-hydroxyethyl)-pyrrolidine Pattern 1 gave the following results.

The obtained $^1$H-NMR spectrum was consistent with the psilocybin structure.

(v) Deanol

Approximately 40 mg psilocybin was suspended in excess dimethylaminoethanol (deanol). After one week of stirring at 25° C., the suspension was filtered, and the wet cake was submitted for PXRD. A new crystalline PXRD pattern was obtained, herein designated as deanol Pattern 1, the XRPD characteristics of which are shown in Table 11 below and in FIG. 6.

The remaining wet sample was washed with heptane and dried under vacuum (<10 mbar, r.t.) for one day. A new PXRD pattern was obtained for the dried sample, herein designated as deanol Pattern 2, the XRPD characteristics of which are shown in Table 12 below and in FIG. 7.

In a separate experiment, psilocybin was suspended in excess deanol (N,N-dimethylethanolamine). The obtained suspension was stirred at r.t. After three days of stirring, the suspension was filtered and the obtained cake was washed twice with heptane and dried under vacuum (<10 mbar) at r.t. After overnight drying, heptane was added and the suspension was stirred for 3 days at r.t., then filtered and dried under vacuum. The sample was then suspended in ethyl acetate at r.t. After approx. 40 hours of stirring at r.t., the suspension was filtered using a centrifugal unit filter and the wet material was submitted for PXRD. The resulting pattern is designated as deanol Pattern 3, the XRPD characteristics of which are shown in Table 13 below and in FIG. 8.

TABLE 11

XRPD peak list for deanol co-crystal Pattern 1

| Angle °2-Theta | d-spacing in Angstrom | Rel. Intensity % |
|---|---|---|
| 5.17 | 17.07 | 12 |
| 5.59 | 15.81 | 13 |

TABLE 11-continued

XRPD peak list for deanol co-crystal Pattern 1

| Angle °2-Theta | d-spacing in Angstrom | Rel. Intensity % |
|---|---|---|
| 10.77 | 8.21 | 40 |
| 11.29 | 7.83 | 18 |
| 11.64 | 7.60 | 51 |
| 12.09 | 7.31 | 22 |
| 13.34 | 6.63 | 16 |
| 13.98 | 6.33 | 10 |
| 17.50 | 5.06 | 12 |
| 19.32 | 4.59 | 18 |
| 19.90 | 4.46 | 12 |
| 20.94 | 4.24 | 54 |
| 21.44 | 4.14 | 100 |
| 21.80 | 4.07 | 10 |
| 22.52 | 3.94 | 20 |
| 22.93 | 3.87 | 14 |
| 23.32 | 3.81 | 85 |
| 24.34 | 3.65 | 98 |
| 24.68 | 3.60 | 12 |
| 25.35 | 3.51 | 10 |
| 26.71 | 3.34 | 8 |
| 28.37 | 3.14 | 37 |
| 29.10 | 3.07 | 27 |
| 30.14 | 2.96 | 17 |
| 30.42 | 2.94 | 9 |
| 30.86 | 2.90 | 10 |
| 31.16 | 2.87 | 10 |
| 31.42 | 2.84 | 10 |
| 31.79 | 2.81 | 8 |
| 32.32 | 2.77 | 6 |
| 32.75 | 2.73 | 11 |
| 33.32 | 2.69 | 6 |
| 33.95 | 2.64 | 6 |
| 34.56 | 2.59 | 18 |
| 35.14 | 2.55 | 20 |
| 35.51 | 2.53 | 6 |
| 35.98 | 2.49 | 4 |
| 36.55 | 2.46 | 6 |
| 37.71 | 2.38 | 6 |
| 38.17 | 2.36 | 5 |
| 39.04 | 2.31 | 9 |
| 39.37 | 2.29 | 5 |
| 39.77 | 2.26 | 4 |
| 40.72 | 2.21 | 5 |

TABLE 12

XRPD peak list for deanol co-crystal Pattern 2

| Angle °2-Theta | d-spacing in Angstrom | Rel. Intensity % |
|---|---|---|
| 6.95 | 12.71 | 18 |
| 10.74 | 8.23 | 31 |
| 11.30 | 7.83 | 22 |
| 12.44 | 7.11 | 100 |
| 13.96 | 6.34 | 38 |
| 15.04 | 5.89 | 23 |
| 17.47 | 5.07 | 35 |
| 18.12 | 4.89 | 18 |
| 18.62 | 4.76 | 18 |
| 18.96 | 4.68 | 19 |
| 19.61 | 4.52 | 33 |
| 19.90 | 4.46 | 57 |
| 20.36 | 4.36 | 18 |
| 20.64 | 4.30 | 54 |
| 21.03 | 4.22 | 30 |
| 21.33 | 4.16 | 20 |
| 21.83 | 4.07 | 27 |
| 22.20 | 4.00 | 10 |
| 22.69 | 3.92 | 17 |
| 23.19 | 3.83 | 47 |
| 23.50 | 3.78 | 24 |
| 24.08 | 3.69 | 22 |
| 25.02 | 3.56 | 27 |
| 25.82 | 3.45 | 12 |

TABLE 12-continued

XRPD peak list for deanol co-crystal Pattern 2

| Angle °2-Theta | d-spacing in Angstrom | Rel. Intensity % |
|---|---|---|
| 26.86 | 3.32 | 7 |
| 27.18 | 3.28 | 23 |
| 27.49 | 3.24 | 10 |
| 27.90 | 3.20 | 9 |
| 28.11 | 3.17 | 11 |
| 28.40 | 3.14 | 29 |
| 28.72 | 3.11 | 10 |
| 29.29 | 3.05 | 10 |
| 29.62 | 3.01 | 17 |
| 30.21 | 2.96 | 8 |
| 30.60 | 2.92 | 6 |
| 31.37 | 2.85 | 7 |
| 31.91 | 2.80 | 6 |
| 32.56 | 2.75 | 17 |
| 32.97 | 2.71 | 6 |
| 33.53 | 2.67 | 10 |
| 34.32 | 2.61 | 8 |
| 35.42 | 2.53 | 6 |
| 35.91 | 2.50 | 8 |
| 36.18 | 2.48 | 6 |
| 37.26 | 2.41 | 5 |
| 38.17 | 2.36 | 5 |
| 38.78 | 2.32 | 4 |
| 39.22 | 2.30 | 4 |
| 39.69 | 2.27 | 4 |
| 40.64 | 2.22 | 4 |

TABLE 13

XRPD peak list for deanol co-crystal Pattern 3

| Angle °2-Theta | d-spacing in Angstrom | Rel. Intensity % |
|---|---|---|
| 7.30 | 12.10 | 43 |
| 10.33 | 8.56 | 100 |
| 12.12 | 7.30 | 95 |
| 13.61 | 6.50 | 29 |
| 14.10 | 6.28 | 82 |
| 14.64 | 6.05 | 45 |
| 15.48 | 5.72 | 29 |
| 17.55 | 5.05 | 51 |
| 19.19 | 4.62 | 31 |
| 19.77 | 4.49 | 87 |
| 20.75 | 4.28 | 22 |
| 21.62 | 4.11 | 20 |
| 21.85 | 4.06 | 50 |
| 22.11 | 4.02 | 30 |
| 22.38 | 3.97 | 34 |
| 22.79 | 3.90 | 54 |
| 24.12 | 3.69 | 43 |
| 24.40 | 3.64 | 83 |
| 26.08 | 3.41 | 30 |
| 26.86 | 3.32 | 23 |
| 27.56 | 3.23 | 34 |
| 28.51 | 3.13 | 21 |
| 29.22 | 3.05 | 14 |
| 29.63 | 3.01 | 17 |
| 29.94 | 2.98 | 9 |
| 30.86 | 2.90 | 15 |
| 31.13 | 2.87 | 28 |
| 31.40 | 2.85 | 14 |
| 31.83 | 2.81 | 14 |
| 32.38 | 2.76 | 10 |
| 32.92 | 2.72 | 16 |
| 33.23 | 2.69 | 15 |
| 33.89 | 2.64 | 12 |
| 34.37 | 2.61 | 9 |
| 35.49 | 2.53 | 13 |
| 35.92 | 2.50 | 12 |
| 36.12 | 2.48 | 16 |
| 36.91 | 2.43 | 16 |

TABLE 13-continued

XRPD peak list for deanol co-crystal Pattern 3

| Angle °2-Theta | d-spacing in Angstrom | Rel. Intensity % |
|---|---|---|
| 38.04 | 2.36 | 11 |
| 38.40 | 2.34 | 15 |
| 40.10 | 2.25 | 8 |

Further analysis of deanol Patterns 1, 2 and 3 gave the following results.

$^1$H-NMR investigation on Pattern 1 revealed shifts for the signals of psilocybin and suggested 6 equivalents of deanol.

$^1$H-NMR spectrum of Pattern 2 was consistent with the psilocybin structure but slight shifts were observed compared to the free drug starting material, suggesting changes in the molecular environment. One equivalent of deanol was estimated.

Pattern 2 was also investigated by DSC. A single thermal event was observed at 102.5° C. and corresponds to the melting peak of the compound, with a melting enthalpy of 121.2 J/g.

TG-FTIR analysis of deanol Pattern 2 revealed 20.4% of water and deanol loss from 25 to 225° C.

Solubility of Pattern 2 was 9.52 mg/mL in FaSSIF at 37° C. (pH of the solution is 6.5).

(vi) Piperazine

A mixture of 40 mg psilocybin with 1.1 equivalents of piperazine was suspended in ethyl acetate. After five days of stirring at r.t., the solid was isolated by filter centrifugation and PXRD investigation revealed a PXRD pattern herein designated as piperazine Pattern 1, the XRPD characteristics of which are shown in Table 14 below and in FIG. 9.

In a separate experiment, solvent drop grinding was conducted with 40 mg psilocybin and 1 equivalent of piperazine using an agate mortar and pestle. 50 µL of ethyl acetate was added to the powder mixture, and milling was conducted for 1-2 minutes. The obtained powder was then gathered in the middle of the mortar with a spatula, ethyl acetate was again added, and the milling process was repeated. This milling was conducted a total of three times. The resulting material was analysed by PXRD and a new PXRD pattern was obtained, herein designated as piperazine Pattern 2, the XRPD characteristics of which are shown in Table 15 below and in FIG. 10.

TABLE 14

XRPD peak list for piperazine co-crystal Pattern 1

| Angle °2-Theta | d-spacing in Angstrom | Rel. Intensity % |
|---|---|---|
| 7.99 | 11.05 | 11 |
| 9.21 | 9.60 | 36 |
| 11.31 | 7.82 | 41 |
| 13.13 | 6.74 | 61 |
| 14.47 | 6.12 | 11 |
| 15.04 | 5.88 | 42 |
| 15.35 | 5.77 | 57 |
| 15.74 | 5.62 | 17 |
| 16.53 | 5.36 | 7 |
| 17.67 | 5.02 | 19 |
| 17.94 | 4.94 | 16 |
| 18.47 | 4.80 | 24 |
| 19.33 | 4.59 | 26 |
| 20.49 | 4.33 | 15 |
| 20.93 | 4.24 | 9 |
| 21.40 | 4.15 | 10 |
| 21.86 | 4.06 | 7 |
| 22.73 | 3.91 | 27 |
| 23.81 | 3.73 | 27 |
| 24.43 | 3.64 | 100 |
| 25.58 | 3.48 | 10 |
| 26.46 | 3.37 | 12 |
| 27.15 | 3.28 | 8 |
| 27.89 | 3.20 | 12 |
| 28.64 | 3.11 | 6 |
| 28.98 | 3.08 | 9 |
| 29.94 | 2.98 | 9 |
| 30.64 | 2.92 | 11 |
| 30.86 | 2.90 | 9 |
| 31.93 | 2.80 | 5 |
| 33.50 | 2.67 | 7 |
| 33.95 | 2.64 | 6 |
| 35.02 | 2.56 | 4 |
| 35.61 | 2.52 | 7 |
| 36.28 | 2.47 | 5 |
| 37.37 | 2.40 | 5 |
| 38.11 | 2.36 | 6 |
| 38.46 | 2.34 | 6 |
| 39.25 | 2.29 | 4 |

TABLE 15

XRPD peak list for piperazine co-crystal Pattern 2

| Angle °2-Theta | d-spacing in Angstrom | Rel. Intensity % |
|---|---|---|
| 6.51 | 13.57 | 11 |
| 9.30 | 9.50 | 30 |
| 10.64 | 8.31 | 9 |
| 12.08 | 7.32 | 39 |
| 13.11 | 6.75 | 48 |
| 13.77 | 6.43 | 17 |
| 15.05 | 5.88 | 47 |
| 15.50 | 5.71 | 33 |
| 17.28 | 5.13 | 61 |
| 17.62 | 5.03 | 13 |
| 18.14 | 4.89 | 9 |
| 18.68 | 4.75 | 31 |
| 19.43 | 4.57 | 13 |
| 19.75 | 4.49 | 10 |
| 20.17 | 4.40 | 8 |
| 20.71 | 4.28 | 23 |
| 21.41 | 4.15 | 31 |
| 21.69 | 4.09 | 26 |
| 22.36 | 3.97 | 10 |
| 23.27 | 3.82 | 10 |
| 24.59 | 3.62 | 100 |
| 25.11 | 3.54 | 18 |
| 25.38 | 3.51 | 12 |
| 25.75 | 3.46 | 16 |
| 26.45 | 3.37 | 7 |
| 26.85 | 3.32 | 9 |
| 27.30 | 3.26 | 6 |
| 27.76 | 3.21 | 8 |
| 28.18 | 3.16 | 9 |
| 28.79 | 3.10 | 8 |
| 29.54 | 3.02 | 11 |
| 29.95 | 2.98 | 8 |
| 30.40 | 2.94 | 15 |
| 31.37 | 2.85 | 8 |
| 31.98 | 2.80 | 6 |
| 32.31 | 2.77 | 6 |
| 32.76 | 2.73 | 8 |
| 33.16 | 2.70 | 9 |
| 33.77 | 2.65 | 5 |
| 34.55 | 2.59 | 5 |
| 35.03 | 2.56 | 4 |
| 35.68 | 2.51 | 5 |

TABLE 15-continued

XRPD peak list for piperazine co-crystal Pattern 2

| Angle °2-Theta | d-spacing in Angstrom | Rel. Intensity % |
|---|---|---|
| 36.73 | 2.44 | 5 |
| 37.92 | 2.37 | 6 |
| 38.28 | 2.35 | 10 |
| 39.20 | 2.30 | 4 |
| 39.85 | 2.26 | 7 |
| 40.20 | 2.24 | 7 |

Further analysis of piperazine Patterns 1 and 2 gave the following results.

- Patterns 1 and 2 were investigated by $^1$H-NMR and approximately 0.5 equivalents of piperazine were estimated for each pattern.
- Pattern 2 was analysed by TG-FTIR, in which 7.5% of water, piperazine, and CO2 were lost from 25 to 190° C.
- DSC analysis of Pattern 2 shows a broad melting event at 121.5° C.
- DVS analysis showed that Pattern 2 was only very slightly hygroscopic, and showed no form conversion after analysis
- Solubility of Pattern 2 was 46.74 mg/mL in FaSSIF at 37° C. (pH of the solution is 6.2).

(vii) Pyridoxine

Approximately 40 mg psilocybin was suspended in a concentrated pyridoxine solution in NMP. After 6 days of stirring at 25° C., the suspension was filtered, and a wet cake was obtained. This sample was then dried under vacuum (<10 mbar) at r.t., and a new PXRD pattern was obtained, herein designated as pyridoxine Pattern 1, the XRPD characteristics of which are shown in Table 16 below and in FIG. 11.

TABLE 16

XRPD peak list for pyridoxine co-crystal Pattern 1

| Angle °2-Theta | d-spacing in Angstrom | Rel. Intensity % |
|---|---|---|
| 5.75 | 15.35 | 25 |
| 8.78 | 10.07 | 78 |
| 11.88 | 7.45 | 24 |
| 13.21 | 6.70 | 73 |
| 13.66 | 6.48 | 60 |
| 14.53 | 6.09 | 22 |
| 14.79 | 5.99 | 23 |
| 15.66 | 5.65 | 24 |
| 15.94 | 5.56 | 48 |
| 16.47 | 5.38 | 18 |
| 16.98 | 5.22 | 22 |
| 18.32 | 4.84 | 27 |
| 18.51 | 4.79 | 34 |
| 18.86 | 4.70 | 19 |
| 19.36 | 4.58 | 34 |
| 19.79 | 4.48 | 23 |
| 20.34 | 4.36 | 17 |
| 20.88 | 4.25 | 100 |
| 21.42 | 4.14 | 18 |
| 22.23 | 4.00 | 48 |
| 22.68 | 3.92 | 16 |
| 23.08 | 3.85 | 15 |
| 23.84 | 3.73 | 22 |
| 24.51 | 3.63 | 58 |
| 24.80 | 3.59 | 22 |
| 25.29 | 3.52 | 12 |
| 25.83 | 3.45 | 35 |
| 26.04 | 3.42 | 54 |
| 26.40 | 3.37 | 19 |
| 26.63 | 3.34 | 27 |
| 26.86 | 3.32 | 23 |
| 27.54 | 3.24 | 30 |
| 28.42 | 3.14 | 15 |
| 28.96 | 3.08 | 19 |
| 29.36 | 3.04 | 21 |
| 29.89 | 2.99 | 16 |
| 30.20 | 2.96 | 23 |
| 30.50 | 2.93 | 9 |
| 31.09 | 2.87 | 25 |
| 31.44 | 2.84 | 11 |
| 31.89 | 2.80 | 10 |
| 32.29 | 2.77 | 10 |
| 33.33 | 2.69 | 9 |
| 33.89 | 2.64 | 8 |
| 34.89 | 2.57 | 8 |
| 35.57 | 2.52 | 10 |
| 35.84 | 2.50 | 7 |
| 37.14 | 2.42 | 10 |
| 37.78 | 2.38 | 7 |
| 38.09 | 2.36 | 8 |
| 39.85 | 2.26 | 6 |
| 40.62 | 2.22 | 9 |

Further analysis of pyridoxine Pattern 1 gave the following results.

- The obtained $^1$H-NMR spectrum was consistent with the psilocybin structure, and 1.0 equivalents of pyridoxine were estimated.
- TG-FTIR analysis showed 1.7% of water loss from 25 to 130° C.
- Solubility of 13.67 mg/mL in FaSSIF at 37° C. (pH of the solution is 5.03).

(viii) Tert-butylamine

Approximately 40 mg psilocybin was suspended in tert-butylamine and stirred for five days at r.t. The solid was isolated by filtration, and the obtained wet material was submitted for PXRD investigation; the resulting PXRD pattern herein designated tert-butylamine Pattern 1, the XRPD characteristics of which are shown in Table 17 below and in FIG. 12.

The remaining wet sample was washed with TBME and the obtained solid was vacuum dried (<10 mbar, r.t.) overnight. A new PXRD pattern was observed, herein designated as tert-butylamine Pattern 2, the XRPD characteristics of which are shown in Table 18 below and in FIG. 13.

TABLE 17

XRPD peak list for tert-butylamine co-crystal Pattern 1

| Angle °2-Theta | d-spacing in Angstrom | Rel. Intensity % |
|---|---|---|
| 5.58 | 15.84 | 24.6 |
| 7.62 | 11.59 | 100 |
| 9.12 | 9.69 | 70.1 |
| 9.96 | 8.87 | 75.6 |
| 12.07 | 7.33 | 15.7 |
| 12.65 | 6.99 | 18.7 |
| 14.84 | 5.97 | 33.3 |
| 15.38 | 5.76 | 14.6 |
| 15.87 | 5.58 | 15.2 |
| 17.23 | 5.14 | 18.7 |
| 17.38 | 5.10 | 19.8 |
| 18.39 | 4.82 | 57.7 |
| 18.89 | 4.70 | 46.1 |

TABLE 17-continued

XRPD peak list for tert-butylamine co-crystal Pattern 1

| Angle °2-Theta | d-spacing in Angstrom | Rel. Intensity % |
|---|---|---|
| 19.24 | 4.61 | 26.6 |
| 20.63 | 4.30 | 24.9 |
| 21.49 | 4.13 | 73.9 |
| 22.34 | 3.98 | 15.5 |
| 23.42 | 3.80 | 21.8 |
| 24.44 | 3.64 | 19.1 |
| 25.54 | 3.48 | 14.2 |
| 26.28 | 3.39 | 16.9 |
| 28.07 | 3.18 | 9.2 |
| 28.93 | 3.08 | 14.8 |
| 29.55 | 3.02 | 12.2 |
| 30.15 | 2.96 | 19.5 |
| 30.69 | 2.91 | 8.8 |
| 31.18 | 2.87 | 12.6 |
| 31.94 | 2.80 | 7.9 |
| 33.14 | 2.70 | 7.3 |
| 34.51 | 2.60 | 7.2 |
| 35.00 | 2.56 | 6.9 |
| 35.50 | 2.53 | 7.9 |
| 36.24 | 2.48 | 9.3 |
| 37.35 | 2.41 | 6.4 |
| 38.38 | 2.34 | 5.6 |

TABLE 18

XRPD peak list for tert-butylamine co-crystal Pattern 2

| Angle °2-Theta | d-spacing in Angstrom | Rel. Intensity % |
|---|---|---|
| 7.65 | 11.55 | 100 |
| 9.16 | 9.65 | 77 |
| 9.96 | 8.88 | 78 |
| 14.83 | 5.97 | 48 |
| 18.43 | 4.81 | 61 |
| 18.92 | 4.69 | 57 |
| 19.27 | 4.60 | 51 |
| 20.60 | 4.31 | 50 |
| 21.49 | 4.13 | 72 |
| 21.92 | 4.05 | 47 |
| 23.48 | 3.79 | 44 |
| 26.31 | 3.38 | 32 |
| 30.16 | 2.96 | 25 |
| 35.49 | 2.53 | 18 |
| 36.19 | 2.48 | 17 |

Further analysis of tert-butylamine Pattern 2 gave the following results.

The obtained 1H-NMR spectrum was consistent with the psylocibin structure and shifts were observed compared to the spectrum of the free drug starting material. 1.0 equivalents of tert-butylamine could be determined from the NMR spectra.

TG-FTIR analysis showed 1.2% of water loss from 25 to 90° C. and 35.1% of water and TBA loss from 90 to 305° C.

Solubility of 8.27 mg/mL in FaSSIF at 37° C. (pH of the solution was 6.4).

(ix) Urea

Approximately 40 mg psilocybin and 1.1 equivalents of urea were suspended in acetonitrile. After seven days of stirring at r.t., the solid was isolated by filter centrifugation and the obtained material was dried in air for one hour. A new PXRD pattern was obtained, herein designated as urea Pattern 1, the XRPD characteristics of which are shown in Table 19 below and in FIG. 14.

TABLE 19

XRPD peak list for urea co-crystal Pattern 1

| Angle °2-Theta | d-spacing in Angstrom | Rel. Intensity % |
|---|---|---|
| 10.63 | 8.32 | 8 |
| 11.22 | 7.88 | 20 |
| 13.37 | 6.62 | 9 |
| 14.44 | 6.13 | 100 |
| 15.14 | 5.85 | 16 |
| 15.57 | 5.69 | 6 |
| 16.51 | 5.37 | 12 |
| 17.20 | 5.15 | 16 |
| 18.41 | 4.82 | 10 |
| 19.17 | 4.63 | 7 |
| 19.76 | 4.49 | 7 |
| 20.24 | 4.38 | 37 |
| 20.62 | 4.30 | 19 |
| 21.07 | 4.21 | 42 |
| 22.19 | 4.00 | 18 |
| 22.54 | 3.94 | 4 |
| 23.24 | 3.82 | 4 |
| 23.76 | 3.74 | 24 |
| 24.24 | 3.67 | 13 |
| 24.65 | 3.6 | 21 |
| 25.01 | 3.56 | 43 |
| 25.59 | 3.48 | 16 |
| 26.08 | 3.41 | 4 |
| 26.53 | 3.36 | 6 |
| 26.74 | 3.33 | 6 |
| 26.97 | 3.30 | 6 |
| 27.70 | 3.22 | 18 |
| 29.05 | 3.07 | 16 |
| 29.44 | 3.03 | 4 |
| 29.69 | 3.0 | 6 |
| 29.89 | 2.99 | 4 |
| 30.50 | 2.93 | 3 |
| 30.82 | 2.90 | 3 |
| 31.06 | 2.88 | 2 |
| 31.87 | 2.81 | 12 |
| 32.32 | 2.77 | 5 |
| 32.90 | 2.72 | 3 |
| 33.26 | 2.69 | 3 |
| 33.70 | 2.66 | 4 |
| 34.40 | 2.61 | 2 |
| 35.35 | 2.54 | 6 |
| 36.33 | 2.47 | 6 |
| 36.88 | 2.44 | 3 |
| 37.61 | 2.39 | 3 |
| 37.89 | 2.37 | 2 |
| 38.63 | 2.33 | 3 |
| 38.95 | 2.31 | 4 |
| 39.20 | 2.30 | 4 |
| 39.82 | 2.26 | 4 |
| 40.24 | 2.24 | 4 |

Further analysis of urea Pattern 1 gave the following results.

$^1$H-NMR investigation revealed a spectrum consistent with the psilocybin structure and 1.1 equivalents of urea were found.

(x) Propyl Gallate 450.0 mg of propyl gallate was suspended in 3 mL of acetonitrile. A beige suspension with fine particles was obtained and further stirred at r.t. in a closed vial. After overnight stirring, the suspension was filtered using a centrifugal unit filter (PTFE, 0.22 μm, 5000 rpm, 25° C., 3 min) and the recovered solution was added to 99.5 mg of psilocybin (~0.35 mmol). The obtained beige suspension was then stirred at 40° C. for one day. The temperature was decreased to 10° C. at 1° C./hour. A thick suspension was obtained, and 1 mL of acetonitrile was added. Further stirring at 10° C. was conducted for 5 days. A greyish suspension was obtained, and filtration was conducted using a centrifugal unit filter (PTFE, 0.22 μm, 5000 rpm, 25° C., 5 min). The wet cake was dried in air for 30 minutes and then submitted to PXRD investigation. A new PXRD pattern was obtained, herein designated as propyl gallate Pattern 1, the XRPD characteristics of which are shown in Table 20 below and in FIG. 15.

TABLE 20

XRPD peak list for propyl gallate co-crystal Pattern 1

| Angle °2-Theta | Intensity | Rel. Intensity % |
|---|---|---|
| 9.3 | 1490.98 | 64 |
| 10.56 | 1257.98 | 54 |
| 12.04 | 1154.02 | 50 |
| 12.82 | 944.93 | 41 |
| 15.02 | 1005.98 | 43 |
| 16.98 | 623.95 | 27 |
| 18.16 | 1411.06 | 61 |
| 19.32 | 1932.81 | 83 |
| 21.3 | 2330.06 | 100 |
| 22.08 | 933.02 | 40 |
| 24.44 | 1065.02 | 46 |
| 28.54 | 600.05 | 26 |

Further analysis of propyl gallate Pattern 1 gave the following results.

The 1H-NMR spectrum is consistent with the psilocybin structure and revealed 1.4 equivalents of propyl gallate.

SUMMARY

It has been shown that co-crystals form with psilocybin and these co-formers. The co-crystals have properties that make them useful in pharmaceutical settings, such as good solubility. For example, a co-crystal with piperazine has been shown to have excellent solubility in FaSSiF.

| Property | Co-former | | | |
|---|---|---|---|---|
| | Deanol | Piperazine | Pyridoxine | Tert-butylamine |
| XRPD pattern | Pattern 2 | Pattern 2 | Pattern 1 | Pattern 2 |
| Thermal properties | Single $T_M$ at 103° C. associated with ~20% weight loss | Broad $T_M$ at 122° C. With 7.5% weight loss | Multiple endotherms. 1.7% weight loss | Multiple endotherms. ~35% weight loss |
| Solubility in FaSSiF (mg/ml) | 9.5 | 46.7 | 13.7 | 8.3 |

ASPECTS OF THE INVENTION

In one embodiment, the invention provides the following aspects:

1. A co-crystal comprising psilocybin and a co-former, wherein the co-former is an acid.
2. A co-crystal according to aspect 1, wherein the co-former is an organic acid.
3. A co-crystal according to aspect 1 or aspect 2, wherein the co-former is a compound which comprises one or more of a carboxylic acid moiety, a sulfonic acid moiety, a squaric acid moiety, a sulphonamide moiety, a carboxylic sulfonimide moiety, and a sulfimide moiety.
4. A co-crystal according to any one of the preceding aspects, wherein the co-former is a compound which comprises a carboxylic acid moiety.
5. A co-crystal according to any one of the preceding aspects, wherein the co-former has a $pK_a$ of less than or equal to 7.0.
6. A co-crystal according to any one of the preceding aspects, wherein the co-former has a $pK_a$ of less than or equal to 6.0.
7. A co-crystal according to any one of the preceding aspects, wherein the co-former has a $pK_a$ of greater than or equal to 1.5.
8. A co-crystal according to any one of the preceding aspects, wherein the co-former as a $pK_a$ of greater than or equal to 2.5.
9. A co-crystal according to any one of the preceding aspects, wherein the molar ratio of psilocybin:co-former is from 1:0.25 to 1:4.
10. A co-crystal according to aspect 9, wherein the molar ratio of psilocybin:co-former is about 1:0.5.
11. A co-crystal according to aspect 9, wherein the molar ratio of psilocybin:co-former is about 1:1.
12. A co-crystal according to aspect 9, wherein the molar ratio of psilocybin:co-former is about 1:2.
13. A co-crystal according to any one of the preceding aspects, wherein the co-crystal is in the form of a solvate or hydrate.
14. A co-crystal according to aspect 13, wherein the solvate or hydrate is stoichiometric or non-stoichiometric.
15. A co-crystal according to any one of the preceding aspects, wherein the co-former is selected from: N-acetyl glycine, alginic acid, 2-(4-hydroxybenzoyl) benzoic acid, gluconic acid, glucoheptonic acid, 2-naphthoic acid, orotic acid, succinic acid, L-ascorbic acid, L-tartaric acid, cinnamic acid, ferulic acid, fumaric acid, gentisic acid, gallic acid, citric acid, p-coumaric acid, L-lactic acid, disodium EDTA, nicotinic acid, 1-hydroxy-2-naphthoic acid, 2-ketoglutaric acid, 4-hydroxyphenyl acetic acid, L-malic acid, maleic acid, oxalic acid and saccharin.
16. A co-crystal according to aspect 15, wherein the co-former is selected from: citric acid, fumaric acid, succinic acid, gluconic acid, L-tartaric acid, L-ascorbic acid, L-lactic acid, saccharin, and nicotinic acid.
17. A pharmaceutical composition comprising:
   (a) a co-crystal as defined in any one of the preceding aspects; and
   (b) a pharmaceutically acceptable excipient or diluent.
18. A process for producing a co-crystal as defined in any one of aspects 1 to 16, the process comprising combining psilocybin and a co-former which is an acid.
19. A method of treating or preventing a disease or condition selected from psychological, neurological and central nervous system disorders in a patient, the method comprising administering a therapeutically effective amount of a co-crystal as defined in any one of aspects 1 to 16 to the patient.
20. The method of aspect 19, wherein the disease or condition is selected from depression, anxiety, death anxiety, demoralization, hopelessness, suicidal ideation and desire for hastened death.
21. A co-crystal as defined in any one of aspects 1 to 16 for use in the treatment or prevention of a disease or condition as defined in aspect 19 or aspect 20.
22. Use of a co-crystal as defined in any one of aspects 1 to 16 in the manufacture of a medicament for the treatment or prevention of a disease or condition as defined in aspect 19 or aspect 20.

23. A kit comprising:
   a co-crystal as defined in any one of aspects 1 to 16 or a pharmaceutical composition as defined in aspect 17; and
   instructions for use of the co-crystal or pharmaceutical composition in a method of treating or preventing a disease or condition as defined in aspect 19 or aspect 20.

In a second embodiment, the invention provides the following aspects:

1. A co-crystal comprising psilocybin and a co-former, wherein the co-former is a base.
2. A co-crystal according to aspect 1, wherein the co-former is an organic base.
3. A co-crystal according to aspect 1 or aspect 2, wherein the co-former is a compound which comprises one or more of an amine moiety, a pyridine moiety, a piperazine moiety, an amide moiety, a xanthine moiety and a morpholine moiety.
4. A co-crystal according to any one of the preceding aspects, wherein the co-former is a compound which comprises an amine moiety.
5. A co-crystal according to any one of the preceding aspects, wherein the co-former has a $pK_b$ of less than or equal to 11.0.
6. A co-crystal according to any one of the preceding aspects, wherein the co-former has a $pK_b$ of less than or equal to 9.0.
7. A co-crystal according to any one of the preceding aspects, wherein the co-former has a $pK_b$ of greater than or equal to 3.5.
8. A co-crystal according to any one of the preceding aspects, wherein the co-former as a $pK_b$ of greater than or equal to 4.5.
9. A co-crystal according to any one of the preceding aspects, wherein the molar ratio of psilocybin:co-former is from 1:0.25 to 1:4.
10. A co-crystal according to aspect 9, wherein the molar ratio of psilocybin:co-former is about 1:0.5.
11. A co-crystal according to aspect 9, wherein the molar ratio of psilocybin:co-former is about 1:1.
12. A co-crystal according to aspect 9, wherein the molar ratio of psilocybin:co-former is about 1:2.
13. A co-crystal according to any one of the preceding aspects, wherein the co-crystal is in the form of a solvate or hydrate.
14. A co-crystal according to aspect 13, wherein the solvate or hydrate is stoichiometric or non-stoichiometric.
15. A co-crystal according to any one of the preceding aspects, wherein the co-former is selected from: 4,4-bipyridine, pyridoxine, deanol, 4-(2-hydroxyethyl)-morpholine, piperazine, theophylline, nicotinamide, isonicotinamide, tromethamine, tert-butyl amine and diethylamine.
16. A co-crystal according to aspect 15, wherein the co-former is selected from: theophylline, nicotinamide, isonicotinamide, and tromethamine.
17. A pharmaceutical composition comprising:
   (a) a co-crystal as defined in any one of the preceding aspects; and
   (b) a pharmaceutically acceptable excipient or diluent.
18. A process for producing a co-crystal as defined in any one of aspects 1 to 16, the process comprising combining psilocybin and a co-former which is a base.
19. A method of treating or preventing a disease or condition selected from psychological, neurological and central nervous system disorders in a patient, the method comprising administering a therapeutically effective amount of a co-crystal as defined in any one of aspects 1 to 16 to the patient.
20. The method of aspect 19, wherein the disease or condition is selected from depression, anxiety, death anxiety, demoralization, hopelessness, suicidal ideation and desire for hastened death.
21. A co-crystal as defined in any one of aspects 1 to 16 for use in the treatment or prevention of a disease or condition as defined in aspect 19 or aspect 20.
22. Use of a co-crystal as defined in any one of aspects 1 to 16 in the manufacture of a medicament for the treatment or prevention of a disease or condition as defined in aspect 19 or aspect 20.
23. A kit comprising:
   a co-crystal as defined in any one of aspect 1 to 16 or a pharmaceutical composition as defined in aspect 17; and
   instructions for use of the co-crystal or pharmaceutical composition in a method of treating or preventing a disease or condition as defined in aspect 19 or aspect 20.

In a third embodiment, the invention provides the following aspects:

1. A co-crystal comprising psilocybin and a co-former, wherein the co-former is a neutral compound, which neutral compound is:
   (i) a compound which is amphoteric;
   (ii) a compound which is zwitterionic;
   (iii) a compound which comprises neither an acidic moiety nor a basic moiety; or
   (iv) a compound which is an inorganic salt.
2. A co-crystal according to aspect 1, wherein the co-former is a compound which is amphoteric.
3. A co-crystal according to aspect 2, wherein the co-former is an amino acid or amino acid derivative.
4. A co-crystal according to aspect 3, wherein the co-former is selected from: L-lysine, L-histidine, L-tyrosine, L-pyroglutamic acid, DL-cysteine, and L-glutamic acid.
5. A co-crystal according to aspect 4, wherein the co-former is selected from: L-pyroglutamic acid, DL-cysteine, and L-glutamic acid.
6. A co-crystal according to aspect 1, wherein the co-former is a compound which comprises neither an acidic moiety nor a basic moiety.
7. A co-crystal according to aspect 6, wherein the co-former is a compound which comprises an ester moiety.
8. A co-crystal according to aspect 6, wherein the co-former is a compound which comprises an ether moiety.
9. A co-crystal according to aspect 6, wherein the co-former is a compound which comprises an alcohol moiety.
10. A co-crystal according to aspect 6, wherein the co-former is selected from: ethyl maltol, meso-erythritol, D-mannitol, D-sorbitol, D-xylitol, inosine, and L-ascorbic acid 6-hexadecanoate.
11. A co-crystal according to aspect 6, wherein the co-former is a compound which comprises a phenol moiety.
12. A co-crystal according to aspect 11, wherein the co-former is selected from: 2,6-di-tert-butyl-4-methylphenol, 2-tert-butyl-4-methoxyphenol, vanillin, ethyl vanillin, $C_{1-4}$ parabens, propyl gallate.

13. A co-crystal according to aspect 12, wherein the co-former is selected from: propyl gallate, 2,6-di-tert-butyl-4-methylphenol, and 2-tert-butyl-4-methoxyphenol.

14. A co-crystal according to aspect 6, where the co-former is a compound which comprises a carboxamide moiety.

15. A co-crystal according to aspect 14, wherein the co-former is urea.

16. A co-crystal according to aspect 1, wherein the co-former is an inorganic salt.

17. A co-crystal according to aspect 16, wherein the co-former is selected from: sodium dihydrogen phosphate, sodium bisulfite, acesulfame potassium and sodium formaldehyde sulfoxylate.

18. A co-crystal according to aspect 17, wherein the co-former is selected from: sodium bisulfite, acesulfame potassium, and sodium formaldehyde sulfoxylate.

19. A co-crystal according to any one of the preceding aspects, wherein the molar ratio of psilocybin:co-former is from 1:0.25 to 1:4.

20. A co-crystal according to aspect 19, wherein the molar ratio of psilocybin:co-former is about 1:0.5.

21. A co-crystal according to aspect 19, wherein the molar ratio of psilocybin:co-former is about 1:1.

22. A co-crystal according to aspect 19, wherein the molar ratio of psilocybin:co-former is about 1:2.

23. A co-crystal according to any one of the preceding aspects, wherein the co-crystal is in the form of a solvate or hydrate.

24. A co-crystal according to aspect 23, wherein the solvate or hydrate is stoichiometric or non-stoichiometric.

25. A pharmaceutical composition comprising:
(a) a co-crystal as defined in any one of the preceding aspects; and
(b) a pharmaceutically acceptable excipient or diluent.

26. A process for producing a co-crystal as defined in any one of aspects 1 to 22, the process comprising combining psilocybin and a co-former which is as defined in aspect 1.

27. A method of treating or preventing a disease or condition selected from psychological, neurological and central nervous system disorders in a patient, the method comprising administering a therapeutically effective amount of a co-crystal as defined in any one of aspects 1 to 24 to the patient.

28. The method of aspect 27, wherein the disease or condition is selected from depression, anxiety, death anxiety, demoralization, hopelessness, suicidal ideation and desire for hastened death.

29. A co-crystal as defined in any one of aspects 1 to 24 for use in the treatment or prevention of a disease or condition as defined in aspect 27 or aspect 28.

30. Use of a co-crystal as defined in any one of aspects 1 to 24 in the manufacture of a medicament for the treatment or prevention of a disease or condition as defined in aspect 27 or aspect 28.

31. A kit comprising:
a co-crystal as defined in any one of aspects 1 to 24 or a pharmaceutical composition as defined in aspect 25; and
instructions for use of the co-crystal or pharmaceutical composition in a method of treating or preventing a disease or condition as defined in aspect 27 or aspect 28.

The invention claimed is:

1. A co-crystal or salt comprising psilocybin and a co-former, wherein the co-former is piperazine, and wherein the co-crystal or salt is in the form of crystalline piperazine Pattern 1 having an x-ray powder diffraction pattern comprising peaks at 13.1°, 15.4° and 24.4°±0.2° 2θ.

2. A co-crystal or salt according to claim 1, wherein the x-ray powder diffraction pattern further comprises peaks at 9.2°, 11.3° and 15.0°±0.2° 2θ.

3. A co-crystal or salt according to claim 1, wherein the x-ray powder diffraction pattern comprises seven or more peaks selected from 9.2°, 11.3°, 13.1°, 15.0°, 15.4°, 19.3°, 22.7°, 23.8° and 24.4°±0.2° 2θ.

4. A co-crystal or salt comprising psilocybin and a co-former, wherein the co-former is piperazine, and wherein the co-crystal or salt is in the form of crystalline piperazine Pattern 2 having an x-ray powder diffraction pattern comprising peaks at 13.1°, 17.3° and 24.6°±0.2° 2θ.

5. A co-crystal or salt according to claim 4, wherein the x-ray powder diffraction pattern further comprises peaks at 12.1°, 15.1° and 15.5°±0.2° 2θ.

6. A co-crystal or salt according to claim 4, wherein the x-ray powder diffraction pattern comprises seven or more peaks selected from 9.3°, 12.1°, 13.1°, 15.1°, 15.5°, 17.3°, 18.7°, 21.4° and 24.6°±0.2° 2θ.

7. A pharmaceutical composition comprising:
(a) a co-crystal or salt as defined in claim 1; and
(b) a pharmaceutically acceptable excipient or diluent.

8. A pharmaceutical composition comprising:
(a) a co-crystal or salt as defined in claim 4; and
(b) a pharmaceutically acceptable excipient or diluent.

9. A kit comprising: a co-crystal or salt as defined in claim 1.

10. A kit comprising: a co-crystal or salt as defined in claim 4.

11. A method of treating a disease or condition selected from depression, anxiety, and demoralization in a patient, the method comprising administering a therapeutically effective amount of the co-crystal or salt as defined in claim 1 to the patient.

12. A method of treating a disease or condition selected from depression, anxiety, and demoralization in a patient, the method comprising administering a therapeutically effective amount of the pharmaceutical composition as defined in claim 7 to the patient.

13. A method of treating a disease or condition selected from depression, anxiety, and demoralization in a patient, the method comprising administering a therapeutically effective amount of the co-crystal or salt as defined in claim 4 to the patient.

* * * * *